United States Patent
Bigot et al.

(10) Patent No.: US 11,459,318 B2
(45) Date of Patent: *Oct. 4, 2022

(54) PESTICIDALLY ACTIVE PYRROLE DERIVATIVES

(71) Applicant: Syngenta Participations AG, Basel (CH)

(72) Inventors: Aurelien Bigot, Stein (CH); Myriem El Qacemi, Stein (CH); Denis Gribkov, Münchwilen (CH); André Stoller, Stein (CH)

(73) Assignee: Syngenta Participations AG, Basel (CH)

(*) Notice: Subject to any disclaimer, the term of this patent is extended or adjusted under 35 U.S.C. 154(b) by 94 days.

This patent is subject to a terminal disclaimer.

(21) Appl. No.: 16/754,050

(22) PCT Filed: Oct. 4, 2018

(86) PCT No.: PCT/EP2018/077030
§ 371 (c)(1),
(2) Date: Apr. 6, 2020

(87) PCT Pub. No.: WO2019/068819
PCT Pub. Date: Apr. 11, 2019

(65) Prior Publication Data
US 2020/0392124 A1    Dec. 17, 2020

(30) Foreign Application Priority Data

Oct. 6, 2017 (EP) ..................... 17195288
Nov. 1, 2017 (EP) ..................... 17199548

(51) Int. Cl.
| | | |
|---|---|---|
| *C07D 413/04* | (2006.01) | |
| *C07D 401/14* | (2006.01) | |
| *C07D 403/04* | (2006.01) | |
| *A01N 43/80* | (2006.01) | |
| *A01N 43/56* | (2006.01) | |

(52) U.S. Cl.
CPC ........... *C07D 413/04* (2013.01); *A01N 43/56* (2013.01); *A01N 43/80* (2013.01); *C07D 401/14* (2013.01); *C07D 403/04* (2013.01)

(58) Field of Classification Search
None
See application file for complete search history.

(56) References Cited

U.S. PATENT DOCUMENTS 10,047,076 B2    8/2018    Maue et al.

FOREIGN PATENT DOCUMENTS

| WO | 2015150442 A1 | 10/2015 |
|---|---|---|
| WO | 2016109288 A1 | 7/2016 |
| WO | 2016109300 A1 | 7/2016 |
| WO | 2016122802 A1 | 8/2016 |
| WO | 2016174049 A1 | 11/2016 |
| WO | 2017012970 A2 | 1/2017 |

OTHER PUBLICATIONS

Pharmablock "pyrazoles in drug discovery" https://www.pharmablock.com/cn/web/upload/2020/03/06/15834758432779op2p.pdf, 2020 p. 1-18.(Year:2020) (Year: 2020).*
International Search Report and Written Opinion for International Application No. PCT/EP2018/077030, dated Nov. 7, 2018.

* cited by examiner

*Primary Examiner* — Erin E Hirt
(74) *Attorney, Agent, or Firm* — BakerHostetler; Toni-Junell Herbert

(57) ABSTRACT

Compounds of formula (I) as defined herein, to processes for preparing them, to pesticidal, in particular insecticidal, acaricidal, molluscicidal and nematicidal compositions comprising them and to methods of using them to combat and control pests such as insect, acarine, mollusc and nematode pests.

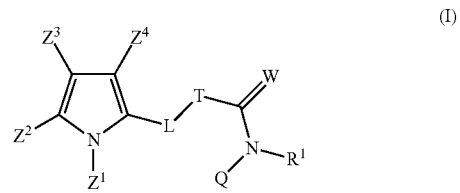

(I)

20 Claims, No Drawings

PESTICIDALLY ACTIVE PYRROLE DERIVATIVES

CROSS-REFERENCE TO RELATED APPLICATIONS

This application is a 371 National Stage application of International Application No. PCT/EP2018/077030 filed Oct. 4, 2018 which claims priority to EP 17195288.0, filed Oct. 6, 2017 and EP 17199548.3 filed on Nov. 1, 2017, the entire contents of which applications are hereby incorporated by reference.

The present invention relates to pyrazole derivatives, to processes for preparing them, to intermediates for preparing them, to pesticidal, in particular insecticidal, acaricidal, molluscicidal and nematicidal compositions comprising those derivatives and to methods of using them to combat and control pests such as insect, acarine, mollusc and nematode pests.

It has now surprisingly been found that certain pyrazole derivatives have highly potent insecticidal properties. Other compounds in this area are known from WO2014/122083, WO2012/107434, WO2015/067646, WO2015/067647, WO2015/067648, WO2015/150442, WO2015/193218, WO2010/051926 and WO2017/012970.

Thus, as embodiment 1, the present invention relates to a compound of formula (I),

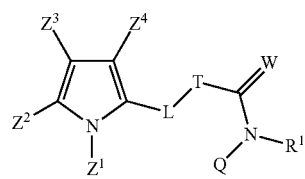

(I)

wherein $R^1$ is selected from H, $C_1$-$C_6$-alkyl, $C_2$-$C_6$ alkenyl, $C_2$-$C_6$ alkynyl, —$C_0$-$C_3$-alkyl-$C_3$-$C_7$ cycloalkyl, —C(=O)—$C_1$-$C_6$-alkyl, —C(=O)—O—$C_1$-$C_6$-alkyl, —C(=O)—N—($C_1$-$C_6$-alkyl)$_2$, —($C_0$-$C_3$)-alkyl-aryl and —($C_0$-$C_3$)-alkyl-heteroaryl, wherein each of $C_1$-$C_6$-alkyl, $C_2$-$C_6$ alkenyl, $C_2$-$C_6$ alkynyl, —$C_0$-$C_3$-alkyl-$C_3$-$C_7$ cycloalkyl, —C(=O)—$C_1$-$C_6$-alkyl, —C(=O)—O—$C_1$-$C_6$-alkyl, —C(=O)—N—($C_1$-$C_6$-alkyl)$_2$, —($C_0$-$C_3$)-alkyl-aryl and —($C_0$-$C_3$)-alkyl-heteroaryl is unsubstituted or substituted with 1 to 7 substituents independently selected from halogen, cyano, $C_1$-$C_6$-alkoxy and —C(=O)—O—$C_1$-$C_6$-alkyl;

Q is selected from H, hydroxy, —C(=O)H, $C_1$-$C_6$-alkyl, $C_1$-$C_6$-alkoxy, $C_2$-$C_6$alkenyl, $C_2$-$C_6$ alkynyl, —$C_0$-$C_3$-alkyl-$C_3$-$C_7$ cycloalkyl, —$C_0$-$C_3$-alkyl-$C_3$-$C_7$ heterocycloalkyl, —$C_0$-$C_3$-alkyl-aryl, —$C_0$-$C_3$-alkyl-heteroaryl, —NH—($C_1$-$C_6$-alkyl), —N—($C_1$-$C_6$-alkyl)$_2$ and —C(=O)N—($C_1$-$C_6$-alkyl)$_2$, wherein each of $C_1$-$C_6$-alkyl, $C_1$-$C_6$-alkoxy, $C_2$-$C_6$ alkenyl, $C_2$-$C_6$ alkynyl, —$C_0$-$C_3$-alkyl-$C_3$-$C_7$ cycloalkyl, —$C_0$-$C_3$-alkyl-$C_3$-$C_7$ heterocycloalkyl, —$C_0$-$C_3$-alkyl-aryl, —$C_0$-$C_3$-alkyl-heteroaryl, —NH—($C_1$-$C_6$-alkyl), —N—($C_1$-$C_6$-alkyl)$_2$ and —C(=O)N—($C_1$-$C_6$-alkyl)$_2$ is unsubstituted or substituted with 1 to 7 substituents independently selected from halogen, hydroxyl, nitro, amino, cyano, $C_1$-$C_6$-haloalkyl, $C_1$-$C_6$-alkoxy, $C_1$-$C_6$-alkoxycarbonyl, —C(=O)OH, $C_1$-$C_6$-alkylcarbamoyl, —C(=O)NH$_2$, —C(=S)NH$_2$, $C_3$-$C_6$-cycloalkylcarbamoyl and phenyl;

W is O or S;
L is selected from

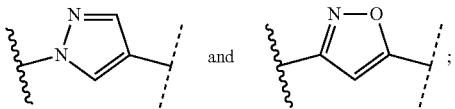

and

;

wherein

indicates the bond to the group

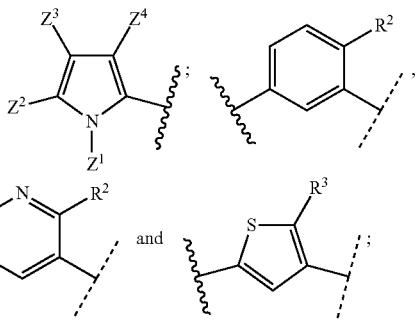

and

;

T is selected from
wherein

indicates the bond to the L group;
$R^2$ is H, Cl or Br;
$R^3$ is selected from Cl, Br and CN;
$Z^1$ is selected from H, $C_1$-$C_6$-alkyl and $C_3$-$C_6$-cycloalkyl wherein $C_1$-$C_6$-alkyl and $C_3$-$C_6$-cycloalkyl is unsubstituted or substituted with 1 to 9 substituents independently selected from halogen, cyano and $C_1$-$C_6$-alkoxy;
$Z^2$ and $Z^4$ are independently selected from H, halogen, cyano, nitro, $C_1$-$C_6$-alkyl, —C(=S)—NH$_2$, —C(=S)—NH($C_1$-$C_6$-alkyl), —C(=S)—N($C_1$-$C_6$-alkyl)$_2$, $C_3$-$C_7$ heterocycloalkyl, $C_3$-$C_6$-cycloalkyl, —S—$C_1$-$C_6$-alkyl, —S—$C_3$-$C_5$-cycloalkyl, —SO—$C_1$-$C_6$-alkyl, —SO—$C_3$-$C_5$-cycloalkyl, —SO$_2$—$C_1$-$C_6$-alkyl, —SO$_2$—$C_3$-$C_5$-cycloalkyl, —SO$_2$—O—$C_1$-$C_6$-alkyl, —SO$_2$—O—$C_3$-$C_5$-cycloalkyl, —$C_0$-$C_3$-alkyl-aryl, —$C_0$-$C_3$-alkyl-heteroaryl, wherein each of —C(=S)—NH($C_1$-$C_6$-alkyl), —C(=S)—N($C_1$-$C_6$-alkyl)$_2$, $C_1$-$C_6$-alkyl, $C_3$-$C_7$ heterocycloalkyl, $C_3$-$C_6$-cycloalkyl, —S—$C_1$-$C_6$-alkyl, —S—$C_3$-$C_5$-cycloalkyl, —SO—$C_1$-$C_6$-alkyl, —SO—$C_3$-$C_5$-cycloalkyl, —SO$_2$—$C_1$-$C_6$-alkyl, —SO$_2$—$C_3$-$C_5$-cycloalkyl, —SO$_2$—O—$C_1$-$C_6$-alkyl, —SO$_2$—O—$C_3$-$C_5$-cycloalkyl, —$C_0$-$C_3$-alkyl-aryl and —$C_0$-$C_3$-alkyl-heteroaryl is unsubstituted or substituted with 1 to 9 substituents independently selected from halogen, hydroxy, nitro, amino, cyano, $C_1$-$C_6$-alkyl, $C_1$-$C_6$-haloalkyl, $C_1$-$C_6$-alkoxy, $C_1$-$C_6$-alkoxycarbonyl and hydroxycarbonyl;
$Z^3$ is selected from H and halogen;
or an agrochemically acceptable salt thereof.

Preferred values of $R^1$, Q, L, T, W, $Z^1$, $Z^2$, $Z^3$ and $Z^4$ in relation to each compound of the present invention, including the intermediate compounds, are as set out below in embodiments 2 to 25.

As used herein, when one embodiment refers to several other embodiments by using the term "according to any one of", for example "according to any one of embodiments 1 to 23", then said embodiment refers not only to embodiments indicated by integers such as 1 and 2 but also to embodiments indicated by numbers with a decimal component such as for example 23.1, 23.2, 23.3, 23.4, 23.20, 23.25, 23.30.

Embodiment 2: A compound or salt according to embodiment 1, wherein T is

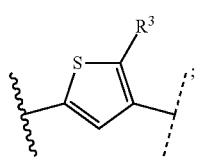

wherein

indicates the bond to the L group;
$R^3$ is selected from Cl, Br and CN, in particular CN.

Embodiment 3: A compound or salt according to embodiment 1, wherein T is

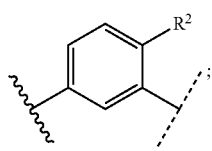

wherein

indicates the bond to the L group;
$R^2$ is H, Cl or Br.

Embodiment 4: A compound or salt according to embodiment 1, wherein T is

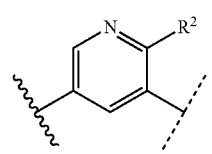

wherein

indicates the bond to the L group;
$R^2$ is H, Cl or Br.

Embodiment 5: A compound or salt according to any one of embodiments 1 to 4, wherein L is

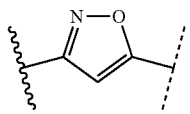

wherein

indicates the bond to the group

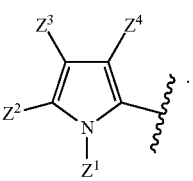

Embodiment 6: A compound or salt according to any one of embodiments 1 to 4, wherein L is

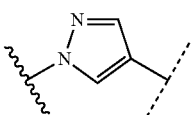

wherein

indicates the bond to the group

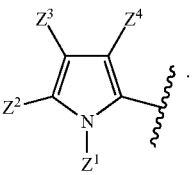

Embodiment 7: A compound or salt according to any one of embodiments 1 to 6, wherein
$R^1$ is selected from H and $C_1$-$C_6$-alkyl.
Embodiment 7.1: A compound or salt according to any one of embodiments 1 to 6, wherein
$R^1$ is selected from H, methyl and ethyl.
Embodiment 8: A compound or salt according to any one of embodiments 1 to 7, wherein
Q is $C_3$-$C_6$-cycloalkyl which is unsubstituted or substituted with 1 to 3 substituents independently selected from halogen and cyano.
Embodiment 8.1: A compound or salt according to any one of embodiments 1 to 7, wherein
Q is selected from 1-cyano-cyclopropyl and cyclopropyl.
Embodiment 9: A compound or salt according to any one of embodiments 1 to 8, wherein
W is O.
Embodiment 10: A compound or salt according to any one of embodiments 1 to 9, wherein
$Z^1$ is selected from H and $C_1$-$C_6$-alkyl wherein $C_1$-$C_6$-alkyl is unsubstituted or substituted with 1 to 7 substituents independently selected from halogen, cyano and $C_1$-$C_6$-alkoxy;
Embodiment 11: A compound or salt according to any one of embodiments 1 to 9, wherein
$Z^1$ is selected from methyl, ethyl, —$CH_2CN$, —$CH_2F$, —$CHF_2$, —$CF_3$ and —$CH_2$—O—$CH_3$.
Embodiment 12: A compound or salt according to any one of embodiments 1 to 9, wherein
$Z^1$ is selected from methyl, —$CH_2CN$, —$CH_2F$ and —$CH_2$—O—$CH_3$.
Embodiment 13: A compound or salt according to any one of embodiments 1 to 12, wherein
$Z^2$ is selected from halogen, $C_1$-$C_6$-alkyl, —S—$C_1$-$C_6$-alkyl, —S—$C_3$-$C_5$-cycloalkyl, —SO—$C_1$-$C_6$-alkyl, —SO—$C_3$-$C_5$-cycloalkyl, —$SO_2$—$C_1$-$C_6$-alkyl, —$SO_2$—$C_3$-$C_5$-cycloalkyl, —$SO_2$—O—$C_1$-$C_6$-alkyl, —$SO_2$—O—$C_3$-$C_5$-cycloalkyl, —$C_0$-$C_3$-alkyl-aryl and —$C_0$-$C_3$-alkyl-heteroaryl, wherein each of —C(=S)—NH($C_1$-$C_6$-alkyl), —C(=S)—N($C_1$-$C_6$-alkyl)$_2$, $C_1$-$C_6$-alkyl, $C_3$-$C_7$ heterocycloalkyl, $C_3$-$C_6$-cycloalkyl, —S—$C_1$-$C_6$-alkyl, —S—$C_3$-$C_5$-cycloalkyl, —SO—$C_1$-$C_6$-alkyl, —SO—$C_3$-$C_5$-cycloalkyl, —$SO_2$—$C_1$-$C_6$-alkyl, —$SO_2$—$C_3$-$C_5$-cycloalkyl, —$SO_2$—O—$C_1$-$C_6$-alkyl, —$SO_2$—O—$C_3$-$C_5$-cycloalkyl, —$C_0$-$C_3$-alkyl-aryl and —$C_0$-$C_3$-alkyl-heteroaryl is unsubstituted or substituted with 1 to 7 substituents independently selected from halogen.
Embodiment 14: A compound or salt according to any one of embodiments 1 to 12, wherein
$Z^2$ is selected from halogen, $C_1$-$C_6$-alkyl, —S—$C_1$-$C_6$-alkyl and —$C_0$-$C_3$-alkyl-aryl, wherein each of $C_1$-$C_6$-alkyl, —S—$C_1$-$C_6$-alkyl and —$C_0$-$C_3$-alkyl-aryl is unsubstituted or substituted with 1 to 7 substituents independently selected from halogen.
Embodiment 15: A compound or salt according to any one of embodiments 1 to 12, wherein
$Z^2$ is selected from $C_1$-$C_6$-alkyl which is substituted with 1 to 7 substituents independently selected from fluoro.
Embodiment 16: A compound or salt according to any one of embodiments 1 to 12, wherein
$Z^2$ is —$CF(CF_3)(CF_3)$.
Embodiment 17: A compound or salt according to any one of embodiments 1 to 16, wherein
$Z^3$ is H.
Embodiment 18: A compound or salt according to any one of embodiments 1 to 16, wherein
$Z^3$ is bromo.
Embodiment 19: A compound or salt according to any one of embodiments 1 to 18, wherein
$Z^4$ is selected from H, halogen, nitro, cyano, $C_1$-$C_6$-alkyl, —C(=S)—$NH_2$, —C(=S)—NH($C_1$-$C_6$-alkyl), —C(=S)—N($C_1$-$C_6$-alkyl)$_2$, —S—$C_1$-$C_6$-alkyl, —SO—$C_1$-$C_6$-alkyl, —$SO_2$—$C_1$-$C_6$-alkyl and —$SO_2$—O—$C_1$-$C_6$-alkyl, wherein each of $C_1$-$C_6$-alkyl, —C(=S)—$NH_2$, —C(=S)—NH($C_1$-$C_6$-alkyl), —C(=S)—N($C_1$-$C_6$-alkyl)$_2$, —S—$C_1$-$C_6$-alkyl, —SO—$C_1$-$C_6$-alkyl, —$SO_2$—$C_1$-$C_6$-alkyl and —$SO_2$—O—$C_1$-$C_6$-alkyl is unsubstituted or substituted with 1 to 7 halogen substituents.
Embodiment 20: A compound or salt according to any one of embodiments 1 to 18, wherein
$Z^4$ is selected from H, halogen, nitro, cyano, $C_1$-$C_6$-alkyl, —C(=S)—$NH_2$, wherein $C_1$-$C_6$-alkyl is unsubstituted or substituted with 1 to 7 substituents selected from halogen, in particular fluoro.
Embodiment 21: A compound or salt according to any one of embodiments 1 to 18, wherein
$Z^4$ is selected from H, halogen, nitro, cyano, methyl, trifluoromethyl and —C(=S)—$NH_2$.
Embodiment 22: A compound or salt according to any one of embodiments 1 to 9, wherein
$Z^1$ is $C_1$-$C_6$-alkyl wherein $C_1$-$C_6$-alkyl is unsubstituted or substituted with 1 to 7 halogen substituents;
$Z^2$ is selected from $C_1$-$C_6$-alkyl which is substituted with 1 to 7 halogen substituents;
$Z^3$ is H or bromo;
$Z^4$ is selected from H, halogen, nitro, cyano, methyl, trifluoromethyl and —C(=S)—$NH_2$.
Embodiment 23: A compound or salt according to any one of embodiments 1 to 9, wherein
$Z^1$ is selected from methyl, —$CH_2CN$, —$CH_2F$ and —$CH_2$—O—$CH_3$.
$Z^2$ is selected from —$CF(CF_3)(CF_3)$;
$Z^3$ is H or bromo;
$Z^4$ is selected from H, halogen, nitro, cyano, methyl, trifluoromethyl and —C(=S)—$NH_2$.
Embodiment 24: A compound or salt according to embodiment 1 selected from

| Example No. | Structure | Chemical name |
|---|---|---|
| 1 | 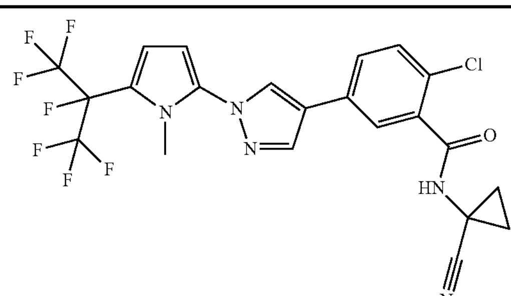 | 2-chloro-N-(1-cyanocyclopropyl)-5-[1-[1-methyl-5-[1,2,2,2-tetrafluoro-1-(trifluoromethyl)ethyl]pyrrol-2-yl]pyrazol-4-yl]benzamide |

-continued

| Example No. | Structure | Chemical name |
|---|---|---|
| 2 | 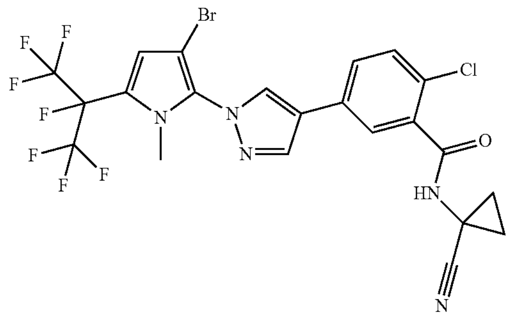 [SMILES: Cn1c(C(F)(C(F)(F)F)C(F)(F)F)cc(Br)c1-n1cc(-c2ccc(Cl)c(C(=O)NC3(C#N)CC3)c2)cn1] | 5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide |
| 3 | 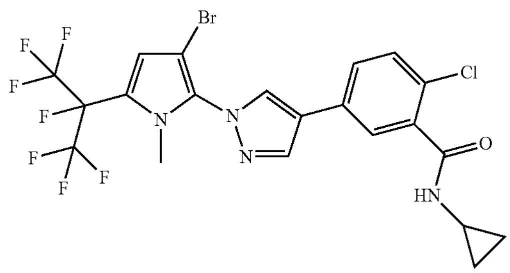 [SMILES: Cn1c(C(F)(C(F)(F)F)C(F)(F)F)cc(Br)c1-n1cc(-c2ccc(Cl)c(C(=O)NC3CC3)c2)cn1] | 5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-benzamide |
| 4 | 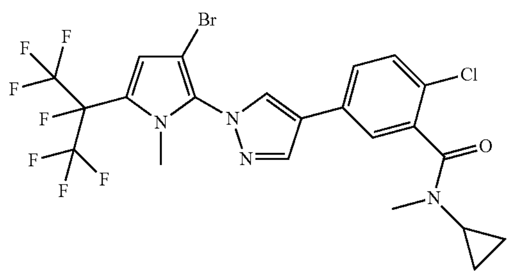 [SMILES: CN(C(=O)c1cc(-c2cnn(-c3c(Br)cc(C(F)(C(F)(F)F)C(F)(F)F)n3C)c2)ccc1Cl)C1CC1] | 5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-N-methyl-benzamide |
| 5 | 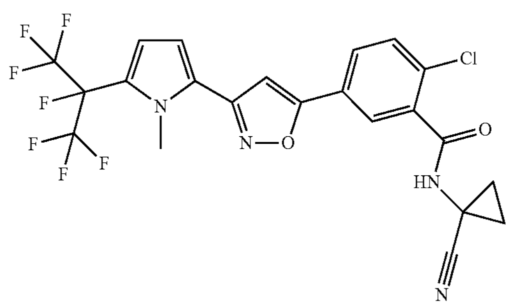 [SMILES: Cn1c(-c2cc(-c3ccc(Cl)c(C(=O)NC4(C#N)CC4)c3)on2)ccc1C(F)(C(F)(F)F)C(F)(F)F] | 2-chloro-N-(1-cyanocyclopropyl)-5-[3-[1-methyl-5-[1,2,2,2-tetrafluoro-1-(trifluoromethyl)ethyl]pyrrol-2-yl]isoxazol-5-yl]benzamide |
| 6 | 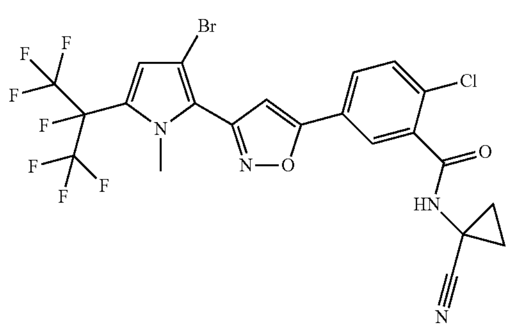 [SMILES: Cn1c(C(F)(C(F)(F)F)C(F)(F)F)cc(Br)c1-c1cc(-c2ccc(Cl)c(C(=O)NC3(C#N)CC3)c2)on1] | 5-[3-[3-bromo-1-methyl-5-[1,2,2,2-tetrafluoro-1-(trifluoromethyl)ethyl]pyrrol-2-yl]isoxazol-5-yl]-2-chloro-N-(1-cyanocyclopropyl)benzamide |

-continued

| Example No. | Structure | Chemical name |
|---|---|---|
| 7 | 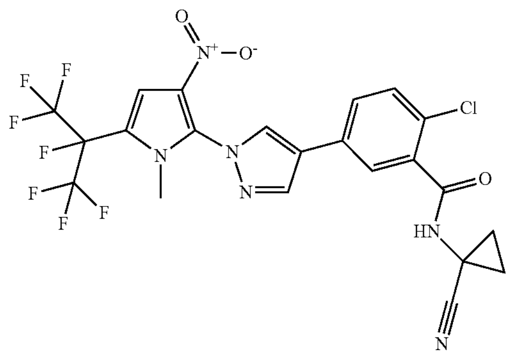 [SMILES: Cn1c(C(F)(C(F)(F)F)C(F)(F)F)cc([N+](=O)[O-])c1-n1cc(-c2ccc(Cl)c(C(=O)NC3(C#N)CC3)c2)cn1] | 2-chloro-N-(1-cyanocyclopropyl)-5-[1-[1-methyl-3-nitro-5-[1,2,2,2-tetrafluoro-1-(trifluoromethyl)ethyl]pyrrol-2-yl]pyrazol-4-yl]benzamide |
| 8 | 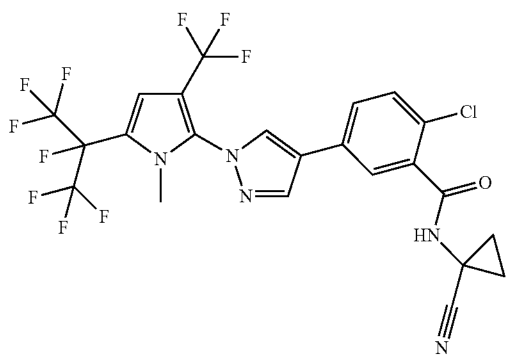 [SMILES: Cn1c(C(F)(C(F)(F)F)C(F)(F)F)cc(C(F)(F)F)c1-n1cc(-c2ccc(Cl)c(C(=O)NC3(C#N)CC3)c2)cn1] | 2-chloro-N-(1-cyanocyclopropyl)-5-[1-[1-methyl-5-[1,2,2,2-tetrafluoro-1-(trifluoromethyl)ethyl]-3-(trifluoromethyl)pyrrol-2-yl]pyrazol-4-yl]benzamide |
| 9 | 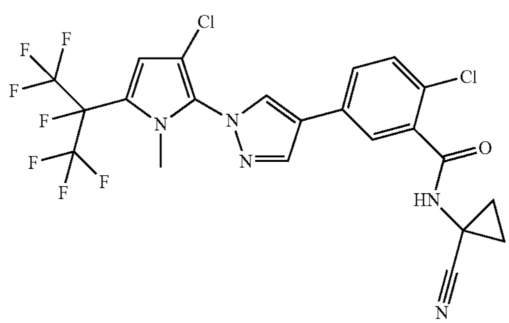 | 2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)benzamide |
| 10 | 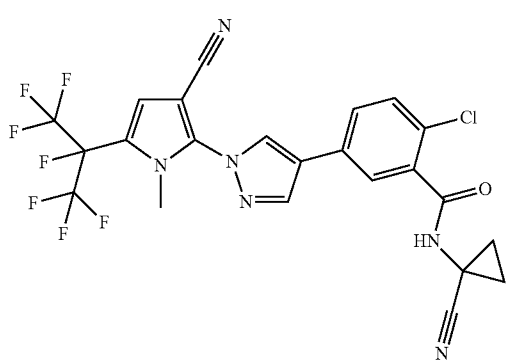 [SMILES: Cn1c(C(F)(C(F)(F)F)C(F)(F)F)cc(C#N)c1-n1cc(-c2ccc(Cl)c(C(=O)NC3(C#N)CC3)c2)cn1] | 2-chloro-N-(1-cyanocyclopropyl)-5-[1-[3-cyano-1-methyl-5-[1,2,2,2-tetrafluoro-1-(trifluoromethyl)ethyl]pyrrol-2-yl]pyrazol-4-yl]benzamide |

-continued

| Example No. | Structure | Chemical name |
|---|---|---|
| 11 | 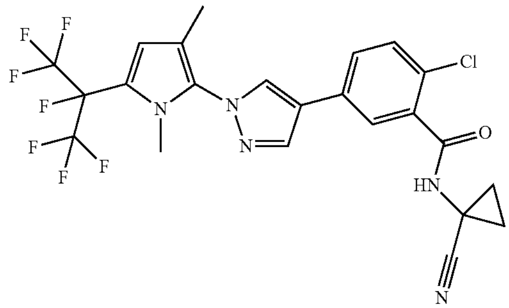 [SMILES: Cc1cc(C(F)(C(F)(F)F)C(F)(F)F)n(C)c1-n1cc(-c2ccc(Cl)c(C(=O)NC3(C#N)CC3)c2)cn1] | 2-chloro-N-(1-cyanocyclopropyl)-5-[1-[1,3-dimethyl-5-[1,2,2,2-tetrafluoro-1-(trifluoromethyl)ethyl]pyrrol-2-yl]pyrazol-4-yl]benzamide |
| 12 | 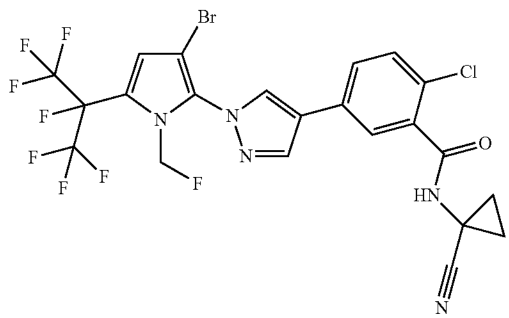 [SMILES: N#CC1(NC(=O)c2cc(-c3cnn(-c4c(Br)cc(C(F)(C(F)(F)F)C(F)(F)F)n4CF)c3)ccc2Cl)CC1] | 5-[1-[3-bromo-1-(fluoromethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide |
| 13 | 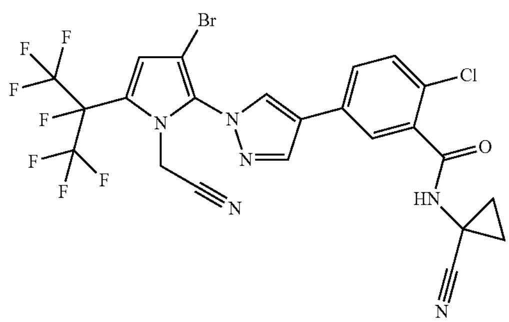 [SMILES: N#CCn1c(C(F)(C(F)(F)F)C(F)(F)F)cc(Br)c1-n1cc(-c2ccc(Cl)c(C(=O)NC3(C#N)CC3)c2)cn1] | 5-[1-[3-bromo-1-(cyanomethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide |
| 14 | 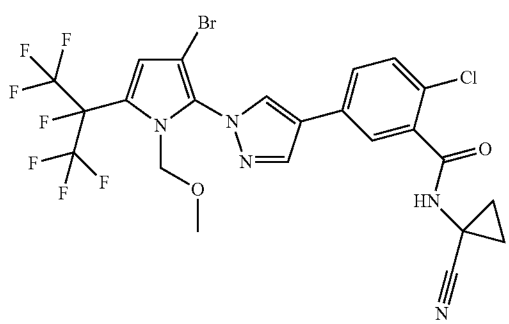 [SMILES: COCn1c(C(F)(C(F)(F)F)C(F)(F)F)cc(Br)c1-n1cc(-c2ccc(Cl)c(C(=O)NC3(C#N)CC3)c2)cn1] | 5-[1-[3-bromo-1-(methoxymethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide |
| 15 | 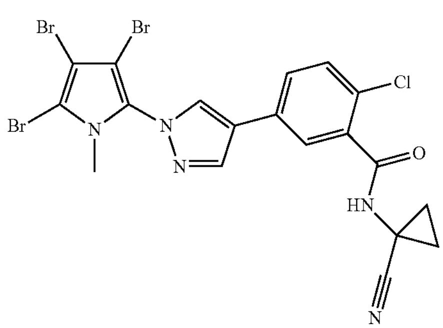 [SMILES: Cn1c(Br)c(Br)c(Br)c1-n1cc(-c2ccc(Cl)c(C(=O)NC3(C#N)CC3)c2)cn1] | 2-chloro-N-(1-cyanocyclopropyl)-5-[1-(3,4,5-tribromo-1-methyl-pyrrol-2-yl)pyrazol-4-yl]benzamide |

| Example No. | Structure | Chemical name |
|---|---|---|
| 16 | 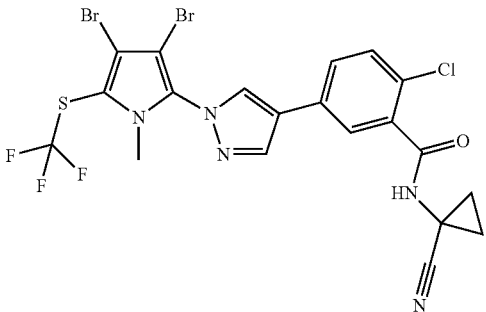 [SMILES: Cn1c(SC(F)(F)F)c(Br)c(Br)c1-n1cc(-c2ccc(Cl)c(C(=O)NC3(C#N)CC3)c2)cn1] | 2-chloro-N-(1-cyanocyclopropyl)-5-[1-[3,4-dibromo-1-methyl-5-(trifluoromethylsulfanyl)pyrrol-2-yl]pyrazol-4-yl]benzamide |
| 17 | 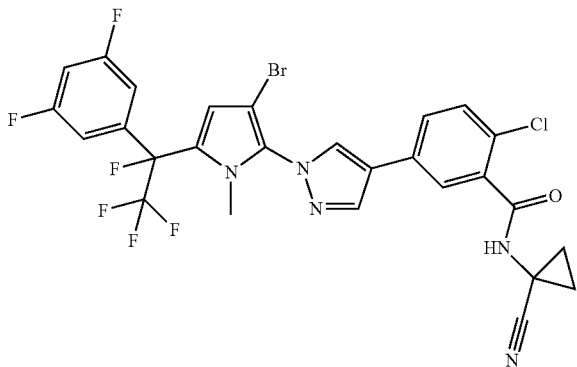 [SMILES: Cn1c(C(F)(c2cc(F)cc(F)c2)C(F)(F)F)cc(Br)c1-n1cc(-c2ccc(Cl)c(C(=O)NC3(C#N)CC3)c2)cn1] | 5-[1-[3-bromo-5-[1-(3,5-difluorophenyl)-1,2,2,2-tetrafluoro-ethyl]-1-methyl-pyrrol-2-yl]pyrazol-4-yl]-2-chloro-N-(1-cyanocyclopropyl)benzamide |
| 18 | 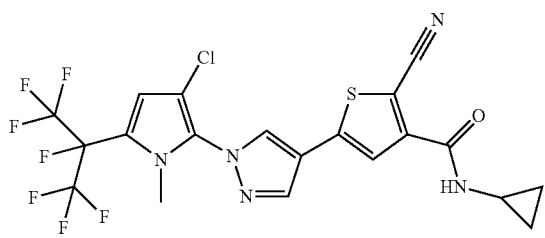 [SMILES: Cn1c(C(F)(C(F)(F)F)C(F)(F)F)cc(Cl)c1-n1cc(-c2cc(C(=O)NC3CC3)c(C#N)s2)cn1] | 5-[1-[3-chloro-1-methyl-5-[1,2,2,2-tetrafluoro-1-(trifluoromethyl)ethyl]pyrrol-2-yl]pyrazol-4-yl]-2-cyano-N-cyclopropyl-thiophene-3-carboxamide |
| 19 | 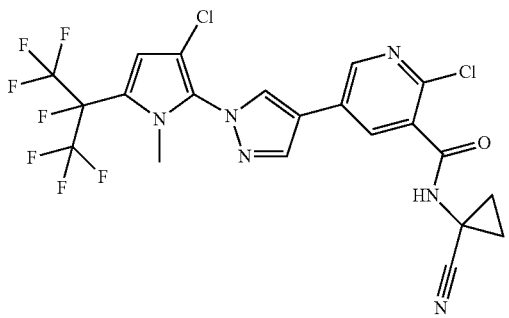 [SMILES: Cn1c(C(F)(C(F)(F)F)C(F)(F)F)cc(Cl)c1-n1cc(-c2cnc(Cl)c(C(=O)NC3(C#N)CC3)c2)cn1] | 2-chloro-5-[1-[3-chloro-1-methyl-5-[1,2,2,2-tetrafluoro-1-(trifluoromethyl)ethyl]pyrrol-2-yl]pyrazol-4-yl]-(1-cyanocyclopropyl)pyridine-3-carboxamide |
| 20 | 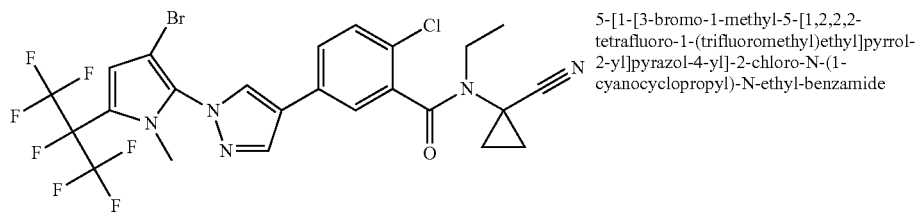 | 5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)-N-ethyl-benzamide |

-continued

| Example No. | Structure | Chemical name |
|---|---|---|
| 21 | 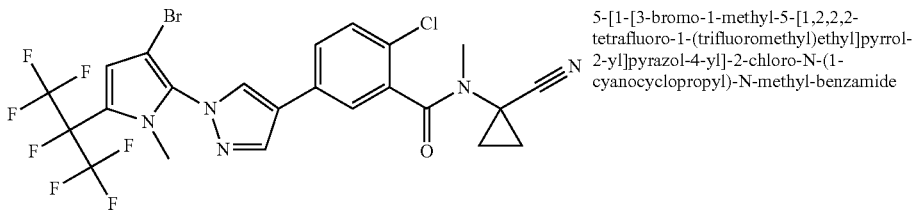 | 5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)-N-methyl-benzamide |
| 22 | 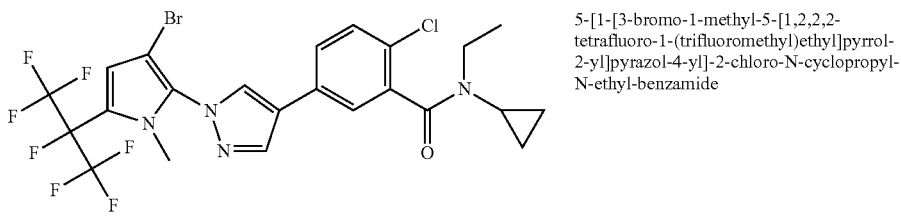 | 5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-N-ethyl-benzamide |
| 23 | 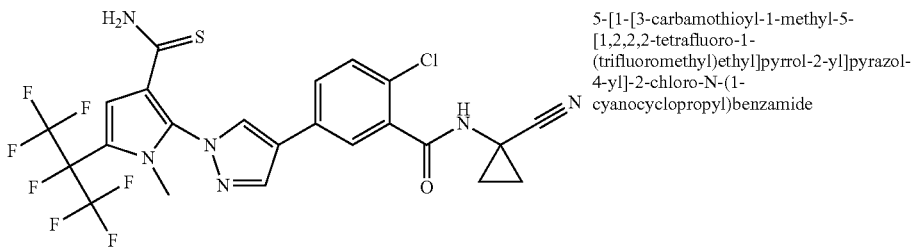 | 5-[1-[3-carbamothioyl-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide |
| 24 | 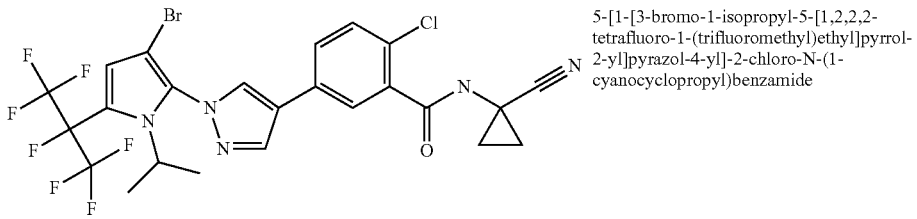 | 5-[1-[3-bromo-1-isopropyl-5-[1,2,2,2-tetrafluoro-1-(trifluoromethyl)ethyl]pyrrol-2-yl]pyrazol-4-yl]-2-chloro-N-(1-cyanocyclopropyl)benzamide |
| 25 | 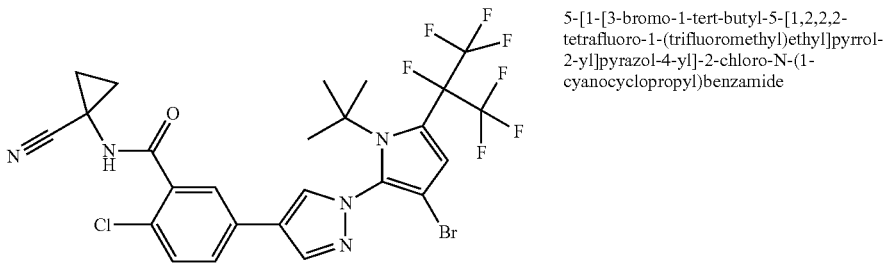 | 5-[1-[3-bromo-1-tert-butyl-5-[1,2,2,2-tetrafluoro-1-(trifluoromethyl)ethyl]pyrrol-2-yl]pyrazol-4-yl]-2-chloro-N-(1-cyanocyclopropyl)benzamide |
| 26 | 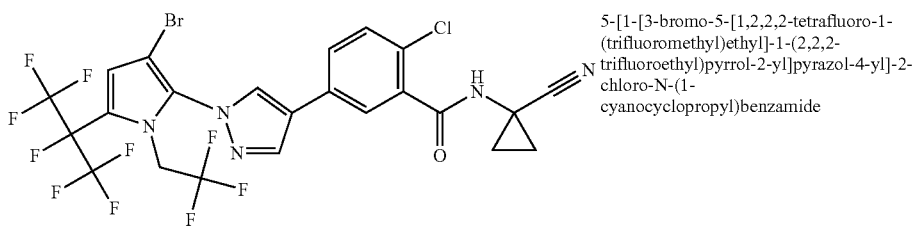 | 5-[1-[3-bromo-5-[1,2,2,2-tetrafluoro-1-(trifluoromethyl)ethyl]-1-(2,2,2-trifluoroethyl)pyrrol-2-yl]pyrazol-4-yl]-2-chloro-N-(1-cyanocyclopropyl)benzamide |

-continued

| Example No. | Structure | Chemical name |
|---|---|---|
| 27 | 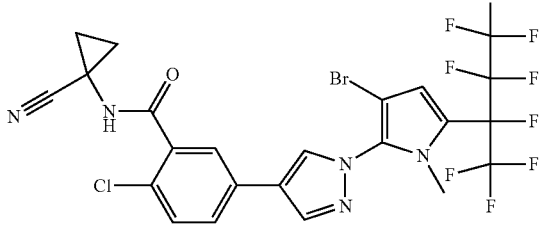 | 5-[1-[3-bromo-5-[1,2,2,3,3,3-hexafluoro-1-(trifluoromethyl)propyl]-1-methyl-pyrrol-2-yl]pyrazol-4-yl]-2-chloro-N-(1-cyanocyclopropyl)benzamide |
| 28 | 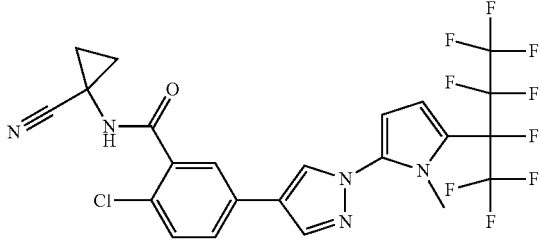 [SMILES: Cn1c(-n2cc(-c3ccc(Cl)c(C(=O)NC4(C#N)CC4)c3)cn2)ccc1C(F)(C(F)(F)F)C(F)(F)C(F)(F)F] | 2-chloro-N-(1-cyanocyclopropyl)-5-[1-[5-[1,2,2,3,3,3-hexafluoro-1-(trifluoromethyl)propyl]-1-methyl-pyrrol-2-yl]pyrazol-4-yl]benzamide |
| 29 | 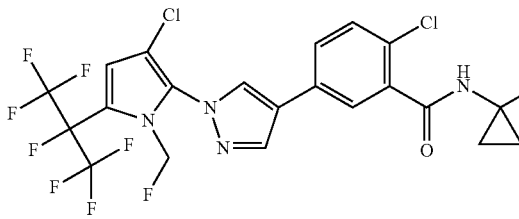 | 2-chloro-5-[1-[3-chloro-1-(fluoromethyl)-5-[1,2,2,2-tetrafluoro-1-(trifluoromethyl)ethyl]pyrrol-2-yl]pyrazol-4-yl]-N-(1-cyanocyclopropyl)benzamide |
| 30 | 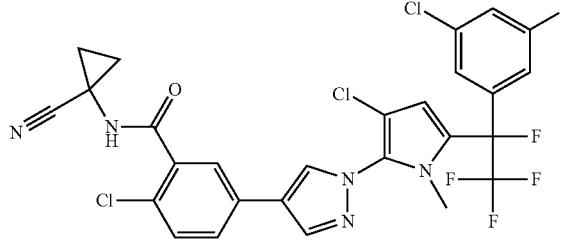 | 2-chloro-5-[1-[3-chloro-5-[1-(3,5-dichlorophenyl)-1,2,2,2-tetrafluoro-ethyl]-1-methyl-pyrrol-2-yl]pyrazol-4-yl]-N-(1-cyanocyclopropyl)benzamide |
| 31 | 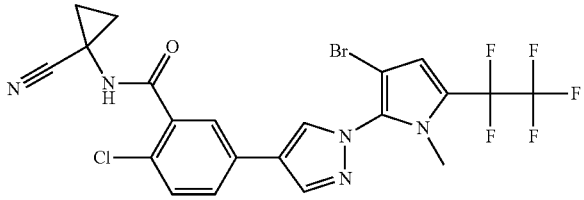 | 5-[1-[3-bromo-1-methyl-5-(1,1,2,2,2-pentafluoroethyl)pyrrol-2-yl]pyrazol-4-yl]-2-chloro-N-(1-cyanocyclopropyl)benzamide |
| 32 | 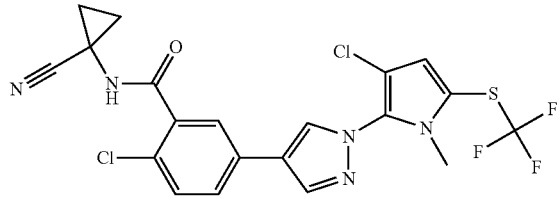 [SMILES: Cn1c(SC(F)(F)F)cc(Cl)c1-n1cc(-c2ccc(Cl)c(C(=O)NC3(C#N)CC3)c2)cn1] | 2-chloro-5-[1-[3-chloro-1-methyl-5-(trifluoromethylsulfanyl)pyrrol-2-yl]pyrazol-4-yl]-N-(1-cyanocyclopropyl)benzamide |

-continued

| Example No. | Structure | Chemical name |
|---|---|---|
| 33 | 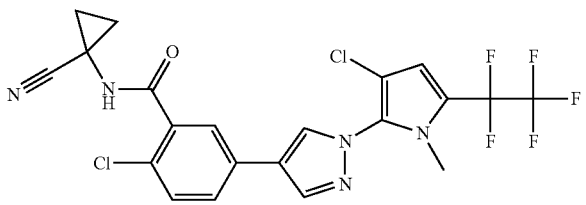 [SMILES: Cn1c(C(F)(F)C(F)(F)F)cc(Cl)c1-n1cc(-c2ccc(Cl)c(C(=O)NC3(C#N)CC3)c2)cn1] | 2-chloro-5-[1-[3-chloro-1-methyl-5-(1,1,2,2,2-pentafluoroethyl)pyrrol-2-yl]pyrazol-4-yl]-(1-cyanocyclopropyl)benzamide |
| 34 | 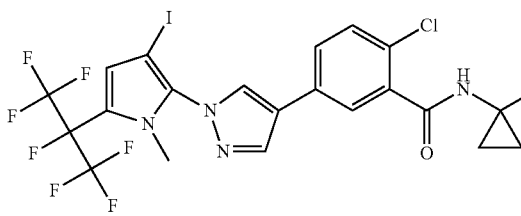 | 2-chloro-N-(1-cyanocyclopropyl)-5-[1-[3-iodo-1-methyl-5-[1,2,2,2-tetrafluoro-1-(trifluoromethyl)ethyl]pyrrol-2-yl]pyrazol-4-yl]benzamide |
| 35 | 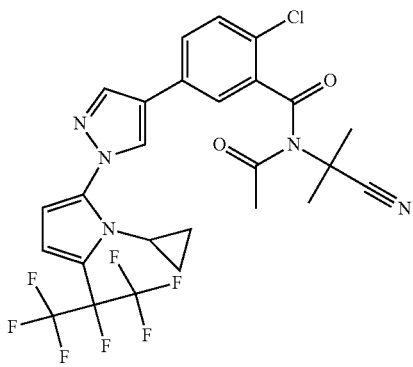 [SMILES: CC(=O)N(C(=O)c1cc(-c2cnn(-c3ccc(C(F)(C(F)(F)F)C(F)(F)F)n3C3CC3)c2)ccc1Cl)C(C)(C)C#N] | N-acetyl-2-chloro-N-(1-cyano-1-methyl-ethyl)-5-[1-[1-cyclopropyl-5-[1,2,2,2-tetrafluoro-1-(trifluoromethyl)ethyl]pyrrol-2-yl]pyrazol-4-yl]benzamide |
| 36 | 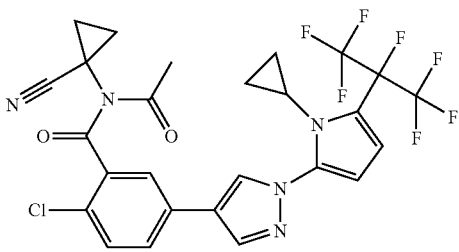 [SMILES: CC(=O)N(C(=O)c1cc(-c2cnn(-c3ccc(C(F)(C(F)(F)F)C(F)(F)F)n3C3CC3)c2)ccc1Cl)C1(C#N)CC1] | N-acetyl-2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]benzamide |
| 37 | 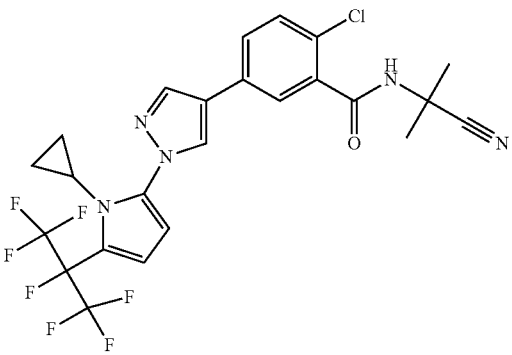 [SMILES: CC(C)(C#N)NC(=O)c1cc(-c2cnn(-c3ccc(C(F)(C(F)(F)F)C(F)(F)F)n3C3CC3)c2)ccc1Cl] | 2-chloro-N-(1-cyano-1-methyl-ethyl)-5-[1-[1-cyclopropyl-5-[1,2,2,2-tetrafluoro-1-(trifluoromethyl)ethyl]pyrrol-2-yl]pyrazol-4-yl]benzamide |

-continued

| Example No. | Structure | Chemical name |
|---|---|---|
| 38 | 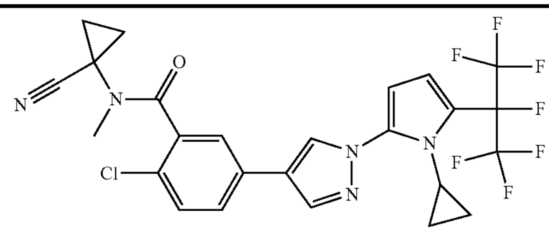 | 2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]-N-methyl-benzamide |
| 39 | 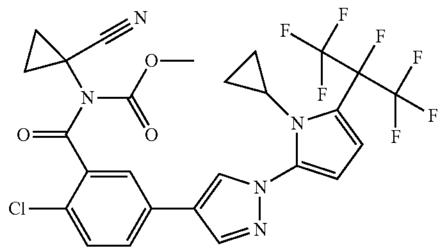 [SMILES: COC(=O)N(C(=O)c1cc(-c2cnn(-c3ccc(C(F)(C(F)(F)F)C(F)(F)F)n3C3CC3)c2)ccc1Cl)C1(C#N)CC1] | methyl N-[2-chloro-5-[1-[1-cyclopropyl-5-[1,2,2,2-tetrafluoro-1-(trifluoromethyl)ethyl]pyrrol-2-yl]pyrazol-4-yl]benzoyl]-N-(1-cyanocyclopropyl)carbamate |
| 40 | 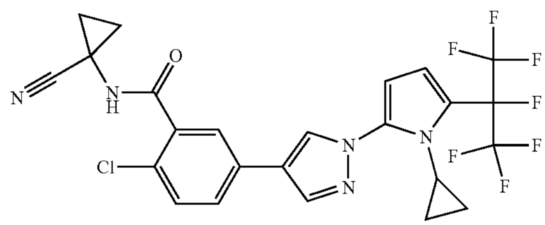 [SMILES: N#CC1(NC(=O)c2cc(-c3cnn(-c4ccc(C(F)(C(F)(F)F)C(F)(F)F)n4C4CC4)c3)ccc2Cl)CC1] | 2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]benzamide |
| 41 | 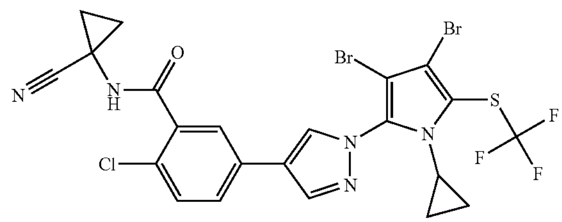 [SMILES: N#CC1(NC(=O)c2cc(-c3cnn(-c4c(Br)c(Br)c(SC(F)(F)F)n4C4CC4)c3)ccc2Cl)CC1] | 2-chloro-N-(1-cyanocyclopropyl)-5-[1-[3,4-dibromo-1-cyclopropyl-5-(trifluoromethylsulfanyl)pyrrol-2-yl]pyrazol-4-yl]benzamide |
| 42 | 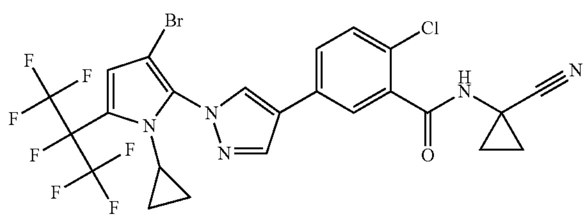 [SMILES: N#CC1(NC(=O)c2cc(-c3cnn(-c4c(Br)cc(C(F)(C(F)(F)F)C(F)(F)F)n4C4CC4)c3)ccc2Cl)CC1] | 5-[1-[3-bromo-1-cyclopropyl-5-[1,2,2,2-tetrafluoro-1-(trifluoromethyl)ethyl]pyrrol-2-yl]pyrazol-4-yl]-2-chloro-N-(1-cyanocyclopropyl)benzamide |

Definitions:

The term "Alkyl" as used herein—in isolation or as part of a chemical group—represents straight-chain or branched hydrocarbons, preferably with 1 bis 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Alkyl groups with 1 to 4 carbon atoms are preferred, for example methyl, ethyl, n-propyl, isopropyl, n-butyl, isobutyl, s-butyl or t-butyl.

The term "Alkenyl"—in isolation or as part of a chemical group—represents straight-chain or branched hydrocarbons, preferably with 2 bis 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Alkenyl groups with 2 to 4 carbon atoms are preferred, for example 2-propenyl, 2-butenyl or 1-methyl-2-propenyl.

The term "Alkynyl"—in isolation or as part of a chemical group—represents straight-chain or branched hydrocarbons, preferably with 2 bis 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Alkynyls with 2 to 4 carbon atoms are preferred, for example ethynyl, 2-propynyl or 2-butynyl-2-propenyl.

The term "cycloalkyl"—in isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl.

Cycloalkyls with 3, 4, 5, 6 or 7 carbon atoms are preferred, for example cyclopropyl or cyclobutyl.

The term "heterocycloalkyl"—in isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl, wherein one or more of the ring atoms, preferably 1 to 4, more preferably 1, 2 or 3 of the ring atoms are independently selected from N, O, S, P, B, Si and Se, more preferably N, O and S, wherein no O atoms can be located next to each other.

The term "Alkylcycloalkyl" represents mono-, bi-oder tricyclic alkylcycloalkyl, preferably with 4 to 10 or 4 to 7 carbon atoms, for example ethylcyclopropyl, isopropylcyclobutyl, 3-methylcyclopentyl and 4-methyl-cyclohexyl. Alkylcycloalkyls with 4, 5 or 7 carbon atoms are preferred, for example ethylcyclopropyl or 4-methyl-cyclohexyl.

The term "cycloalkylalkyl" represents mono, bi- or tricyclic cycloalkylalkyls, preferably 4 to 10 or 4 to 7 carbon atoms, for example cyclopropylmethyl, cyclobutylmethyl, cyclopentylmethyl, cyclohexylmethyl and cyclopentylethyl. Cycloalkylalkyls with 4, 5 or 7 carbon atoms are preferred, for example cyclopropylmethyl or cyclobutylmethyl.

The term "halogen" or "halo" represents fluoro, chloro, bromo or iodo, particularly fluoro, chloro or bromo. The chemical groups which are substituted with halogen, for example haloalkyl, halocycloalkyl, haloalkyloxy, haloalkylsulfanyl, haloalkylsulfinyl or haloalkylsulfonyl are substituted one or up to the maximum number of substituents with halogen. If "alkyl", "alkenyl" or "alkynyl" are substituted with halogen, the halogen atoms can be the same or different and can be bound at the same carbon atom or different carbon atoms.

The term "halocycloalkyl" represents mono-, bi- or tricyclic halocycloalkyl, preferably with 3 to 10 carbon atoms, for example 1-fluoro-cyclopropyl, 2-fluoro-cyclopropyl or 1-fluoro-cyclobutyl. Preferred halocycloalkyl mit 3, 5 oder 7 carbon atoms.

The term "haloalkyl", "haloalkenyl" or "haloalkynyl" represents alkyls, alkenyls or alkynyls substituted with halogen, preferably with 1 to 9 halogen atoms that are the same or different, for example monohaloalkyls (=monohaloalkyl) like $CH_2CH_2Cl$, $CH_2CH_2F$, $CHClCH_3$, $CHFCH_3$, $CH_2Cl$, $CH_2F$; perhaloalkyls like $CCl_3$ or $CF_3$ or $CF_2CF_3$; polyhaloalkyls like $CHF_2$, $CH_2F$, $CH_2CHFCl$, $CF_2CF_2H$, $CH_2CF_3$. The same applies for haloalkenyl and other groups substituted by halogen.

Examples of haloalkoxy are for example $OCF_3$, $OCHF_2$, $OCH_2F$, $OCF_2CF_3$, $OCH_2CF_3$, $OCF_3$, $OCHF_2$, $OCH_2F$, $OCF_2CF_3$, $OCH_2CF_3$.

Further examples of haloalkyls are trichloromethyl, chlorodifluoromethyl, dichlorofluoromethyl, 1-fluoroethyl, 2-fluoroethyl, 2,2-difluoroethyl, 2,2,2-trifluorethyl, 2,2,2-trichloroethyl, 2-chloro-2,2-difluoroethyl, pentafluorethyl and pentafluoro-t-butyl.

Haloalkyls having 1 to 4 carbon atoms and 1 to 9, preferably 1 to 5 of the same or different halogen atoms selected from fluoro, chloro or bromo, are preferred.

Haloalkyls having 1 or 2 carbon atoms and 1 to 5 gleichen of the same or different halogen atoms selected from fluoro or chloro, for example difluoromethyl, trifluoromethyl or 2,2-difluoroethyl, are particularly preferred.

The term "hydroxyalkyl" represents straight or branched chain alcohols, preferably with 1 to 6 carbon atoms, for example methanol, ethanol, n-propanol, isopropanol, n-butanol, isobutanol, s-butanol and t-butanol. Hydroxyalkyls having 1 to 4 carbon atoms are preferred.

The term "alkoxy" represents straight or branched chain O-alkyl, preferably having 1 to 6 carbon atoms, for example methoxy, ethoxy, n-propoxy, isopropoxy, n-butoxy, isobutoxy, s-butoxy and t-butoxy. Alkoxy having 1 to 4 carbon atoms are preferred.

The term "haloalkoxy" represents straight or branched chain O-alkyl substituted with halogen, preferably with 1 to 6 carbon atoms, for example difluoromethoxy, trifluoromethoxy, 2,2-difluoroethoxy, 1,1,2,2-tetrafluoroethoxy, 2,2,2-Trifluoroethoxy and 2-Chloro-1,1,2-trifluorethoxy. Haloalkoxy having 1 to 4 carbon atoms are preferred.

The term "alkylsulfanyl" represents straight or branched chain S-alkyl, preferably with 1 to 6 carbon atoms, for example methylthio, ethylthio, n-propylthio, isopropylthio, n-butylthio, isobutylthio, s-butylthio and t-butylthio. Alkylsulfanyl having 1 to 4 carbon atoms are preferred. Examples for haloalkylsulfanyl, i.e. with halogen substituted alkylsulfanyl, are for example difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio.

The term "alkylsulfinyl" represents straight or branched chain alkylsulfinyl, preferably having 1 to 6 carbon atoms, for example methylsulfinyl, ethylsulfinyl, n-propylsulfinyl, isopropylsulfinyl, n-butylsulfinyl, isobutylsulfinyl, s-butylsulfinyl and t-butylsulfinyl.

Alkylsulfinyls having 1 to 4 carbon atoms are preferred.

Examples of haloalkylsulfinyls, i.e. with halogen substituted alkylsulfinyls, are difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl.

The term "alkylsulfonyl" represents straight or branched chain alkylsulfonyl, preferably having 1 to 6 carbon atoms, for example methylsulfonyl, ethylsulfonyl, n-propylsulfonyl, isopropylsulfonyl, n-butylsulfonyl, isobutylsulfonyl, s-butylsulfonyl and t-butylsulfonyl.

Alkylsulfonyls having 1 to 4 carbon atoms are preferred.

Examples of haloalkylsulfonyls, i.e. with halogen substituted alkylsulfonyls, are for example difluoromethylsulfonyl, trifluoromethylsulfonyl, trichloromethylsulfonyl, chlorodifluoromethylsulfonyl, 1-fluoroethylsulfonyl, 2-fluoroethylsulfonyl, 2,2-difluoroethylsulfonyl, 1,1,2,2-tetrafluoroethylsulfonyl, 2,2,2-trifluoroethylsulfonyl and 2-chloro-1,1,2-trifluroethylsulfonyl.

The term "alkylcarbonyl" represents straight or branched chain alkyl-C(=O), preferably having 2 to 7 carbon atoms, for example methylcarbonyl, ethylcarbonyl, n-propylcarbonyl, isopropylcarbonyl, s-butylcarbonyl and t-butylcarbonyl.

Alkylcarbonyls having 1 to 4 carbon atoms are preferred.

The term "cycloalkylcarbonyl" represents cycloalkyl-carbonyl, preferably 3 to 10 carbon atoms in the cycloalkyl part, for example cyclopropylcarbonyl, cyclobutylcarbonyl, cyclopentylcarbonyl, cyclohexyl-carbonyl, cycloheptyl-carbonyl, cyclooctylcarbonyl, bicyclo[2.2.1]heptyl, bycyclo[2.2.2]octylcarbonyl and adamantylcarbonyl. Cycloalkylcarbonyls having 3, 5 or 7 carbon atoms in the cycloalkyl part are preferred.

The term "alkoxycarbonyl"—in isolation or as part of a chemical group—represents straight or branched chain alkoxycarbonyl, preferably having 1 to 6 carbon atoms or 1 to 4 carbon atoms in the alkoxy part, for example methoxycarbonyl, ethoxycarbonyl, n-propoxycarbonyl, isopropoxycarbonyl, s-butoxycarbonyl and t-butoxycarbonyl.

The term "alkylaminocarbonyl" represents straight or branched chain alkylaminocarbonyl having preferably 1 to 6 carbon atoms or 1 to 4 carbon atoms in the alkyl part, for example methylaminocarbonyl, ethylaminocarbonyl, n-proylaminocarbonyl, isopropyl-aminocarbonyl, s-butylaminocarbonyl and t-butylaminocarbonyl.

The term "N,N-Dialkylamino-carbonyl" "represents straight or branched chain N,N-dialkylaminocarbonyl with preferably) to 6 carbon atoms or 1 to 4 carbon atoms in the alkyl part, for example N,N-Dimethylamino-carbonyl, N,N-diethylamino-carbonyl, N,N-di(n-propylamino)-carbonyl, N,N-di-(isopropylamino)-carbonyl and N,N-di-(s-butylamino)-carbonyl.

The term "aryl" represents a mono-, bi- or polycyclical aromatic system with preferably 6 to 14, more preferably 6 to 10 ring-carbon atoms, for example phenyl, naphthyl, anthryl, phenanthrenyl, preferably phenyl. "Aryl" also represents polycyclic systems, for example tetrahydronaphtyl, indenyl, indanyl, fluorenyl, biphenyl. Arylalkyls are examples of substituted aryls, which may be further substituted with the same or different substituents both at the aryl or alkyl part. Benzyl and 1-phenylethyl are examples of such arylalkyls.

The term "heterocyclyl", "heterocyclic ring" or "heterocyclic ring system" represents a carbocyclic ring system with at least one ring, in which ring at least one carbon atom is replaced by a heteroatom, preferably selected from N, O, S, P, B, Si, Se, and which ring is saturated, unsaturated or partially saturated, and which ring is unsubstituted or substituted with a substituent Z, wherein the connecting bond is located at a ring atom. Unless otherwise defined, the heterocyclic ring has preferably 3 to 9 ring atoms, preferably 3 to 6 ring atoms, and one or more, preferably 1 to 4, more preferably 1, 2 or 3 heteroatoms in the heterocyclic ring, preferably selected from N, O, and S, wherein no O atoms can be located next to each other. The heterocyclic rings normally contain no more than 4 nitrogens, and/or no more than 2 oxygen atoms and/or no more than 2 sulfur atoms. In case that the heterocyclic substituent or the heterocyclic ring are further substituted, it can be further annulated with other heterocyclic rings.

The term "heterocyclic" also includes polycyclic systems, for example 8-aza-bicyclo[3.2.1]octanyl or 1-aza-bicyclo[2.2.1]heptyl.

The term "heterocyclic" also includes spirocyclic systems, for example 1-oxa-5-aza-spiro[2.3]hexyl.

Examples of heterocyclyls are for example piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Particularly important are heteroaryls, i.e. heteroaromatic systems.

The term "heteroaryl" represents heteroaromatic groups, i.e. completely unsaturated aromatic heterocyclic groups, which fall under the above definition of heterocycles. "Heteroaryls" with 5 to 7-membered rings with 1 to 3, preferably 1 or 2 of the same or different heteroatoms selected from N, O, and S. Examples of "heteroaryls" are furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tart-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

A compound according to any one of embodiments 1 to 24 which has at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. A compounds according to any one of embodiments 1 to 24 which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

Compounds according to any one of embodiments 1 to 24 also include hydrates which may be formed during the salt formation.

The compounds according to any one of embodiments 1 to 24 may be made by a variety of methods well known to a person skilled in the art or as shown in Schemes 1-9. Further instructions regarding the preparation may be found in WO2014/122083, WO2012/107434, WO2015/067646, WO2015/067647, WO2015/067648, WO2015/150442, WO2015/193218, WO2010/051926, WO2017/012970, WO2017/055414, WO2017/108569 and WO2017/140771.

Compounds (I) may be prepared, for example, according to Scheme 1-9.

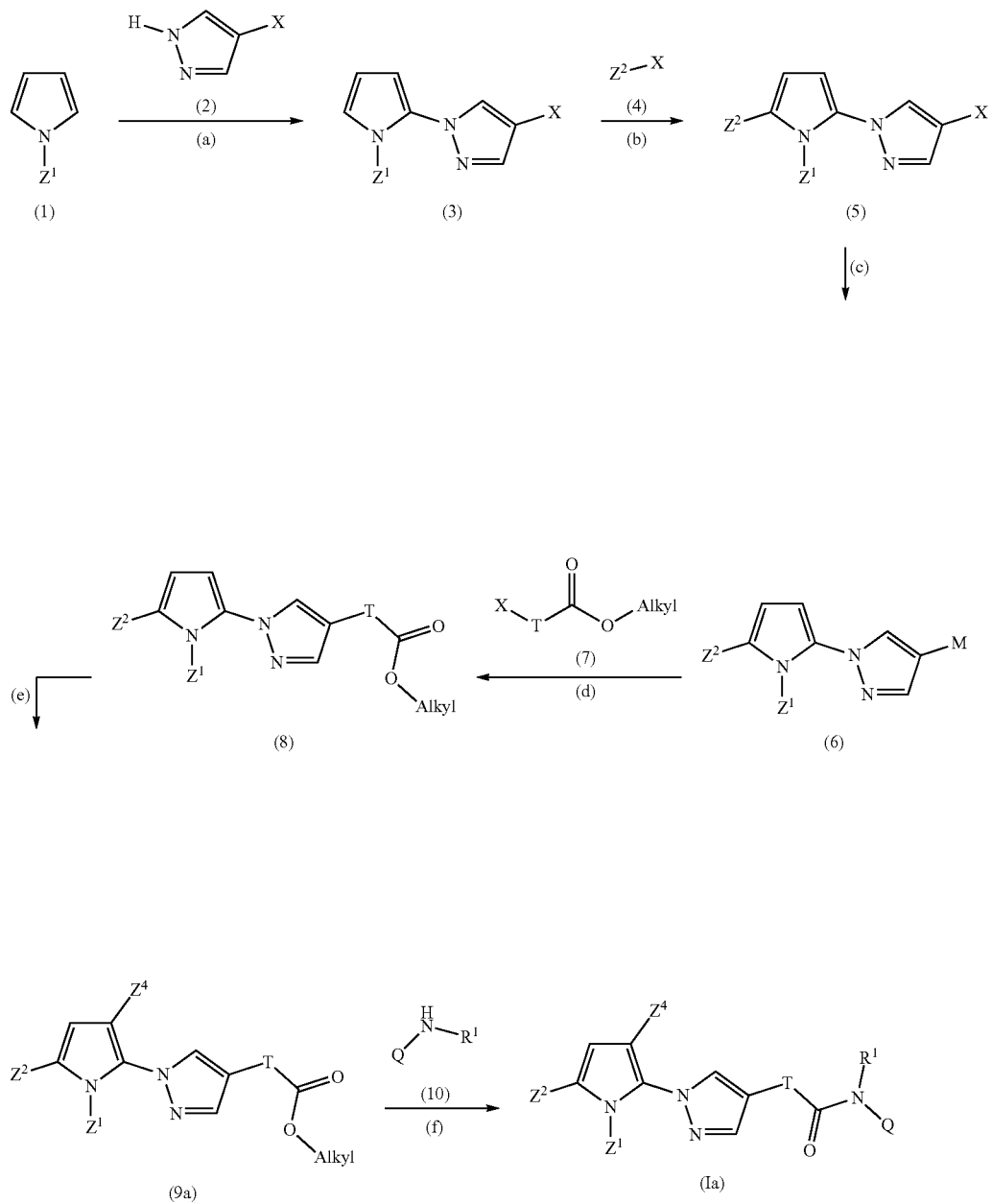

wherein T, Q, $R^1$, $Z^1$, $Z^2$ and $Z^4$ are as defined in any one of embodiments 1 to 24, X is a halogen such as Cl, Br or I, M represents a boronic acid or boronic ester or a zinc chloride or bromide, and alkyl is $C_1$-$C_6$-alkyl.

(a) Compounds of formula (3) can be prepared by reaction of a pyrrole of formula (1) with a pyrazole of formula (2) in the presence of an oxidant such as sodium hypochorite or tertbutylhypochlorite.

(b) Compound of formula (5) can be prepared from compounds of formula (3) wherein X is Br or I by reacting with a compound of formula (4), suitably with a catalytic amount of iron salt such as iron sulfate in the presence of hydrogen peroxide for example.

(c) Compound of formula (6) can be prepared from Compound of formula (5) using known processes from the literature using palladium-catalyzed reactions, such as the Miyaura borylation reaction. For instance, the reactions can be carried out in the presence of a catalyst, such as palladium (II) acetate, palladium(0) tetrakis-triphenylphosphine or bis (triphenylphosphine)palladium(II) dichloride, optionally in the presence of a ligand, such as triphenylphosphine, diphenylphosphinoferrocene ("dppf") and a base, such as sodium carbonate, pyridine, triethylamine, 4-(dimethylamino)-pyridine ("DMAP") or diisopropylethylamine (Hunig's base), in a solvent, such as water, N,N-dimethylformamide, dioxane, methyltetrahydrofuran or tetrahydrofuran, and in the presence of a borylating agent, such as bis(pinacolato)diboron. The reaction is carried out at a temperature of from 50° C. to 200° C., preferably from 100° C. to 150° C. Alternatively, compound of formula (6) can be prepared from compound of formula (5) using known processes from the literature using a metal-halogen exchange reaction followed by a reaction with an electrophile such as trimethylborate, as is described in Org. Lett., 2011, 13, 4479-4481.

(d) In the same manner, compound of formula (8) can be prepared from compound of formula (6) with a compound of formula (7) using known processes from the literature using palladium-catalyzed reactions, such as the Suzuki reaction. The compounds of the general structure (7) are either commercially available or may be prepared by processes known from to the person skilled in the art.

(e) Compound of formula (9a), where $Z^4$ is Cl, Br or I, may be prepared from compound of formula (8) in analogy with literature methods by using a halogenating agent such as N-chlorosuccinimide, N-bromosuccinimide, N-iodosuccinimide, etc.

(f) Compounds of formula (Ia) may be prepared in analogy with literature methods from compounds of formula (9a) via ester cleavage (see for example WO2010/051926 or WO2010/133312) followed by known amide formation methods (see for example WO2010/051926 and WO2010/133312). Compounds of formula (10) are known or may be prepared by processes known from to the person skilled in the art.

Compounds of formula (1), (2), (4), (7) and (10) are commercially available or can be prepared according to methods known to a person skilled in the art.

Scheme 2

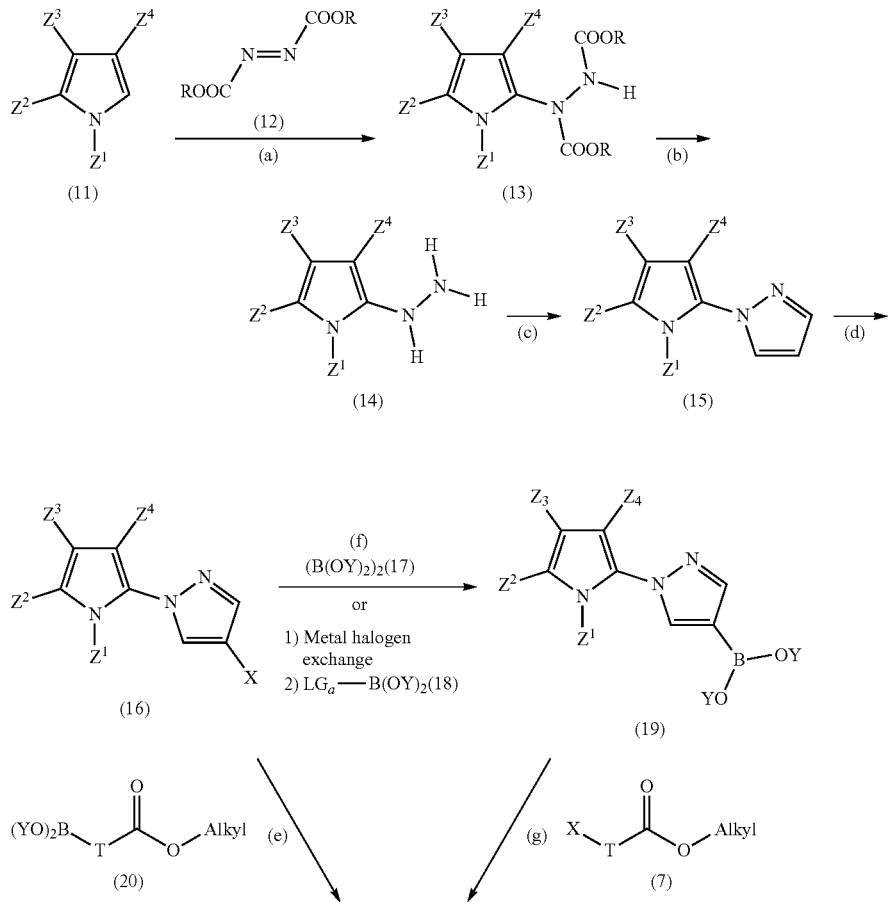

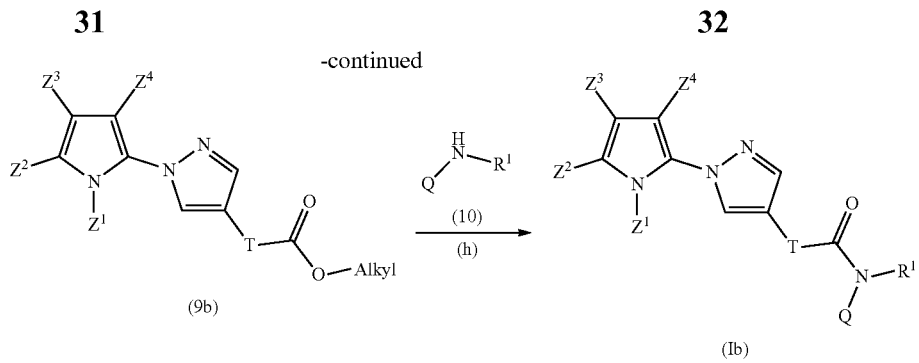

wherein $Z^1$, $Z^2$, $Z^3$, $Z^4$, T, $R^1$ and Q are as defined in any one of the embodiments 1-24.

R represents $C_1$-$C_4$-alkyl (preferably t-Bu), X represents Cl, Br or I, $LG^a$ represents a leaving group like Cl or $C_1$-$C_4$Alkoxy, Alkyl is $C_1$-$C_6$-alkyl and Y is hydrogen or $C_1$-$C_6$-alkyl or 2 adjacent Y can be linked to form a cyclic bis boronate ester, for example, $(B(OY)_2)_2$ could be bis (pinacolato)diboron.

(a) Compound of formula (13) can be prepared by reaction of a strong base such as n-butyllithium on compound of formula (11) followed by reaction with an azodicarboxylate of formula (12).

(b) Compound of formula (14) can be prepared by hydrolysis of a ester compound of formula (13) by processes known from to the person skilled in the art.

(c) Compound of formula (15) can be prepared by reaction of compound of formula (14) with 1,1,3,3,tetramethoxypropane in a solvent such as ethanol or toluene. The reaction is carried out at a temperature of from 0° C. to 110° C.

(d) Compound of formula (16) can be prepared in analogy with literature methods by reacting them with halogenating agents such as $Cl_2$, $Br_2$, $I_2$, N-chlorosuccinimide, N-bromosuccinimide, N-iodosuccinimide, etc.

(e) Compound of formula (9b) may be prepared from compound of formula (16) and a boronic acid or ester of formula (20) by known processes from the literature using palladium-catalyzed reactions, as described in scheme 1.

(f) Compound of formula (16) may also be converted first into boronic acid or ester of formula (19) either by palladium-catalyzed reactions using $(B(OY)_2)_2$ of formula (17) or may be prepared by performing a halogen-metal exchange, for examples using with n-butyllithium, in order to prepare the organolithium reagent, followed by its reaction with an electrophile $LG_a$-$B(OY)_2$ of formula (18), in a suitable solvent, such as diethyl ether, diisopropyl ether, tert-butyl methyl ether, methyltetrahydrofuran or tetrahydrofuran. The reaction is carried out at a temperature of from −80° C. to 60° C., preferably from −20° C. to 40° C.

(g) Compound of formula (19) may then be converted in compound of formula (9b) with a compound (7) using palladium-catalyzed reactions, as described in step (e)).

(h) Compounds of formula (Ib) may be prepared in analogy with literature methods from compounds of formula (9b) via ester cleavage (see for example WO2010/051926 or WO2010/133312) followed by known amide formation methods (see for example WO2010/051926 and WO2010/133312). Compounds of formula (11) are known or maybe prepared according to known methods.

Compounds of formula (12), (17), (18), (7), (20) and (10) are commercially available or may be prepared according to known methods.

Scheme 3

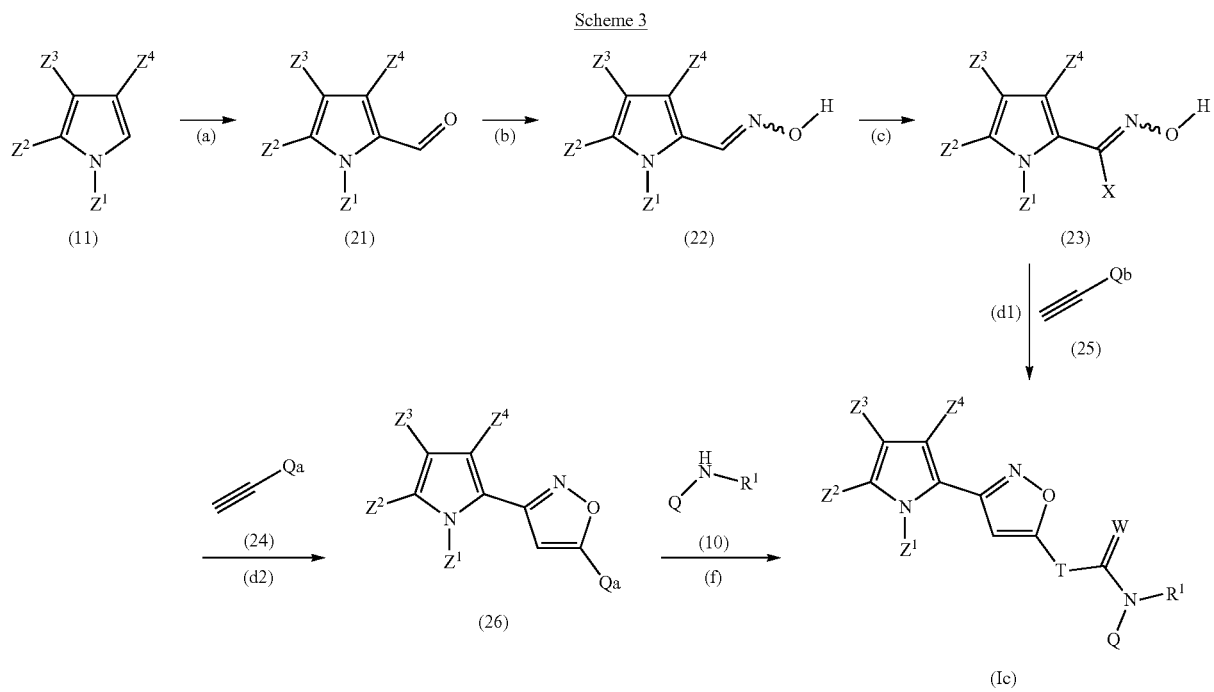

wherein $Z^1$, $Z^2$, $Z^3$, $Z^4$, T, W, $R^1$, $R^2$, A, $R^3$ and Q are as defined in any one of the embodiments 1-24, $R^a$ represents an $C_1$-$C_4$-alkyl, X represents Cl, Br or I, A is N or C—H, Qa can be the following groups:

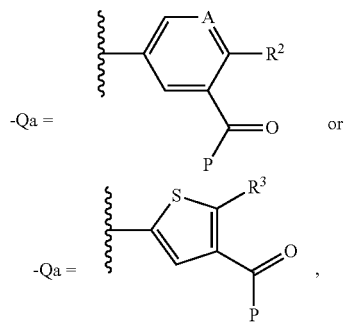

wherein P is OH or $C_1$-$C_6$alkoxy and Qb can be the following groups:

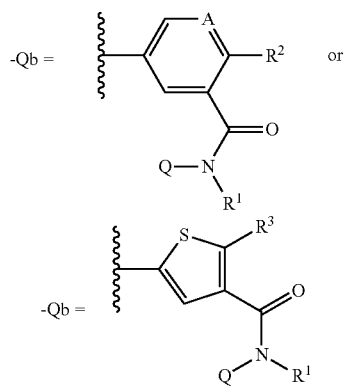

(a) Compound of formula (21) may be prepared by reaction of a strong base such as n-butyllithium on compound of formula (11) followed by reaction with N,N-dimethylformamide, in a solvent, such as diethyl ether, diisopropyl ether, tert-butyl methyl ether, methyltetrahydrofuran or tetrahydrofuran. The reaction is carried out at a temperature from −80° C. to 60° C., preferably from −80° C. to 25° C.

(b) Compound of formula (22) may be prepared in analogy with literature methods from compound of formula (21). For example, known methods for the preparation of oximes from aldehydes may be used (for example H. Metzger in Houben-Weyl, Band X/4, p. 55 ff, Georg Thieme Verlag Stuttgart, 1968).

(c) Compound of formula (23) wherein X represents Cl, Br or I, may be prepared in analogy with literature methods by reacting them with halogenating agents such as $Cl_2$, $Br_2$, $I_2$, N-chlorosuccinimide, N-bromosuccinimide, N-iodosuccinimide, etc.

The compounds of the general structure (24) and (25) are either commercially available or may be prepared by processes known from to the person skilled in the art, for example using a Sonogashira-type coupling with TMS-acetylene.

(d1) & (d2) Compound of formula (26) and (Ib) may be prepared according to known literature methods by reacting compound of formula (23) with a compound of formula (24) and (25), respectively, in the presence of a base in a suitable solvent and at a suitable temperature (for examples as described in WO2015/067646, p. 145-147).

(f) Compounds of formula (Ib) may be prepared in analogy with literature methods from compounds of formula (26) via ester cleavage (see for example WO2010/051926 or WO2010/133312) followed by known amide formation methods (see for example WO2010/051926 and WO2010/133312). Compounds of formula (10) are either commercially available or maybe prepared according to known methods.

Scheme 4

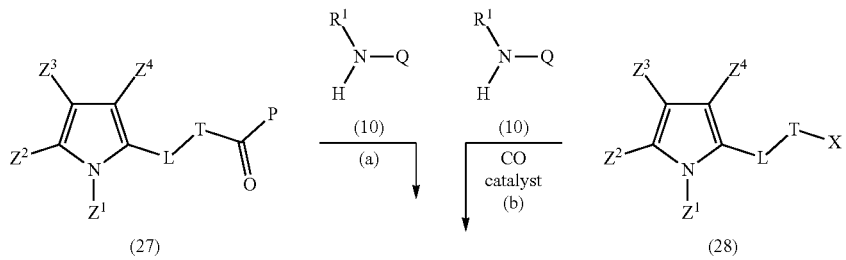

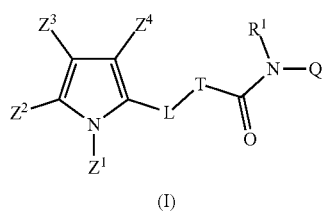

(I)

wherein $Z^1$, $Z^2$, $Z^3$, $Z^4$, L, T, $R^1$ and Q are as defined in any one of the embodiments 1-24.

(a) Compounds of formula (I) may be prepared by reacting a compound of formula (27) wherein P is OH, $C_1$-$C_6$alkoxy, Cl, F or Br, with an amine of formula (10), as shown in Scheme 1. When P is OH such reactions are usually carried out in the presence of a suitable coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP—Cl"), in the presence of a base, and optionally in the presence of a nucleophilic catalyst, such as hydroxybenzotriazole ("HOBT"). When P is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When P is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature.

Acid halides of formula (27), wherein P is Cl, F or Br, may be made from carboxylic acids of formula (27), wherein P is OH, under standard conditions, known from a person skilled in the art.

Carboxylic acids of formula (27), wherein P is OH, may be formed from esters of formula (27), wherein P is $C_1$-$C_6$alkoxy under standard conditions, known from a person skilled in the art.

(b) Compounds of formula (I) may be prepared by reacting a compound of formula (28) wherein X is a leaving group, for example a halogen, such as bromo, with carbon monoxide and an amine of formula (10), in the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

Compounds of formula (27), wherein P is OH, may be prepared by reacting a compound of formula (28) wherein X is a leaving group, for example a triflate or a halogen, such as bromo, with carbon monoxide or potassium formate, in the presence of a catalyst, such as palladium(II) acetate or bis-(triphenylphosphine)palladium(II) dichloride, optionally in the presence of a ligand, such as triphenylphosphine, diphenylphosphinoferrocene ("dppf") and a base, such as sodium carbonate, pyridine, triethylamine, 4-(dimethylamino)-pyridine ("DMAP") or diisopropylethylamine (Hunig's base), in a solvent, such as water, N,N-dimethylformamide, methyltetrahydrofuran or tetrahydrofuran. The reaction is carried out at a temperature of from 50° C. to 200° C., preferably from 100° C. to 150° C. The reaction is carried out at a pressure of CO from 50 to 200 bar, preferably from 100 to 150 bar.

Compounds of formula (27), wherein P is $C_1$-$C_6$alkoxy, may be prepared by reacting a compound of formula (28) wherein X is a leaving group, for example a triflate or a halogen, such as bromo, with carbon monoxide and an alcohol, in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide, methyltetrahydrofuran or tetrahydrofuran. The reaction is carried out at a temperature of from 50° C. to 200° C., preferably from 100° C. to 150° C. The reaction is carried out at a pressure of carbon monoxide from 50 to 200 bar, preferably from 100 to 150 bar.

Alternatively, compounds of formula (27), wherein P is OH, may be prepared by reacting a compound of formula (28) wherein X is a halogen, such as bromo, with magnesium or butyllithium, in order to prepare the intermediate Grignard reagent or respectively the organolithium reagent, followed by its reaction with carbon dioxide, in a solvent, such as diethyl ether, diisopropyl ether, tert-butyl methyl ether, methyltetrahydrofuran or tetrahydrofuran. The reaction is carried out at a temperature of from −80° C. to 60° C., preferably from −20° C. to 40° C. The preparation of the intermediate Grignard reagent (halogen-metal reactions) can also be performed using isopropylmagnesium chloride, in the presence or absence of alkali salts, such as lithium chloride.

Scheme 5

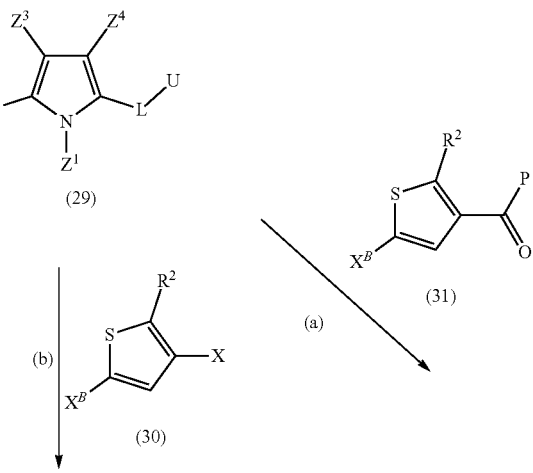

-continued

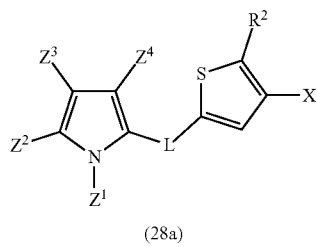
(28a)

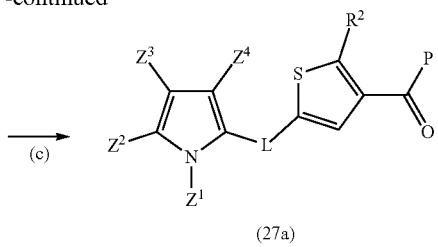
(27a)

wherein $Z^1$, $Z^2$, $Z^3$, $Z^4$, L and $R^2$ are as defined in any one of the embodiments 1-24. X represents Cl, Br or I.

(a) Compounds of formula (27a), wherein P is OH or $C_1$-$C_6$alkoxy, may be prepared by reacting a compound of formula (29) wherein U represents a boronic acid, boronic ester or trifluoroboronate or —SnBu$_3$ or —ZnCl with a compound of formula (31), wherein $X^B$ represents Br, Cl, I or triflate, using known processes from the literature using palladium-catalyzed reactions. For instance, the reactions can be carried out in the presence of a catalyst, such as palladium(II) acetate, palladium(0) tetrakis-triphenylphosphine or bis(triphenylphosphine)palladium(II) dichloride, optionally in the presence of a ligand, such as triphenylphosphine, diphenylphosphinoferrocene ("dppf") and a base, such as sodium carbonate, pyridine, triethylamine, 4-(dimethylamino)-pyridine ("DMAP") or diisopropylethylamine (Hunig's base), in a solvent, such as water, N,N-dimethylformamide, methyltetrahydrofuran or tetrahydrofuran. The reaction is carried out at a temperature of from 50° C. to 200° C., preferably from 100° C. to 150° C.

(b) Compounds of formula (28a) wherein X is a leaving group, for example a triflate or a halogen, such as bromo, may be prepared by reacting a compound of formula (29) wherein U represents a boronic acid, boronic ester or trifluoroboronate or —SnBu$_3$ or —ZnCl with a compound of formula (30), wherein $X^B$ represents bromo, chloro, iodo or triflate, using known processes from the literature using palladium-catalyzed reactions. For instance, the reactions can be carried out in the presence of a catalyst, such as palladium(II) acetate, palladium(0) tetrakis-triphenylphosphine or bis(triphenylphosphine)palladium(II) dichloride, optionally in the presence of a ligand, such as triphenylphosphine, diphenylphosphinoferrocene ("dppf") and a base, such as sodium carbonate, pyridine, triethylamine, 4-(dimethylamino)-pyridine ("DMAP") or diisopropylethylamine (Hunig's base), in a solvent, such as water, N,N-dimethylformamide, methyltetrahydrofuran or tetrahydrofuran. The reaction is carried out at a temperature of from 50° C. to 200° C., preferably from 100° C. to 150° C. The compounds of the general structure (30) and (31) are either commercially available or may be prepared by processes known from to the person skilled in the art. The compounds of the general structure (29) may be prepared as described in the literature (WO2015067647) or as above mentioned in schemes 1 and 2.

Scheme 6

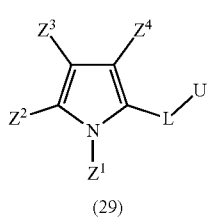
(29)

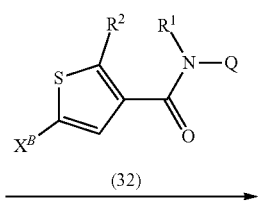
(32)

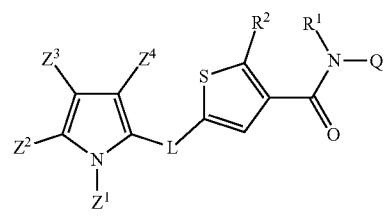
(Id)

wherein $Z^1$, $Z^2$, $Z^3$, $Z^4$, L, $R^1$, Q and $R^2$ are as defined in any one of the embodiments 1-24.

Compounds of formula (Id), may be prepared by reacting a compound of formula (29) wherein U represents a boronic acid, boronic ester or trifluoroboronate or —SnBu$_3$ or —ZnCl with a compound of formula (32), wherein $X^B$ represents bromo, chloro, iodo or triflate, using known processes from the literature using palladium-catalyzed reactions. The compounds of the general structure (32) may be prepared by processes known from to the person skilled in the art.

Scheme 7

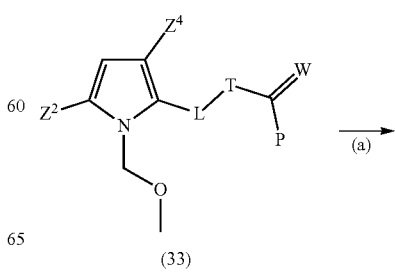
(33)

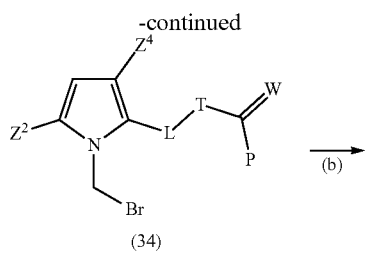

(34)

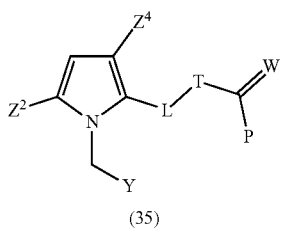

(35)

wherein $Z^2$, $Z^4$, L, T, W, Q and $R^1$ are as defined in any one of the embodiments 1-24, Y represents CN, F, S—$C_1$-$C_4$alkyl, and P is OH, $C_1$-$C_6$alkoxy or $NQR_1$.

(a) Compounds of formula (34) may be prepared by reaction of boron tribromide on compound of formula (33) in a suitable solvent, such as dichloromethane.

(b) Compound of formula (35) may be obtained by reacting a compound of formula (34) with a suitable nucleophile such as potassium fluoride or potassium cyanide.

Scheme 8

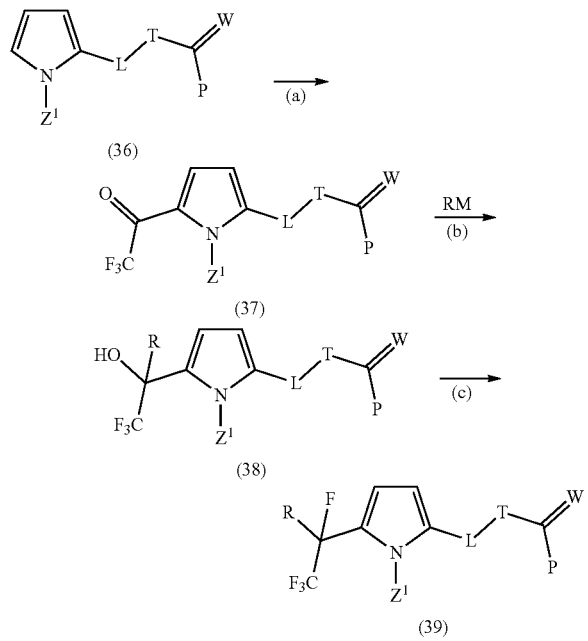

wherein L, T, W, Q, $Z^1$ and $R^1$ are as defined in any one of the embodiments 1-24.

P is OH, $C_1$-$C_6$alkoxy or $NQR_1$.

(a) Compounds of formula (37) may be prepared by reaction of trifluoroacetic anhydride on a compound of formula (36) in a suitable solvent such as pyridine, dichloromethane or benzene (as described for example in Tetrahedron Letters, 50(17), 1934-1938; 2009).

(b) Compounds of formula (38) can be prepared from compounds of formula (37) by treatment with an organometallic species of formula RM wherein M is a lithium or a magnesium salt and wherein R is $C_1$-$C_6$-alkyl, aryl or halogen substituted aryl, in an inert solvent such as diethyl ether or tetrahydrofuran at temperatures of from −80° C. and 40° C.

(c) Compound of formula (39) may be prepared from compound of formula (38) by treatment with an electrophilic fluorinating agent, such as DAST (N,N-Diethylaminosuflur trifluoride) or deoxofluor.

Scheme 9

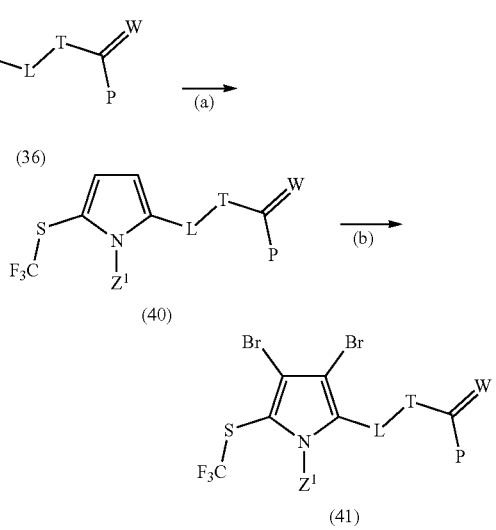

wherein L, T, W, Q and $Z^1$ are as defined in any one of the embodiments 1-24.

P represents P is OH, $C_1$-$C_6$alkoxy or $NQR_1$.

(a) Compound of formula (40) can be prepared from compound of formula (39) by treatment with a sulfur electrophile such as trifluoromethylthiosaccharine.

(b) Compound of formula (41) may be obtained from compound of formula (40) by treatment with a bromine electrophile such as N-bromosuccinimide.

A compound according to any one of embodiments 1 to 24 can be converted in a manner known per se into another compound according to any one of embodiments 1 to 24 by replacing one or more substituents of the starting compound according to any one of embodiments 1 to 24 in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds according to any one of embodiments 1 to 24 can be prepared in a manner known per se. Thus, for example, acid addition salts of compounds according to any one of embodiments 1 to 24 are obtained by treatment with a suitable acid or a suitable ion exchanger reagent and salts with bases are obtained by treatment with a suitable base or with a suitable ion exchanger reagent.

Salts of compounds according to any one of embodiments 1 to 24 can be converted in the customary manner into the free compounds, acid addition salts, for example, by treatment with a suitable basic compound or with a suitable ion exchanger reagent and salts with bases, for example, by treatment with a suitable acid or with a suitable ion exchanger reagent.

Salts of compounds according to any one of embodiments 1 to 24 can be converted in a manner known per se into other salts of compounds according to any one of embodiments 1 to 24, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds according to any one of embodiments 1 to 24, which have salt-forming properties can be obtained in free form or in the form of salts.

The compounds according to any one of embodiments 1 to 24 and, where appropriate, the tautomers thereof, in each case in free form or in salt form, can be present in the form of one of the stereoisomers which are possible or as a mixture of these, for example in the form of pure stereoisomers, such as antipodes and/or diastereomers, or as stereoisomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure stereoisomers and also to all stereoisomer mixtures which are possible and is to be understood in each case in this sense hereinabove and hereinbelow, even when stereochemical details are not mentioned specifically in each case.

Diastereomer mixtures or racemate mixtures of compounds according to any one of embodiments 1 to 24, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable stereoisomer mixtures, but also by generally known methods of diastereoselective or enantioselective synthesis, for example by carrying out the process according to the invention with starting materials of a suitable stereochemistry.

N-oxides can be prepared by reacting a compound according to any one of embodiments 1 to 24 with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective stereoisomer, for example enantiomer or diastereomer, or stereoisomer mixture, for example enantiomer mixture or diastereomer mixture, if the individual components have a different biological activity.

The compounds according to any one of embodiments 1 to 24 and, where appropriate, the tautomers thereof, in each case in free form or in salt form, can, if appropriate, also be obtained in the form of hydrates and/or include other solvents, for example those which may have been used for the crystallization of compounds which are present in solid form.

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, δ ppm, 3 ppm, 1.5 ppm or 0.8 ppm.

The present invention also provides intermediates useful for the preparation of compounds according to any one of embodiments 1 to 24. Certain intermediates are novel and as such form a further aspect of the invention.

One group of novel intermediates are compounds of formula (II)

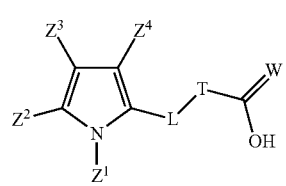

wherein $Z^1$, $Z^2$, $Z^3$, $Z^4$, L, T and W are as defined in any one of embodiments 1 to 24. The preferences for $Z^1$, $Z^2$, $Z^3$, $Z^4$, L, T and W are the same as the preferences set out for the corresponding substituents of a compound according to any one of embodiments 1 to 24.

Another group of novel intermediates are compounds of formula (III)

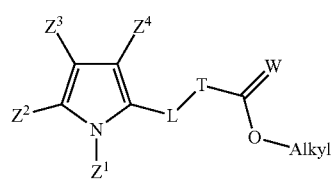

wherein $Z^1$, $Z^2$, $Z^3$, $Z^4$, L, T and W are as defined in any one of embodiments 1 to 24. The preferences for $Z^1$, $Z^2$, $Z^3$, $Z^4$, L, T and W are the same as the preferences set out for the corresponding substituents of a compound according to any one of embodiments 1 to 24. "Alkyl" is $C_1$-$C_6$ alkyl.

Another group of novel intermediates are compounds of formula (IV)

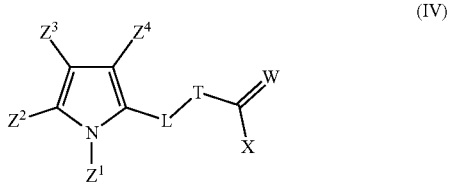

wherein $Z^1$, $Z^2$, $Z^3$, $Z^4$, L, T and W are as defined in any one of embodiments 1 to 24 and X is F or $C_1$. The preferences for $Z^1$, $Z^2$, $Z^3$, $Z^4$, L, T and W are the same as the preferences set out for the corresponding substituents of a compound according to any one of embodiments 1 to 24.

The compounds according to any one of embodiments 1 to 24 are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the above mentioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example, *Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp, *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea pleas*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*; *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Batericera cockerelli*, *Bemisia* spp, *Brachycaudus* spp, *Brevicoryne brassicae*, *Cacopsylla* spp, *Cavariella aegopodii Scop.*, *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*, from the order Hymenoptera, for example,

*Acromyrmex*, *Arge* spp, *Atta* spp., *Cephus* spp., *Diprion* spp., *Diprionidae*, *Gilpinia polytoma*, *Hoplo-campa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

Coptotermes Spp, Corniternes Cumulans, *Incisitermes* Spp, *Macrotermes* Spp, *Mastotermes* Spp, *Microtermes* Spp, *Reticulitermes* Spp.; *Solenopsis* Geminate from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Gra-pholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo* supressalis (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds according to any one of embodiments 1 to 24 may also have activity against the molluscs. Examples of which include, for example, Ampullariidae; *Arion* (*A. ater*, *A. circumscriptus*, *A. hortensis*, *A. rufus*); Bradybaenidae (*Bradybaena fruticum*); Cepaea (*C. hortensis*, *C. Nemoralis*); ochlodina; *Deroceras* (*D. agrestis*, *D. empiricorum*, *D. laeve*, *D. reticulatum*); *Discus* (*D. rotundatus*); Euomphalia; *Galba* (*G. trunculata*); *Helicelia* (*H. itala*, *H.* obvia); Helicidae Helicigona arbustorum); Helicodiscus; Helix (H. aperta); Limax (L. cinereoniger, L. flavus, L. marginatus, L. maximus, L. tenellus); Lymnaea; Milax (M. gagates, M. marginatus, M. sowerbyi); Opeas; Pomacea (P. canaticulata); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins, for example insecticidal proteins from Bacillus cereus or Bacillus popilliae; or insecticidal proteins from Bacillus thuringiensis, such as b-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by b-endotoxins, for example Cry1Ab, Cry1Ac, Cry1F, Cry1 Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from Agrobacterium sp. strain CP4, which imparts tolerance to the herbicide Roundup® (contains glyphosate), and also a Cry1Ab toxin obtained from Bacillus

*thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerant to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In another embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| | *Xylosandrus crassiusculus* | Hardwoods |
| Scolytidae | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, |

TABLE B-continued

Examples of native woodborers of economic importance.

| Family | Species | Host or Crop Infested |
|---|---|---|
| Cerambycidae | Texania campestris | Horsechestnut, Linden, Maple, Mountain-ash, Oak, Pecan, Pear, Peach, Persimmon, Plum, Poplar, Quince, Redbud, Serviceberry, Sycamore, Walnut, Willow Basswood, Beech, Maple, Oak, Sycamore, Willow, Yellow-poplar |
| | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattela germanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon spec. and Dinoderus minutus*, and also hymenopterans such as *Sirex juvencus, Urocerus gigas, Urocerus gigas taignus and Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharine*.

In one aspect, the invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to any one of embodiments 1 to 24 and which are to be selected to suit the intended aims and the prevailing circumstances. In these compositions, the active ingredient is employed in pure form, a solid active ingredient for example in a specific particle size, or, preferably, together with at least one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers.

Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension concentrates:
active ingredient: 5 to 75%, preferably 10 to 50%
water: 94 to 24%, preferably 88 to 30%
surfactant: 1 to 40%, preferably 2 to 30%
Wettable powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

EXAMPLES

The following compounds according to embodiment 1 may be prepared according to the methods described herein or according to known methods.

Experimental

The following examples are intended to illustrate the invention and are not to be construed as being limitations thereon.

Mp means melting point in ° C. H NMR measurements were recorded on a Brucker 400 MHz spectrometer, chemical shifts are given in ppm relevant to a TMS standard. Spectra measured in deuterated solvents as indicated.

LC MS Method A: Standard:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% McOH+0.05% HCOOH, B=Acetonitrile+0.05% HCOOH: gradient: gradient: 0 min 0% B, 100% A; 1.2-1.5 min 100% B; Flow (ml/min) 0.85.

LC MS Method B: Standard Long:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% McOH+0.05% HCOOH, B=Acetonitrile+0.05% HCOOH: gradient: gradient: 0 min 0% B, 100% A; 2.7-3.0 min 100% B; Flow (ml/min) 0.85.

LC MS Method C: Unpolar:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector.

Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 40% B, 60% A; 1.2-1.5 min 100% B; Flow (ml/min) 0.85.

LC MS Method D

ACQUITY SQD Mass Spectrometer from Waters (Single quadrupole mass spectrometer) Ionisation method: Electrospray Polarity: positive ions Capillary (kV) 3.00, Cone (V) 60.00, Extractor (V) 3.00, Source Temperature (° C.) 150, Desolvation Temperature (° C.) 400, Cone Gas Flow (L/Hr) 60, Desolvation Gas Flow (L/Hr) 700

Mass range: 100 to 800 Da

DAD Wavelength range (nm): 210 to 400

Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Example 1: 2-chloro-N-(1-cyanocyclopropyl)-5-[1-[1-methyl-5-[1,2,2,2-tetrafluoro-1-(trifluoromethyl)ethyl]pyrrol-2-yl]pyrazol-4-yl]benzamide a) Preparation of methyl 2-chloro-5-[1-(1-methylpyrrol-2-yl)pyrazol-4-yl]benzoate

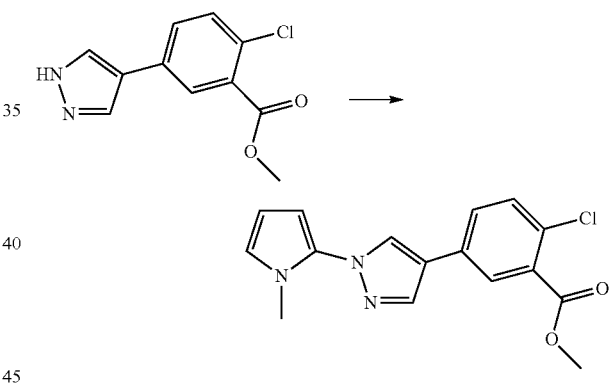

To a stirred mixture of methyl 2-chloro-5-(1H-pyrazol-4-yl)benzoate (3.59 g, 15.2 mmol, may be prepared as described in WO2017/108569), 1-methylpyrrole (3.1 g, 38.0 mmol), sodium bicarbonate (1.27 g, 15.2 mmol), acetonitrile (25 g) and water (10 g) was added sodium hypochlorite 12% solution (28.3 g, 45.6 mmol) dropwise within 30 min while keeping the temperature at 30-35° C. After the addition was completed, the mixture was stirred for 30 min at 30° C.

The reaction mixture was diluted with TBME (30 mL). The organic phase was separated and evaporated to give the crude product which was purified by flash chromatography (silica, cyclohexane/gradient of ethyl acetate from 5 to 20%).

$^1$H NMR (400 MHz, CDCl$_3$) δ ppm 3.55 (s, 3H), 3.97 (s, 3H), 6.16 (m, 1H), 6.22 (m, 1H), 6.63 (dd, J=2.9, 2.2 Hz, 1H), 7.48 (d, J=8.3 Hz, 1H), 7.57 (dd, J=8.3, 2.4 Hz, 1H), 7.86 (d, J=0.7 Hz, 1H), 7.98 (d, J=2.5 Hz, 1H), 8.01 (d, J=0.7 Hz, 1H).

LC-MS (Method A): t$_R$=1.05 min, m/z=316 [M+1].

b) Preparation of Methyl 2-chloro-5-[1-[1-methyl-5-[1,2,2,2-tetrafluoro-1-(trifluoromethyl)ethyl]pyrrol-2-yl]pyrazol-4-yl]benzoate

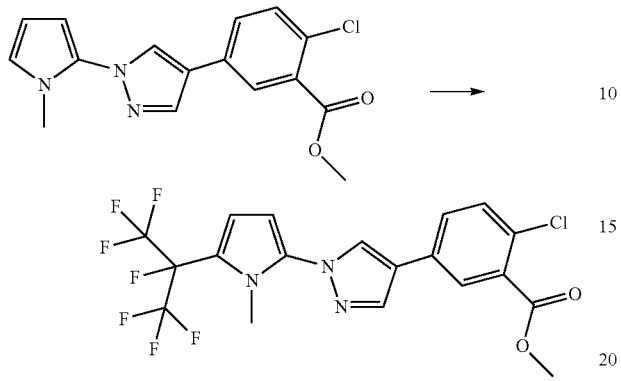

To a stirred mixture of methyl 2-chloro-5-[1-(1-methylpyrrol-2-yl)pyrazol-4-yl]benzoate (0.52 g, 1.65 mmol), 1,1,1,2,3,3,3-heptafluoro-2-iodo-propane (0.55 g, 1.86 mmol), iron(II) sulfate heptahydrate (0.092 g, 0.33 mmol) and dimethyl sulfoxide (3.0 g) was added 30% hydrogen peroxide solution (0.37 g, 3.3 mmol) dropwise within 10 min while keeping the temperature at 55-60° C. The mixture was kept at 60° C. for 5 min and then allowed to cool slowly to room temperature.

The reaction mixture was diluted with water (10 g) and extracted twice with cyclohexane (10+5 mL). The combined extract was washed with water (5 mL), dried over magnesium sulfate and evaporated to give the title compound as a yellow solid.

$^1$H NMR (400 MHz, CDCl$_3$) δ ppm 3.56 (d, J=3.7 Hz, 3H), 3.98 (s, 3H), 6.33 (dd, J=4.2, 1.4 Hz, 1H), 6.58 (m, 1H), 7.50 (d, J=8.3 Hz, 1H), 7.58 (dd, J=8.3, 2.4 Hz, 1H), 7.90 (d, J=0.7 Hz, 1H), 7.99 (d, J=2.2 Hz, 1H), 8.06 (d, J=0.7 Hz, 1H).

$^{19}$F NMR (376 MHz, CDCl$_3$) δ ppm −179.17 (s, 1F), −75.31 (s, 6F).

LC-MS (Method A): t$_R$=1.26 min, m/z=484 [M+1].

c) Preparation of 2-chloro-5-[1-[1-methyl-5-[1,2,2,2-tetrafluoro-1-(trifluoromethyl)ethyl]pyrrol-2-yl]pyrazol-4-yl]benzoic acid

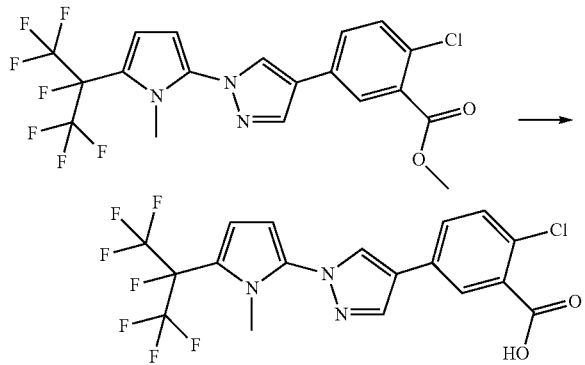

To a stirred solution of Methyl 2-chloro-5-[1-[1-methyl-5-[1,2,2,2-tetrafluoro-1-(trifluoromethyl)ethyl]pyrrol-2-yl]pyrazol-4-yl]benzoate (0.10 g, 0.207 mmol) in a mixture of tetrahydrofurane (3.3 mL) and water (0.8 mL) was added lithium hydroxide monohydrate (0.017 g, 0.41 mmol). The mixture was heated to 40° C. for 4 h. The reaction mixture was acidified with 1N HCl and the product was extracted with ethyl acetate. The organic extract was washed with water than with brine, dried over magnesium sulfate and evaporated to result in a solid material.

LC-MS (Method A): t$_R$=1.13 min, m/z=468 [M−1], 470 [M+1].

d) Preparation of 2-chloro-N-(1-cyanocyclopropyl)-5-[1-[1-methyl-5-[1,2,2,2-tetrafluoro-1-(trifluoromethyl)ethyl]pyrrol-2-yl]pyrazol-4-yl]benzamide

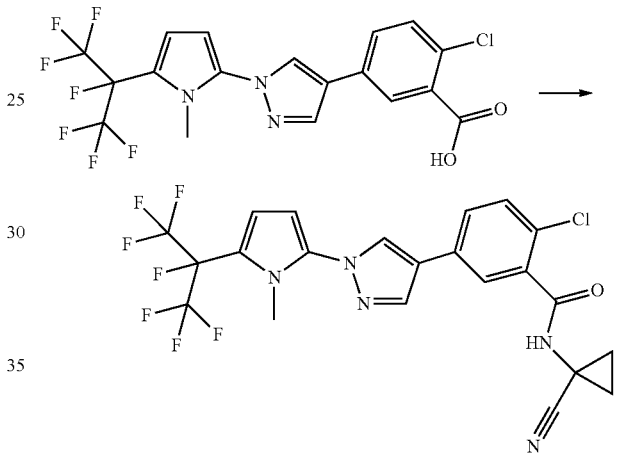

To a stirred solution of 2-chloro-5-[1-[1-methyl-5-[1,2,2,2-tetrafluoro-1-(trifluoromethyl)ethyl]pyrrol-2-yl]pyrazol-4-yl]benzoic acid (0.097 g, 0.207 mmol) in dry dichloromethane (2.0 mL) one drop of dry dimethylformamide was added followed by the addition of oxalyl chloride (0.053 g, 0.41 mmol) at room temperature. The reaction mixture was stirred for 30 min at room temperature and then for 10 min at 40° C. After cooling down to room temperature, the reaction mixture was evaporated to dryness. The remaining acid chloride was dissolved in dry pyridine (2.0 mL) followed by the addition of 1-amino-1-cyano-cyclopropane hydrochloride (0.037 g, 0.31 mmol). The reaction mixture was stirred for 1 h at room temperature. The reaction mixture was evaporated to dryness and the crude product was purified by flash chromatography (silica, cyclohexane/gradient of ethyl acetate from 0 to 40%) to afford a yellow solid.

$^1$H NMR (400 MHz, CDCl$_3$) δ ppm 1.43 (m, 2H), 1.71 (m, 2H), 3.57 (d, J=3.4 Hz, 3H), 6.33 (dd, J=4.3, 1.5 Hz, 1H), 6.58 (m, 1H), 6.89 (s, 1H), 7.45 (d, J=8.4 Hz, 1H), 7.57 (dd, J=8.3, 2.2 Hz, 1H), 7.92 (s, 1H), 7.96 (d, J=2.2 Hz, 1H), 8.07 (s, 1H).

$^{19}$F NMR (376 MHz, CDCl$_3$) δ ppm −179.19 (s, 1F), −75.26 (s, 6F).

LC-MS (Method A): t$_R$=1.12 min, m/z=532 [M−1], 534 [M+1].

Example 2: 5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide a) Preparation of methyl 5-[1-[3-bromo-1-methyl-5-[1,2,2,2-tetrafluoro-1-(trifluoromethyl)ethyl]pyrrol-2-yl]pyrazol-4-yl]-2-chloro-benzoate

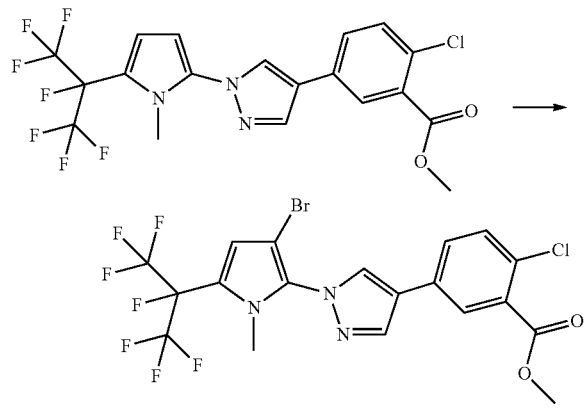

A mixture of Methyl 2-chloro-5-[1-[1-methyl-5-[1,2,2,2-tetrafluoro-1-(trifluoromethyl)ethyl]pyrrol-2-yl]pyrazol-4-yl]benzoate (0.72 g, 1.5 mmol), N-bromosuccinimide (0.28 g, 1.6 mmol) and glacial acetic acid (12 mL) was stirred for 30 min at room temperature. The reaction mixture was evaporated to dryness and the remaining residue was purified by flash chromatography.

$^1$H NMR (400 MHz, CDCl$_3$) δ ppm 3.55 (d, J=3.7 Hz, 3H), 3.98 (s, 3H), 6.64 (s, 1H), 7.52 (d, J=8.3 Hz, 1H), 7.60 (dd, J=8.3, 2.2 Hz, 1H), 7.96 (s, 1H), 8.01 (d, J=2.2 Hz, 1H), 8.12 (s, 1H).

$^{19}$F NMR (376 MHz, CDCl$_3$) δ ppm −180.02 (s, 1F), −75.30 (s, 6F).

LC-MS (Method A): t$_R$=1.29 min, m/z=562 [M−1], 564 [M+1].

b) Preparation of 5-[1-[3-bromo-1-methyl-5-[1,2,2,2-tetrafluoro-1-(trifluoromethyl)ethyl]pyrrol-2-yl]pyrazol-4-yl]-2-chloro-benzoic acid

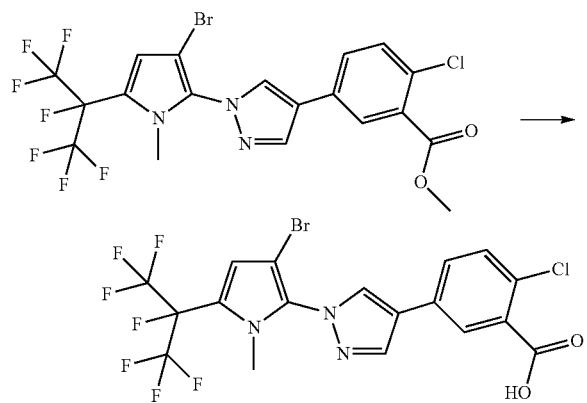

To a stirred solution of methyl 5-[1-[3-bromo-1-methyl-5-[1,2,2,2-tetrafluoro-1-(trifluoromethyl)ethyl]pyrrol-2-yl]pyrazol-4-yl]-2-chloro-benzoate (0.10 g, 0.178 mmol) in a mixture of tetrahydrofurane (3.3 mL) and water (0.8 mL) was added lithium hydroxide monohydrate (0.015 g, 0.36 mmol). The mixture was stirred at room temperature for 18 h. The reaction mixture was acidified with 1N HCl and the product was extracted with ethyl acetate. The organic extract was washed with water than with brine, dried over magnesium sulfate and evaporated to result in a solid.

$^1$H NMR (400 MHz, CDCl$_3$) δ ppm 3.56 (d, J=3.7 Hz, 3H), 6.65 (m, 1H), 7.55 (d, J=8.4 Hz, 1H), 7.66 (dd, J=8.4, 2.2 Hz, 1H), 7.97 (s, 1H), 8.14 (s, 1H), 8.17 (d, J=2.2 Hz, 1H).

$^{19}$F NMR (376 MHz, CDCl$_3$) δ ppm −180.02 (s, 1F), −75.32 (s, 6F).

LC-MS (Method A): t$_R$=1.16 min, m/z=548 [M−1], 550 [M+1].

c) 5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide

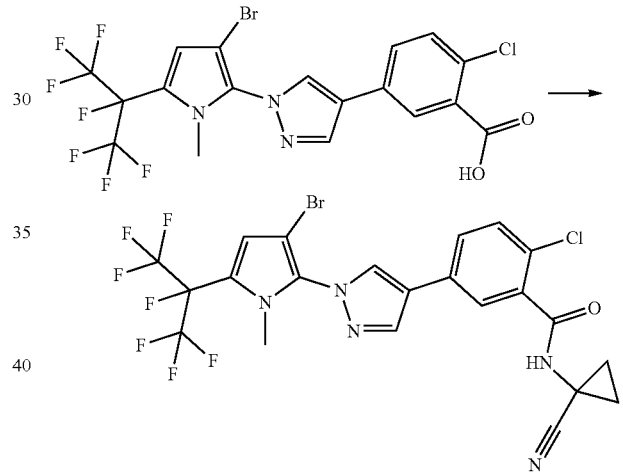

To a stirred solution of 5-[1-[3-bromo-1-methyl-5-[1,2,2,2-tetrafluoro-1-(trifluoromethyl)ethyl]pyrrol-2-yl]pyrazol-4-yl]-2-chloro-benzoic acid (0.090 g, 0.164 mmol) in dry dichloromethane (2.0 mL) one drop of dry dimethylformamide was added followed by the addition of oxalyl chloride (0.043 g, 0.33 mmol) at room temperature. The reaction mixture was stirred for 30 min at room temperature and then for 10 min at 40° C. After cooling down to room temperature, the reaction mixture was evaporated to dryness. The remaining acid chloride was dissolved in dry pyridine (2.0 mL) followed by the addition of 1-amino-1-cyano-cyclopropane hydrochloride (0.029 g, 0.25 mmol). The reaction mixture was stirred for 1 h at room temperature. The reaction mixture was evaporated to dryness and the crude product was purified by flash chromatography (silica, cyclohexane/gradient of ethyl acetate from 0 to 40%) to afford a yellow solid.

$^1$H NMR (400 MHz, CDCl$_3$) δ ppm 1.43 (m, 2H), 1.72 (m, 2H), 3.55 (d, J=3.4 Hz, 3H), 6.64 (s, 1H), 6.89 (s, 1H), 7.45 (d, J=8.4 Hz, 1H), 7.59 (dd, J=8.4, 2.2 Hz, 1H), 7.97 (s, 1H), 7.98 (d, J=2.2 Hz, 1H), 8.12 (s, 1H).

$^{19}$F NMR (376 MHz, CDCl$_3$) δ ppm −180.00 (s, 1F), −75.29 (s, 6F).

LC-MS (Method A): t$_R$=1.16 min, m/z=612 [M−1], 614 [M+1].

Example 3: 5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-benzamide

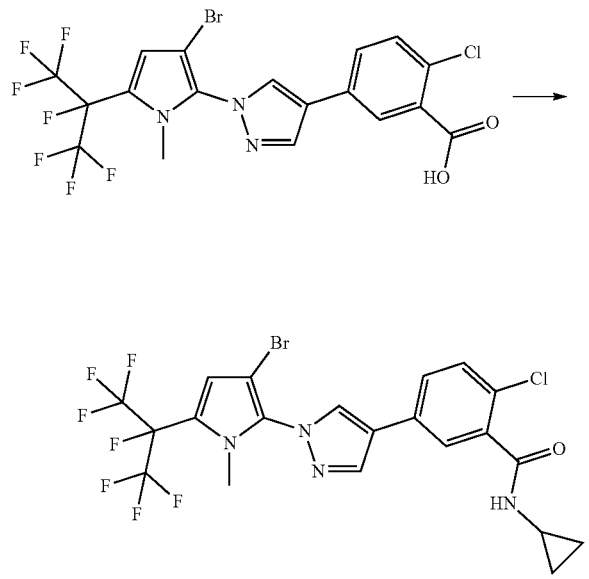 [SMILES: Cn1c(C(F)(C(F)(F)F)C(F)(F)F)cc(Br)c1-n1cc(-c2ccc(Cl)c(C(=O)O)c2)cn1 ; CN(C(=O)c1cc(-c2cnn(-c3c(Br)cc(C(F)(C(F)(F)F)C(F)(F)F)n3C)c2)ccc1Cl)C1CC1]

To a stirred solution of 5-[1-[3-bromo-1-methyl-5-[1,2,2,2-tetrafluoro-1-(trifluoromethyl)ethyl]pyrrol-2-yl]pyrazol-4-yl]-2-chloro-benzoic acid (0.050 g, 0.091 mmol) in dry dichloromethane (1.0 mL) one drop of dry dimethylformamide was added followed by the addition of oxalyl chloride (0.024 g, 0.18 mmol) at room temperature. The reaction mixture was stirred for 30 min at room temperature and then for 10 min at 40° C. After cooling down to room temperature, the reaction mixture was evaporated to dryness. The remaining acid chloride was dissolved in dry pyridine (1.0 mL) followed by the addition of cyclopropanamine (0.016 g, 0.27 mmol). The reaction mixture was stirred for 1 h at room temperature.

The reaction mixture was evaporated to dryness and the crude product was purified by flash chromatography (silica, cyclohexane/gradient of ethyl acetate from 0 to 30%) to afford a white solid.

$^1$H NMR (400 MHz, CDCl$_3$) δ ppm 0.69 (m, 2H), 0.92 (m, 2H), 2.97 (m, 1H), 3.55 (d, J=3.7 Hz, 3H), 6.38 (br s, 1H), 6.64 (s, 1H), 7.43 (d, J=8.4 Hz, 1H), 7.53 (dd, J=8.4, 2.2 Hz, 1H), 7.88 (d, J=2.2 Hz, 1H), 7.93 (s, 1H), 8.10 (s, 1H).

$^{19}$F NMR (376 MHz, CDCl$_3$) δ ppm −179.91 (s, 1F), −75.32 (s, 6F).

LC-MS (Method A): t$_R$=1.17 min, m/z=585 [M−1], 587 [M+1].

Example 4: 5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-N-methyl-benzamide

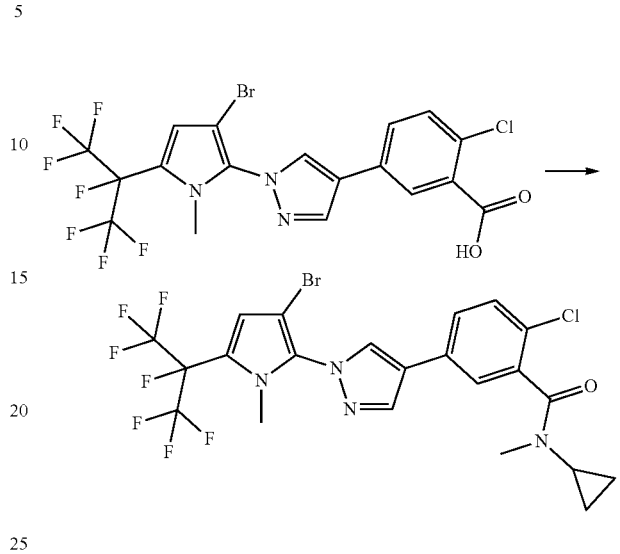

To a stirred solution of 5-[1-[3-bromo-1-methyl-5-[1,2,2,2-tetrafluoro-1-(trifluoromethyl)ethyl]pyrrol-2-yl]pyrazol-4-yl]-2-chloro-benzoic acid (0.070 g, 0.128 mmol) in dry dichloromethane (1.3 mL) one drop of dry dimethylformamide was added followed by the addition of oxalyl chloride (0.033 g, 0.26 mmol) at room temperature. The reaction mixture was stirred for 30 min at room temperature and then for 10 min at 40° C. After cooling down to room temperature, the reaction mixture was evaporated to dryness. The remaining acid chloride was dissolved in dry pyridine (1.3 mL) followed by the addition of N-methylcyclopropanamine hydrochloride (0.027 g, 0.25 mmol). The reaction mixture was stirred for 1 h at room temperature. The reaction mixture was evaporated to dryness and the crude product was purified by flash chromatography (silica, cyclohexane/gradient of ethyl acetate from 0 to 30%) to afford a white solid.

$^1$H NMR (400 MHz, CDCl$_3$) δ ppm 0.55 (m, 2H), 0.87 (m, 2H), 2.80 (m, 1H), 3.16 (s, 3H), 3.55 (d, J=3.6 Hz, 3H), 6.64 (s, 1H), 7.41-7.53 (m, 3H), 7.90 (s, 1H), 8.08 (s, 1H).

$^{19}$F NMR (376 MHz, CDCl$_3$) δ ppm −179.93 (s, 1F), −75.32 (s, 6F).

LC-MS (Method A): t$_R$=1.24 min, m/z=601 [M+1].

Example 5: 2-chloro-N-(1-cyanocyclopropyl)-5-[3-[1-methyl-5-[1,2,2,2-tetrafluoro-1-(trifluoromethyl)ethyl]pyrrol-2-yl]isoxazol-5-yl]benzamide a) Preparation of 1-methyl-5-[1,2,2,2-tetrafluoro-1-(trifluoromethyl)ethyl]pyrrole-2-carbaldehyde

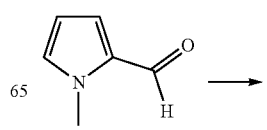

-continued

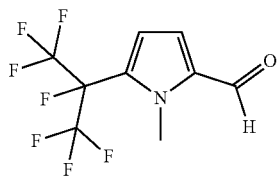

To a stirred mixture of 1-methylpyrrole-2-carbaldehyde (3.27 g, 30.0 mmol), 1,1,1,2,3,3,3-heptafluoro-2-iodo-propane (6.00 g, 20.3 mmol), iron(II) sulfate heptahydrate (1.11 g, 4.0 mmol) and dimethyl sulfoxide (40.0 g) was added 30% hydrogen peroxide solution (4.54 g, 40.0 mmol) dropwise within 15 min while keeping the temperature at 55-60° C. The mixture was kept at 60° C. for 5 min and then allowed to cool slowly to room temperature.

The reaction mixture was diluted with water (120 mL) and extracted twice with pentane. The combined extract was washed with water, dried over MgSO$_4$ and evaporated to afford the crude product which was purified by flash chromatography (silica, cyclohexane/gradient of ethyl acetate from 0 to 10%).

$^1$H NMR (400 MHz, CDCl$_3$) δ ppm 4.14 (d, J=3.7 Hz, 3H), 6.60 (m, 1H), 6.95 (dd, J=4.5, 1.5 Hz, 1H), 9.67 (s, 1H).

LC-MS (Method A): $t_R$=1.08, no molecular ion peaks

Preparation of 1-methyl-5-[1,2,2,2-tetrafluoro-1-(trifluoromethyl)ethyl]pyrrole-2-carbaldehyde oxime

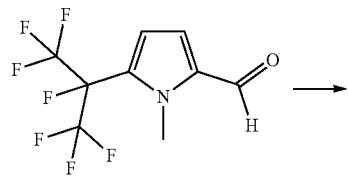

To a stirred solution of 1-methyl-5-[1,2,2,2-tetrafluoro-1-(trifluoromethyl)ethyl]pyrrole-2-carbaldehyde (0.50 g, 1.8 mmol) in anhydrous ethanol (2.7 mL) was added Hydroxylamine 50% solution in water (0.14 g, 2.2 mmol). The reaction mixture was heated to 60° C. for 30 min and then it was evaporated to dryness to afford the crude product which was used as is in the next step.

LC-MS (Method A): $t_R$=1.00, 1.02 (cis/trans mixture), m/z=291 [M−1], 293 [M+1].

c) Preparation of methyl 2-chloro-5-[3-[1-methyl-5-[1,2,2,2-tetrafluoro-1-(trifluoromethyl)ethyl]pyrrol-2-yl]isoxazol-5-yl]benzoate

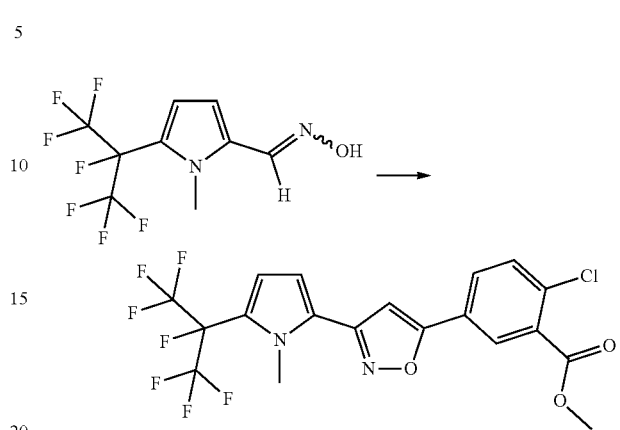

To a stirred mixture of 1-methyl-5-[1,2,2,2-tetrafluoro-1-(trifluoromethyl)ethyl]pyrrole-2-carbaldehyde oxime (0.49 g, 1.7 mmol), methyl 2-chloro-5-ethynyl-benzoate (0.39 g, 2.0 mmol), triethylamine (0.26 g, 2.5 mmol) and dichloromethane (3.4 mL) was added sodium hypochlorite 12% solution (4.0 g, 6.4 mmol) at 0° C. The reaction mixture was stirred for 1 h at room temperature.

The reaction mixture was diluted with water and extracted with dichloromethane. The extract was consecutively washed with water and brine, dried over magnesium sulfate and evaporated. The crude product was purified by flash chromatography (silica, cyclohexane/gradient of ethyl acetate from 0 to 10%) to afford the title compound as a yellow solid.

$^1$H NMR (400 MHz, CDCl$_3$) δ ppm 4.00 (s, 3H), 4.10 (d, J=3.3 Hz, 3H), 6.62 (m, 2H), 6.76 (s, 1H), 7.61 (d, J=8.4 Hz, 1H), 7.88 (dd, J=8.4, 2.2 Hz, 1H), 8.29 (d, J=2.2 Hz, 1H).

$^{19}$F NMR (376 MHz, CDCl$_3$) δ ppm −178.61 (s, 1F), −75.10 (s, 6F).

LC-MS (Method A): $t_R$=1.33 min, m/z=485 [M+1].

d) Preparation of 2-chloro-N-(1-cyanocyclopropyl)-5-[3-[1-methyl-5-[1,2,2,2-tetrafluoro-1-(trifluoromethyl)ethyl]pyrrol-2-yl]isoxazol-5-yl]benzamide

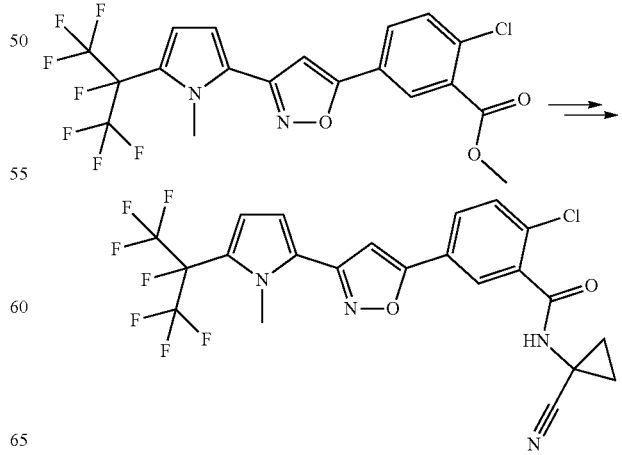

Hydrolysis and amide coupling were performed as described for above examples.

¹H NMR (400 MHz, CDCl₃) δ ppm 1.45 (m, 2H), 1.72 (m, 2H), 4.10 (d, J=3.1 Hz, 3H), 6.63 (m, 2H), 6.80 (s, 1H), 6.87 (s, 1H), 7.57 (d, J=8.4 Hz, 1H), 7.90 (dd, J=8.4, 2.2 Hz, 1H), 8.19 (d, J=2.2 Hz, 1H).

¹⁹F NMR (376 MHz, CDCl₃) δ ppm −178.63 (s, 1F), −75.08 (s, 6F).

LC-MS (Method A): $t_R$=1.18 min, m/z=533 [M−1], 535 [M+1].

Example 6: 5-[3-[3-bromo-1-methyl-5-[1,2,2,2-tetrafluoro-1-(trifluoromethyl)ethyl]pyrrol-2-yl]isoxazol-5-yl]-2-chloro-N-(1-cyanocyclopropyl)benzamide a) Preparation of methyl 5-[3-[3-bromo-1-methyl-5-[1,2,2,2-tetrafluoro-1-(trifluoromethyl)ethyl]pyrrol-2-yl]isoxazol-5-yl]-2-chloro-benzoate

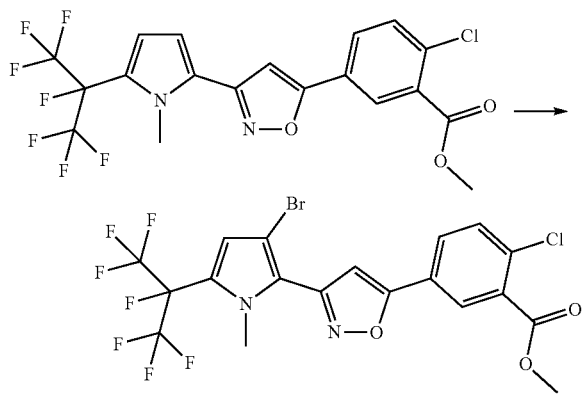

A mixture of methyl 2-chloro-5-[3-[1-methyl-5-[1,2,2,2-tetrafluoro-1-(trifluoromethyl)ethyl]pyrrol-2-yl]isoxazol-5-yl]benzoate (0.050 g, 0.103 mmol), N-bromosuccinimide (0.019 g, 0.108 mmol) and glacial acetic acid (1.0 mL) was stirred for 1 h at room temperature. The reaction mixture was evaporated to dryness and the remaining crude product was used in the next step without purification.

LC-MS (Method A): $t_R$=1.36 min, m/z=563 [M+1].

b) Preparation of 5-[3-[3-bromo-1-methyl-5-[1,2,2,2-tetrafluoro-1-(trifluoromethyl)ethyl]pyrrol-2-yl]isoxazol-5-yl]-2-chloro-N-(1-cyanocyclopropyl)benzamide

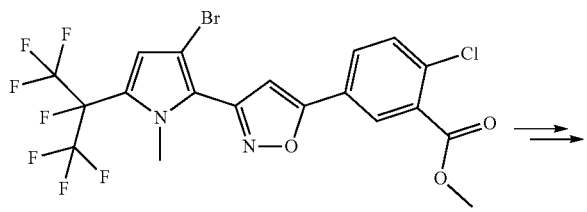

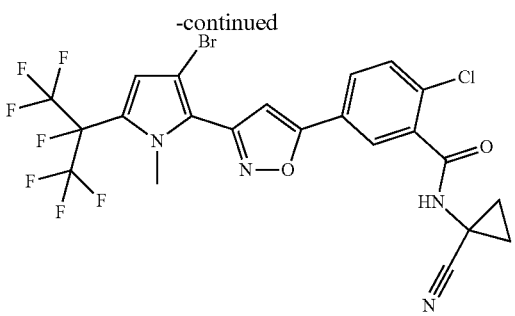

Hydrolysis and amide coupling were performed as described for above examples.

¹H NMR (400 MHz, CDCl₃) δ ppm 1.45 (m, 2H), 1.73 (m, 2H), 3.95 (d, J=3.5 Hz, 3H), 6.70 (s, 1H), 6.88 (s, 1H), 7.10 (s, 1H), 7.58 (d, J=8.4 Hz, 1H), 7.92 (dd, J=8.4, 2.2 Hz, 1H), 8.22 (d, J=2.2 Hz, 1H).

¹⁹F NMR (376 MHz, CDCl₃) δ ppm −179.25 (s, 1F), −75.16 (s, 6F).

LC-MS (Method A): $t_R$=1.21 min, m/z=611 [M−1], 613 [M+1].

Example 7: 2-chloro-N-(1-cyanocyclopropyl)-5-[1-[1-methyl-3-nitro-5-[1,2,2,2-tetrafluoro-1-(trifluoromethyl)ethyl]pyrrol-2-yl]pyrazol-4-yl]benzamide a) Preparation of methyl 2-chloro-5-[1-[1-methyl-3-nitro-5-[1,2,2,2-tetrafluoro-1-(trifluoromethyl)ethyl]pyrrol-2-yl]pyrazol-4-yl]benzoate

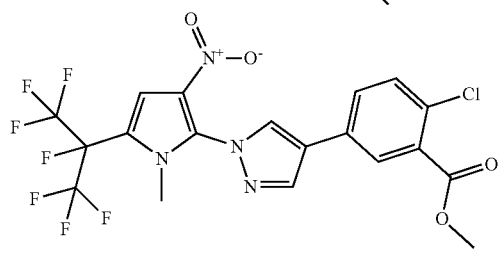

To a stirred solution of Methyl 2-chloro-5-[1-[1-methyl-5-[1,2,2,2-tetrafluoro-1-(trifluoromethyl)ethyl]pyrrol-2-yl]pyrazol-4-yl]benzoate (0.10 g, 0.21 mmol) in acetic anhydride (1.1 g) was added 99% nitric acid (0.026 g, 0.41 mmol) at room temperature. The reaction mixture was stirred for 1 h at room temperature and then it was poured into cold water (5 mL). The product was extracted with TBME, the extract was dried over magnesium sulfate and evaporated to afford the title compound.

¹H NMR (400 MHz, CDCl₃) δ ppm 3.61 (d, J=3.7 Hz, 3H), 3.98 (s, 3H), 7.26 (s, 1H), 7.52 (d, J=8.2 Hz, 1H), 7.60 (m, 1H), 8.03 (m, 1H), 8.05 (s, 1H), 8.18 (s, 1H).

¹⁹F NMR (376 MHz, CDCl₃) δ ppm −180.91 (s, 1F), −75.20 (s, 6F).

LC-MS (Method A): $t_R$=1.21 min, m/z=527 [M−1], 529 [M+1].

b) Preparation of 2-chloro-N-(1-cyanocyclopropyl)-5-[1-[1-methyl-3-nitro-5-[1,2,2,2-tetrafluoro-1-(trifluoromethyl)ethyl]pyrrol-2-yl]pyrazol-4-yl]benzamide

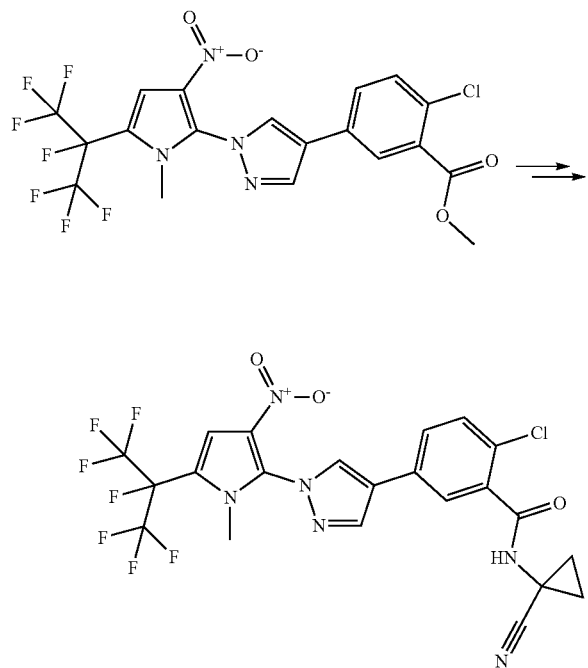 [SMILES: COC(=O)c1cc(-c2cnn(-c3c([N+](=O)[O-])cc(C(F)(C(F)(F)F)C(F)(F)F)n3C)c2)ccc1Cl ; Cn1c(C(F)(C(F)(F)F)C(F)(F)F)cc([N+](=O)[O-])c1-n1cc(-c2ccc(Cl)c(C(=O)NC3(C#N)CC3)c2)cn1]

Hydrolysis and amide coupling were performed as described for above examples.

¹H NMR (400 MHz, CDCl₃) δ ppm 1.44 (m, 2H), 1.71 (m, 2H), 3.61 (d, J=4.0 Hz, 3H), 6.92 (s, 1H), 7.26 (s, 1H), 7.45 (d, J=8.4 Hz, 1H), 7.59 (dd, J=8.4, 2.2 Hz, 1H), 7.96 (d, J=2.2 Hz, 1H), 8.06 (s, 1H), 8.17 (s, 1H).

¹⁹F NMR (376 MHz, CDCl₃) δ ppm −180.92 (s, 1F), −75.22 (s, 6F).

LC-MS (Method A): t_R=1.10 min, m/z=577 [M−1], 579 [M+1].

Example 8: 2-chloro-N-(1-cyanocyclopropyl)-5-[1-[1-methyl-5-[1,2,2,2-tetrafluoro-1-(trifluoromethyl)ethyl]-3-(trifluoromethyl)pyrrol-2-yl]pyrazol-4-yl]benzamide a) Preparation of methyl 2-chloro-5-[1-[3-iodo-1-methyl-5-[1,2,2,2-tetrafluoro-1-(trifluoromethyl)ethyl]pyrrol-2-yl]pyrazol-4-yl]benzoate

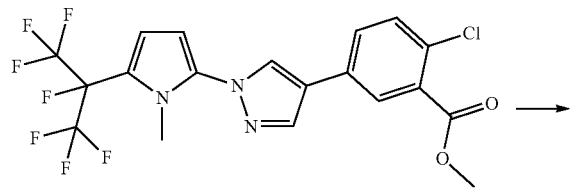

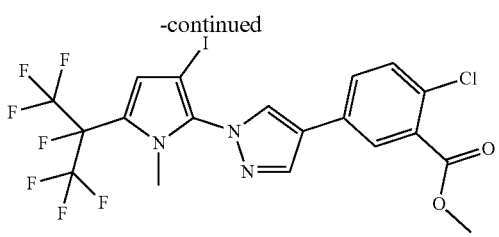

A mixture of Methyl 2-chloro-5-[1-[1-methyl-5-[1,2,2,2-tetrafluoro-1-(trifluoromethyl)ethyl]pyrrol-2-yl]pyrazol-4-yl]benzoate (0.50 g, 1.0 mmol), N-iodosuccinimide (0.24 g, 1.1 mmol) and glacial acetic acid (8 mL) was stirred for 14 h at room temperature. The reaction mixture was evaporated to dryness and the remaining residue was purified by flash chromatography (silica, cyclohexane/10% ethyl acetate) to afford a yellow solid.

¹H NMR (400 MHz, CDCl₃) δ ppm 3.55 (d, J=3.7 Hz, 3H), 3.98 (s, 3H), 6.70 (s, 1H), 7.51 (d, J=8.2 Hz, 1H), 7.60 (dd, J=8.2, 2.2 Hz, 1H), 7.94 (d, J=0.7 Hz, 1H), 8.02 (d, J=2.2 Hz, 1H), 8.12 (d, J=0.7 Hz, 1H).

¹⁹F NMR (376 MHz, CDCl₃) δ ppm −180.06 (s, 1F), −75.27 (s, 6F).

LC-MS (Method A): t_R=1.28 min, m/z=608 [M−1], 610 [M+1].

b) Preparation of methyl 2-chloro-5-[1-[1-methyl-5-[1,2,2,2-tetrafluoro-1-(trifluoromethyl)ethyl]-3-(trifluoromethyl)pyrrol-2-yl]pyrazol-4-yl]benzoate

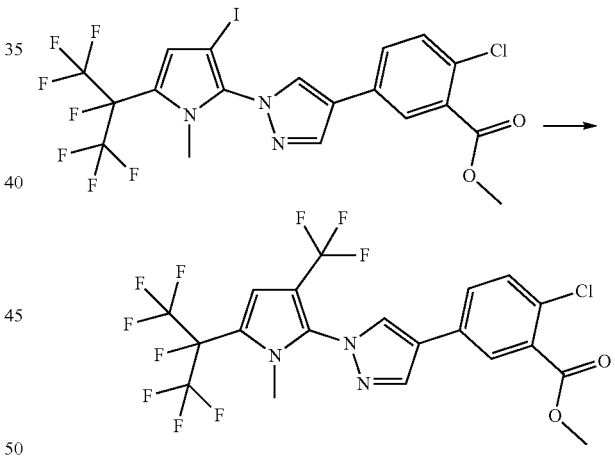

A vial was charged with methyl 2-chloro-5-[1-[3-iodo-1-methyl-5-[1,2,2,2-tetrafluoro-1-(trifluoromethyl)ethyl]pyrrol-2-yl]pyrazol-4-yl]benzoate (0.050 g, 0.082 mmol), Copper(I) iodide (0.016 g, 0.082 mmol) and anhydrous NMP (0.82 mL). The mixture was purged with argon followed by the addition of Methyl 2,2-difluoro-2-(fluorosulfonyl)acetate (0.049 g, 0.25 mmol). The vial was sealed up and heated to 90° C. for 4 h. The reaction mixture was filtered over a celite pad. The filtrate was diluted with pentane, washed with water, dried over magnesium sulfate, filtered and evaporated. The crude product was purified by flash chromatography.

¹H NMR (400 MHz, CDCl₃) δ ppm 3.52 (d, J=3.7 Hz, 3H), 3.98 (s, 3H), 6.82 (s, 1H), 7.52 (d, J=8.4 Hz, 1H), 7.59 (dd, J=8.4, 2.2 Hz, 1H), 7.94 (s, 1H), 8.00 (d, J=2.2 Hz, 1H), 8.13 (s, 1H).

¹⁹F NMR (376 MHz, CDCl₃) δ ppm −180.65 (s, 1F), −75.31 (s, 6F), −57.25 (s, 3F).

LC-MS (Method A): $t_R$=1.28 min, m/z=550 [M−1], 552 [M+1].

c) Preparation of 2-chloro-N-(1-cyanocyclopropyl)-5-[1-[1-methyl-5-[1,2,2,2-tetrafluoro-1-(trifluoromethyl)ethyl]-3-(trifluoromethyl)pyrrol-2-yl]pyrazol-4-yl]benzamide

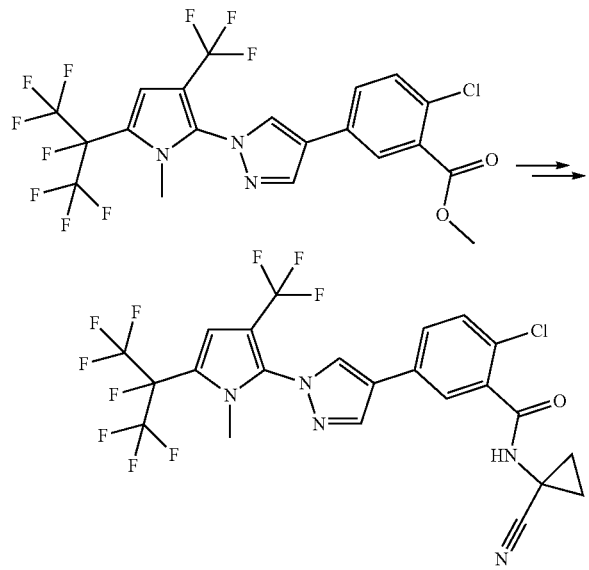

Hydrolysis and amide coupling were performed as described for above examples.

¹H NMR (400 MHz, CDCl₃) δ ppm 1.43 (m, 2H), 1.71 (m, 2H), 3.52 (d, J=3.7 Hz, 3H), 6.82 (s, 1H), 6.91 (s, 1H), 7.46 (d, J=8.4 Hz, 1H), 7.58 (dd, J=8.4, 2.2 Hz, 1H), 7.95 (m, 2H), 8.13 (s, 1H).

¹⁹F NMR (376 MHz, CDCl₃) δ ppm −180.66 (s, 1F), −75.30 (s, 6F), −57.22 (s, 3F).

LC-MS (Method A): $t_R$=1.15 min, m/z=600 [M−1], 602 [M+1].

Example 9: 2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)benzamide a) Preparation of methyl 2-chloro-5-[1-[3-chloro-1-methyl-5-[1,2,2,2-tetrafluoro-1-(trifluoromethyl)ethyl]pyrrol-2-yl]pyrazol-4-yl]benzoate

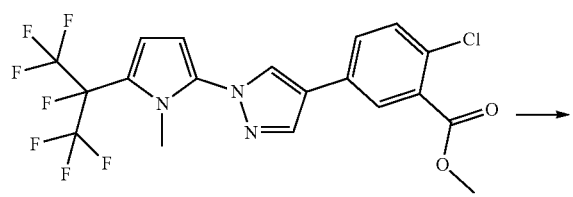

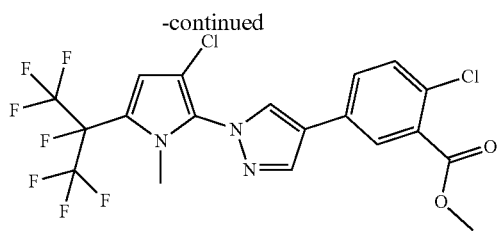

To a stirred mixture of Methyl 2-chloro-5-[1-[1-methyl-5-[1,2,2,2-tetrafluoro-1-(trifluoromethyl)ethyl]pyrrol-2-yl]pyrazol-4-yl]benzoate (0.11 g, 0.23 mmol), N-chlorosuccinimide (0.032 g, 0.24 mmol) and glacial acetic acid (2.0 mL) was added a drop of 98% H₂SO₄ at room temperature followed by stirring for 3 h at room temperature. The reaction mixture was evaporated to dryness and the remaining residue was purified by flash chromatography.

¹H NMR (400 MHz, CDCl₃) δ ppm 3.55 (d, J=3.7 Hz, 3H), 3.98 (s, 3H), 6.59 (s, 1H), 7.51 (d, J=8.4 Hz, 1H), 7.60 (dd, J=8.3, 2.4 Hz, 1H), 7.95 (s, 1H), 8.01 (d, J=2.2 Hz, 1H), 8.12 (s, 1H).

¹⁹F NMR (376 MHz, CDCl₃) δ ppm −179.99 (s, 1F), −75.33 (s, 6F).

LC-MS (Method A): $t_R$=1.28 min, m/z=518 [M+1].

b) Preparation of 2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)benzamide

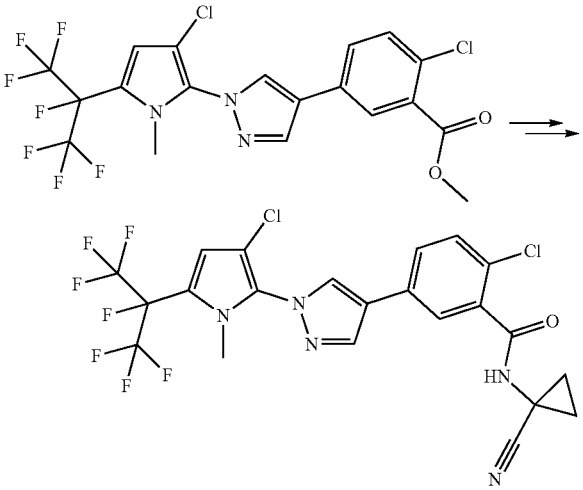

Hydrolysis and amide coupling were performed as described for above examples.

¹H NMR (400 MHz, CDCl₃) δ ppm 1.43 (m, 2H), 1.71 (m, 2H), 3.55 (d, J=3.7 Hz, 3H), 6.59 (s, 1H), 6.90 (s, 1H), 7.46 (d, J=8.4 Hz, 1H), 7.59 (dd, J=8.4, 2.2 Hz, 1H), 7.96 (s, 1H), 7.97 (d, J=2.2 Hz, 1H), 8.12 (s, 1H).

¹⁹F NMR (376 MHz, CDCl₃) δ ppm −179.97 (s, 1F), −75.32 (s, 6F).

LC-MS (Method A): $t_R$=1.15 min, m/z=566 [M−1], 568 [M+1].

Example 10: 2-chloro-N-(1-cyanocyclopropyl)-5-[1-[3-cyano-1-methyl-5-[1,2,2,2-tetrafluoro-1-(trifluoromethyl)ethyl]pyrrol-2-yl]pyrazol-4-yl]benzamide a) Preparation of methyl 2-chloro-5-[1-[3-cyano-1-methyl-5-[1,2,2,2-tetrafluoro-1-(trifluoromethyl)ethyl]pyrrol-2-yl]pyrazol-4-yl]benzoate

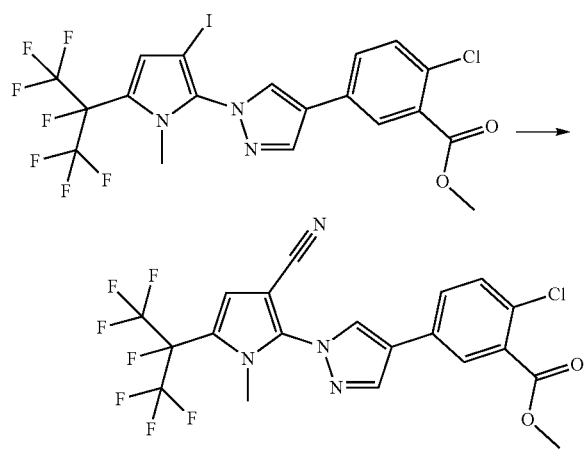

A mixture of 2-chloro-5-[1-[3-iodo-1-methyl-5-[1,2,2,2-tetrafluoro-1-(trifluoromethyl)ethyl]pyrrol-2-yl]pyrazol-4-yl]benzoate (0.60 g, 0.98 mmol), copper(I) cyanide (0.18 g, 2.0 mmol), L-proline (0.12 g, 0.98 mmol) and dry DMF (10 mL) was heated to 140° C. for 7 h. After cooling to room temperature, ethyl acetate (100 mL) and water (20 mL) were added to the reaction mixture and the resulting slurry was filtered over a celite pad. The arganic layer was separated, washed 5 times with water (5×20 mL), once with brine and evaporated. The crude product was purified by flash chromatography (silica, cyclohexane/gradient of ethyl acetate from 0 to 10%).

$^1$H NMR (400 MHz, CDCl$_3$) δ ppm 3.71 (d, J=3.7 Hz, 3H), 3.98 (s, 3H), 6.89 (s, 1H), 7.52 (d, J=8.4 Hz, 1H), 7.60 (dd, J=8.4, 2.2 Hz, 1H), 8.01 (d, J=2.2 Hz, 1H), 8.08 (s, 1H), 8.16 (s, 1H).

$^{19}$F NMR (376 MHz, CDCl$_3$) δ ppm −180.88 (s, 1F), −75.28 (s, 6F).

LC-MS (Method A): t$_R$=1.20 min, m/z=507 [M−1], 509 [M+1].

b) Preparation of 2-chloro-N-(1-cyanocyclopropyl)-5-[1-[3-cyano-1-methyl-5-[1,2,2,2-tetrafluoro-1-(trifluoromethyl)ethyl]pyrrol-2-yl]pyrazol-4-yl]benzamide

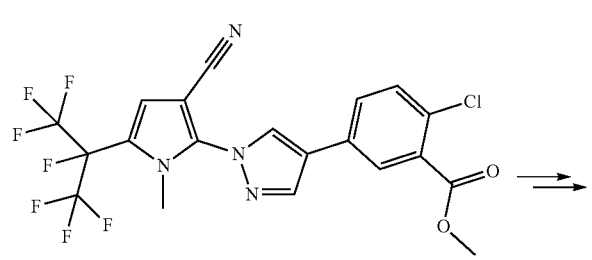

-continued

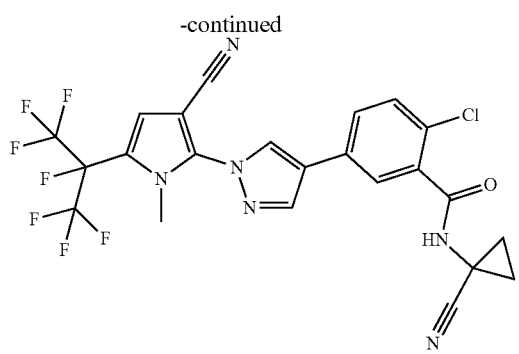

Hydrolysis and amide coupling were performed as described for above examples.

$^1$H NMR (400 MHz, CDCl$_3$) δ ppm 1.44 (m, 2H), 1.71 (m, 2H), 3.72 (d, J=3.7 Hz, 3H), 6.89 (s, 1H), 6.90 (s, 1H), 7.47 (d, J=8.4 Hz, 1H), 7.59 (dd, J=8.4, 2.2 Hz, 1H), 7.95 (d, J=2.2 Hz, 1H), 8.08 (s, 1H), 8.16 (s, 1H).

$^{19}$F NMR (376 MHz, CDCl$_3$) δ ppm −180.87 (s, 1F), −75.27 (s, 6F).

LC-MS (Method A): t$_R$=1.09 min, m/z=557 [M−1], 559 [M+1].

Example 11: 2-chloro-N-(1-cyanocyclopropyl)-5-[1-[1,3-dimethyl-5-[1,2,2,2-tetrafluoro-1-(trifluoromethyl)ethyl]pyrrol-2-yl]pyrazol-4-yl]benzamide a) Preparation of methyl 2-chloro-5-[1-[1,3-dimethyl-5-[1,2,2,2-tetrafluoro-1-(trifluoromethyl)ethyl]pyrrol-2-yl]pyrazol-4-yl]benzoate

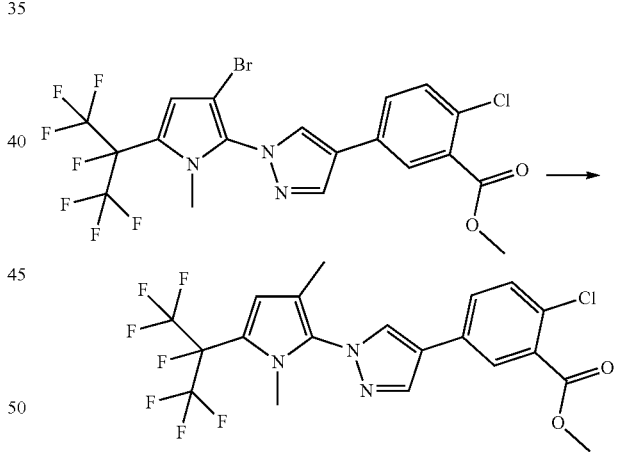

A microwave tube was charged with methyl 5-[1-[3-bromo-1-methyl-5-[1,2,2,2-tetrafluoro-1-(trifluoromethyl)ethyl]pyrrol-2-yl]pyrazol-4-yl]-2-chloro-benzoate (0.150 g, 0.27 mmol), methylboronic acid (0.051 g, 0.85 mmol), Pd(dppf)Cl$_2$ (0.020 g, 0.027 mol), anhydrous cesium fluoride (0.28 g, 0.85 mmol) and anhydrous dioxane (1.1 mL). The tube was purged with argon, sealed up and heated in a microwave reactor to 120° C. for 30 min. The reaction mixture was diluted with water and extracted with ethyl acetate. The organic layer was consecutively washed with water and brine, dried over magnesium sulfate and evaporated. The crude product was purified by flash chromatography (silica, cyclohexane/gradient of ethyl acetate from 0 to 20%).

LC-MS (Method A): $t_R$=1.28 min, m/z=498 [M+1].

b) Preparation of 2-chloro-N-(1-cyanocyclopropyl)-5-[1-[1,3-dimethyl-5-[1,2,2,2-tetrafluoro-1-(trifluoromethyl)ethyl]pyrrol-2-yl]pyrazol-4-yl]benzamide

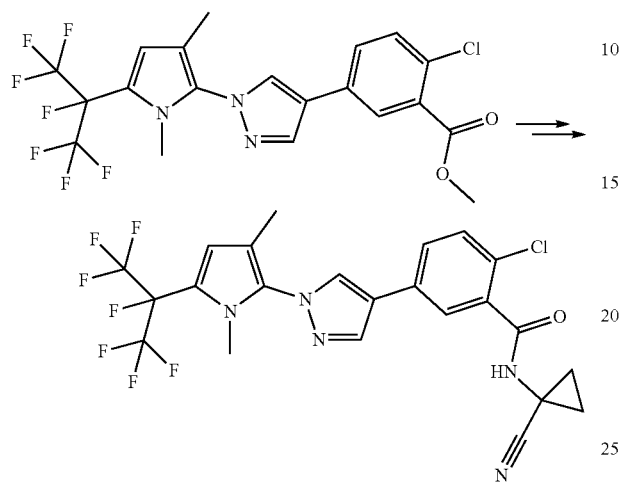

Hydrolysis and amide coupling were performed as described for above examples.

$^1$H NMR (400 MHz, CDCl$_3$) δ ppm 1.43 (m, 2H), 1.71 (m, 2H), 1.98 (s, 3H), 3.43 (d, J=3.3 Hz, 3H), 6.42 (s, 1H), 6.88 (s, 1H), 7.45 (d, J=8.4 Hz, 1H), 7.58 (dd, J=8.4, 2.2 Hz, 1H), 7.87 (s, 1H), 7.97 (d, J=2.2 Hz, 1H), 8.08 (s, 1H).

$^{19}$F NMR (376 MHz, CDCl$_3$) δ ppm −179.09 (s, 1F), −75.30 (s, 6F).

LC-MS (Method A): $t_R$=1.15 min, m/z=546 [M−1], 548 [M+1].

Example 12: 5-[1-[3-bromo-1-(fluoromethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide a) Preparation of methyl 2-chloro-5-[1-[1-(methoxymethyl)pyrrol-2-yl]pyrazol-4-yl]benzoate

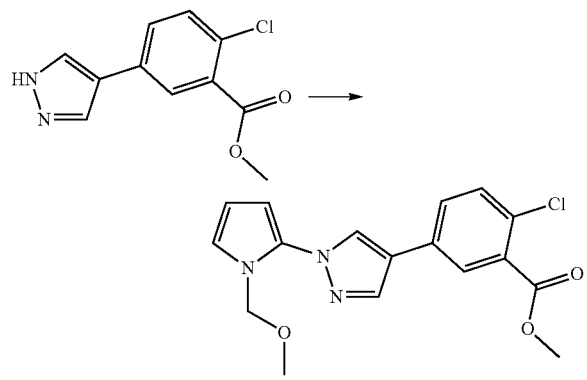

To a stirred mixture of methyl 2-chloro-5-(1H-pyrazol-4-yl)benzoate (3.59 g, 15.2 mmol), 1-(methoxymethyl)pyrrole (3.37 g, 30.3 mmol), sodium bicarbonate (1.27 g, 15.2 mmol), acetonitrile (25 g) and water (10 g) was added 12% sodium hypochlorite solution (20.7 g, 33.3 mmol) dropwise within 30 min while keeping the temperature at 30-35° C. After the addition was completed, the mixture was stirred at 30° C. for 30 min.

The reaction mixture was diluted with TBME (30 mL). The organic phase was separated and evaporated to give the crude product which was purified by flash chromatography (silica, cyclohexane/gradient of ethyl acetate from 5 to 20%).

$^1$H NMR (400 MHz, CDCl$_3$) δ ppm 3.23 (s, 3H), 3.97 (s, 3H), 5.19 (s, 2H), 6.23 (m, 1H), 6.30 (m, 1H), 6.81 (m, 1H), 7.47 (d, J=8.4 Hz, 1H), 7.57 (dd, J=8.4, 2.2 Hz, 1H), 7.93 (d, J=0.7 Hz, 1H), 7.98 (d, J=2.2 Hz, 1H), 8.01 (d, J=0.7 Hz, 1H).

LC-MS (Method A): $t_R$=1.03 min, m/z=346 [M+1].

b) Preparation of methyl 2-chloro-5-[1-[1-(methoxymethyl)-5-[1,2,2,2-tetrafluoro-1-(trifluoromethyl)ethyl]pyrrol-2-yl]pyrazol-4-yl]benzoate

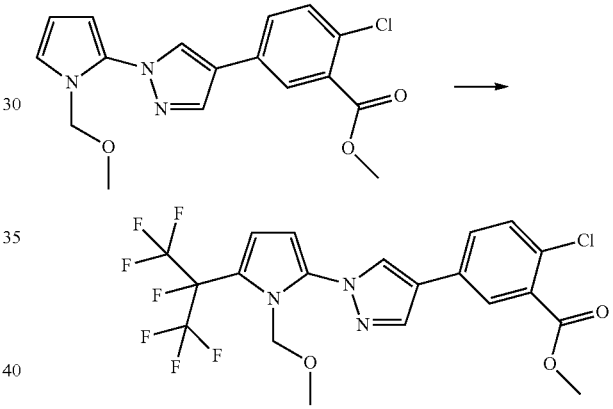

To a stirred mixture of methyl methyl 2-chloro-5-[1-[1-(methoxymethyl)pyrrol-2-yl]pyrazol-4-yl]benzoate (1.54 g, 4.45 mmol), 1,1,1,2,3,3,3-heptafluoro-2-iodo-propane (1.52 g, 5.12 mmol), iron(II) sulfate heptahydrate (0.250 g, 0.89 mmol) and dimethyl sulfoxide (8.0 g) was added 30% hydrogen peroxide solution (1.01 g, 8.9 mmol) dropwise within 20 min while keeping the temperature at 60-65° C. The mixture was kept at 60° C. for 5 min and then allowed to cool slowly to room temperature.

The reaction mixture was diluted with water (30 g) and extracted twice with cyclohexane (30+15 mL). The combined extract was washed with water (50 mL), dried over magnesium sulfate and evaporated to afford the title compound as a yellow gum.

$^1$H NMR (400 MHz, CDCl$_3$) δ ppm 3.14 (d, J=1.1 Hz, 3H), 3.98 (s, 3H), 5.30 (d, J=1.5 Hz, 2H), 6.40 (dd, J=4.4, 1.5 Hz, 1H), 6.64 (m, 1H), 7.50 (d, J=8.3 Hz, 1H), 7.58 (dd, J=8.3, 2.4 Hz, 1H), 7.95 (d, J=0.7 Hz, 1H), 7.99 (d, J=2.2 Hz, 1H), 8.06 (s, 1H).

$^{19}$F NMR (376 MHz, CDCl$_3$) δ ppm −180.71 (s, 1F), −75.72 (s, 6F).

LC-MS (Method A): $t_R$=1.24 min, m/z=514 [M+1].

c) Preparation of methyl 5-[1-[3-bromo-1-(methoxymethyl)-5-[1,2,2,2-tetrafluoro-1-(trifluoromethyl)ethyl]pyrrol-2-yl]pyrazol-4-yl]-2-chloro-benzoate

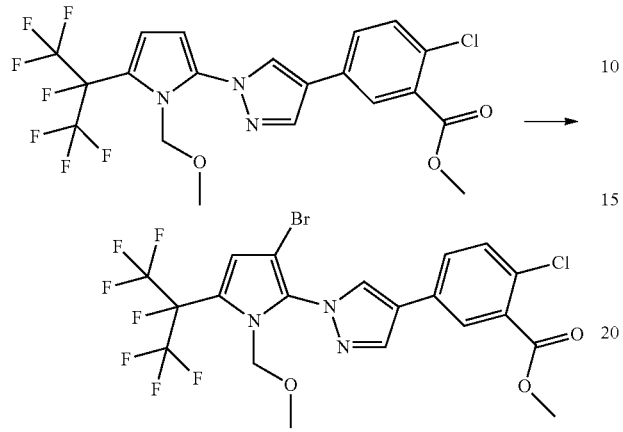

To a stirred solution of 2-chloro-5-[1-[1-(methoxymethyl)-5-[1,2,2,2-tetrafluoro-1-(trifluoromethyl)ethyl]pyrrol-2-yl]pyrazol-4-yl]benzoate (1.52 g, 2.96 mmol) in acetonitrile (10 mL) was added N-bromosuccinimide (0.585 g, 3.25 mmol) in several portions within 2 min at room temperature.

The reaction mixture was stirred for 2 h at room temperature.

The reaction mixture was diluted with water (30 g) and extracted twice with a cyclohexane/ethyl acetate mixture=3:1 (30+15 mL). The combined extract was washed with a 5% sodium bicarbonate solution (30 mL), dried over magnesium sulfate and evaporated to afford the title compound as a yellow gum.

LC-MS (Method A): $t_R$=1.28 min, m/z=592 [M+1].

d) Preparation of methyl 5-[1-[3-bromo-1-(bromomethyl)-5-[1,2,2,2-tetrafluoro-1-(trifluoromethyl)ethyl]pyrrol-2-yl]pyrazol-4-yl]-2-chloro-benzoate

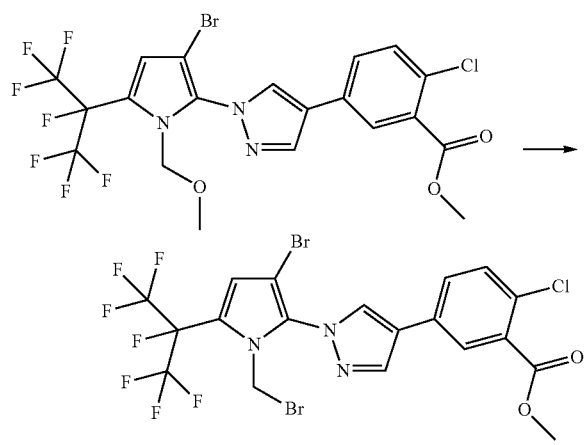

To a stirred solution of 5-[1-[3-bromo-1-(methoxymethyl)-5-[1,2,2,2-tetrafluoro-1-(trifluoromethyl)ethyl]pyrrol-2-yl]pyrazol-4-yl]-2-chloro-benzoate (1.03 g, 1.74 mmol) in dichloromethane (5 mL) was added 1M boron tribromide solution in dichloromethane (2.0 mL, 2.0 mmol) dropwise at room temperature. The reaction mixture was stirred for 6 h at room temperature.

The reaction mixture was quenched with ice. The organic phase was separated and evaporated to afford the crude product which was purified by flash chromatography (silica, cyclohexane/gradient of ethyl acetate from 0 to 20%).

$^1$H NMR (400 MHz, CDCl$_3$) δ ppm 3.98 (s, 3H), 5.80 (s, 2H), 6.77 (s, 1H), 7.52 (d, J=8.3 Hz, 1H), 7.62 (dd, J=8.3, 2.2 Hz, 1H), 8.03 (d, J=2.2 Hz, 1H), 8.06 (d, J=0.7 Hz, 1H), 8.17 (d, J=0.7 Hz, 1H).

$^{19}$F NMR (376 MHz, CDCl$_3$) δ ppm −181.55 (s, 1F), −75.39 (s, 6F).

LC-MS (Method A): $t_R$=1.31 min, m/z=640 [M+1].

e) Preparation of methyl 5-[1-[3-bromo-1-(fluoromethyl)-5-[1,2,2,2-tetrafluoro-1-(trifluoromethyl)ethyl]pyrrol-2-yl]pyrazol-4-yl]-2-chloro-benzoate

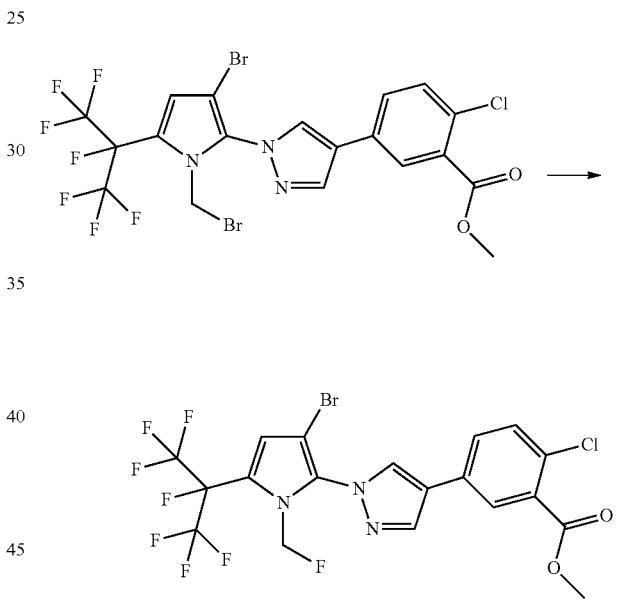

A mixture of 5-[1-[3-bromo-1-(bromomethyl)-5-[1,2,2,2-tetrafluoro-1-(trifluoromethyl)ethyl]pyrrol-2-yl]pyrazol-4-yl]-2-chloro-benzoate (0.137 g, 0.213 mmol), potassium fluoride (0.037 g, 0.639 mmol), 18-Crown-6 (11.5 mg, 0.043 mmol) and anhydrous acetonitrile (0.7 mL) was heated to 80° C. for 68 h under argon. The reaction mixture was evaporated and the product was isolated by flash chromatography (silica, cyclohexane/gradient of ethyl acetate from 0 to 15%)

$^1$H NMR (400 MHz, CDCl$_3$) δ ppm 3.98 (s, 3H), 5.85 (d, J=51.0 Hz, 2H), 6.76 (s, 1H), 7.52 (d, J=8.3 Hz, 1H), 7.60 (dd, J=8.3, 2.2 Hz, 1H), 8.01 (d, J=2.2 Hz, 1H), 8.02 (s, 1H), 8.14 (d, J=0.7 Hz, 1H).

$^{19}$F NMR (376 MHz, CDCl$_3$) δ ppm −181.76 (s, 1° F.), −162.02 (s, 1° F.), −75.67 (s, 6F).

LC-MS (Method A): $t_R$=1.26 min, m/z=578[M−1], 580 [M+1].

f) Preparation of 5-[1-[3-bromo-1-(fluoromethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide

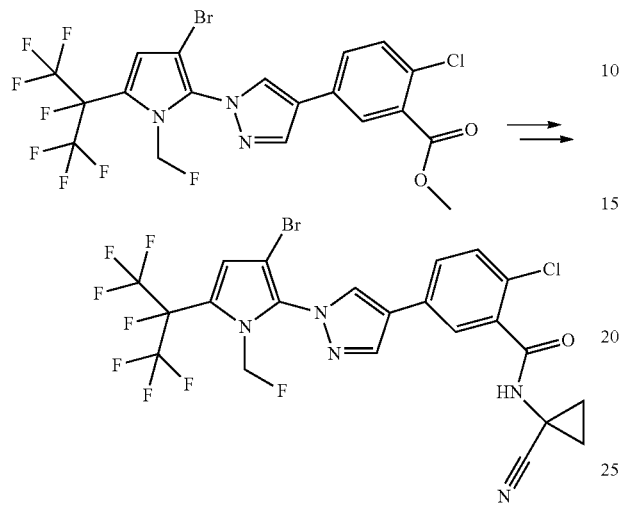

Hydrolysis and amide coupling were performed as described for above examples.

$^1$H NMR (400 MHz, CDCl$_3$) δ ppm 1.44 (m, 2H), 1.71 (m, 2H), 5.85 (d, J=51.0 Hz, 2H), 6.76 (s, 1H), 6.89 (s, 1H), 7.46 (d, J=8.4 Hz, 1H), 7.59 (dd, J=8.4, 2.2 Hz, 1H), 7.97 (d, J=2.2 Hz, 1H), 8.03 (s, 1H), 8.14 (s, 1H).

$^{19}$F NMR (376 MHz, CDCl$_3$) δ ppm −181.70 (s, 1° F.), −162.07 (s, 1° F.), −75.65 (s, 6F).

LC-MS (Method A): $t_R$=1.14 min, m/z=628 [M−1], 630 [M+1].

Example 13: 5-[1-[3-bromo-1-(cyanomethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide a) Preparation of methyl 5-[1-[3-bromo-1-(cyanomethyl)-5-[1,2,2,2-tetrafluoro-1-(trifluoromethyl)ethyl]pyrrol-2-yl]pyrazol-4-yl]-2-chloro-benzoate

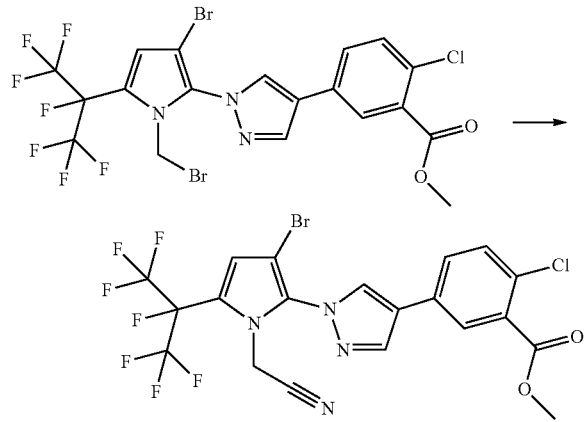

A mixture of 5-[1-[3-bromo-1-(bromomethyl)-5-[1,2,2,2-tetrafluoro-1-(trifluoromethyl)ethyl]pyrrol-2-yl]pyrazol-4-yl]-2-chloro-benzoate (0.133 g, 0.207 mmol), potassium cyanide (0.027 g, 0.415 mmol), 18-Crown-6 (11 mg, 0.042 mmol) and anhydrous acetonitrile (2.1 mL) was stirred at room temperature for 18 h under argon and then it was heated to 40° C. for 4 h. The reaction mixture was evaporated and the product was isolated by flash chromatography (silica, cyclohexane/gradient of ethyl acetate from 0 to 15%)

$^1$H NMR (400 MHz, CDCl$_3$) δ ppm 3.98 (s, 3H), 5.03 (m, 2H), 6.76 (s, 1H), 7.53 (d, J=8.1 Hz, 1H), 7.60 (dd, J=8.1, 2.2 Hz, 1H), 8.02 (d, J=2.2 Hz, 1H), 8.09 (s, 1H), 8.18 (s, 1H).

$^{19}$F NMR (376 MHz, CDCl$_3$) δ ppm −179.57 (s, 1F), −75.36 (s, 6F).

LC-MS (Method A): $t_R$=1.22 min, m/z=585 [M−1], 587 [M+1].

b) Preparation of 5-[1-[1-(2-amino-2-oxo-ethyl)-3-bromo-5-[1,2,2,2-tetrafluoro-1-(trifluoromethyl)ethyl]pyrrol-2-yl]pyrazol-4-yl]-2-chloro-benzoic acid

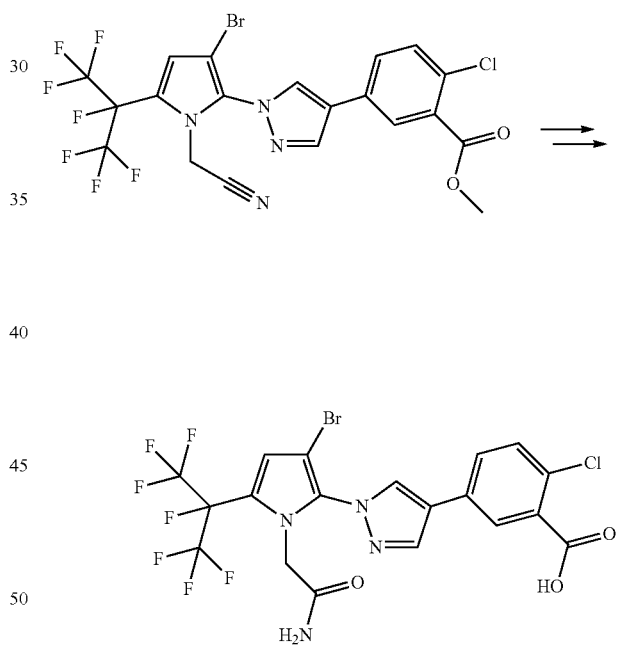

To a stirred solution of methyl 5-[1-[3-bromo-1-(cyanomethyl)-5-[1,2,2,2-tetrafluoro-1-(trifluoromethyl)ethyl]pyrrol-2-yl]pyrazol-4-yl]-2-chloro-benzoate (0.10 g, 0.17 mmol) in a mixture of tetrahydrofurane (2.7 mL) and water (0.7 mL) was added lithium hydroxide monohydrate (0.014 g, 0.34 mmol). The mixture was stirred over night at room temperature. The reaction mixture was acidified with 1N HCl and the product was extracted with ethyl acetate. The organic extract was washed with water than with brine, dried over magnesium sulfate and evaporated to result in the crude product which was used as is in the next step.

LC-MS (Method A): $t_R$=1.00 min, m/z=589 [M−1], 591 [M+1].

c) Preparation of 5-[1-[3-bromo-1-(cyanomethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide

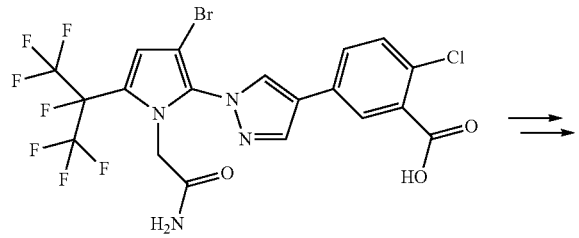

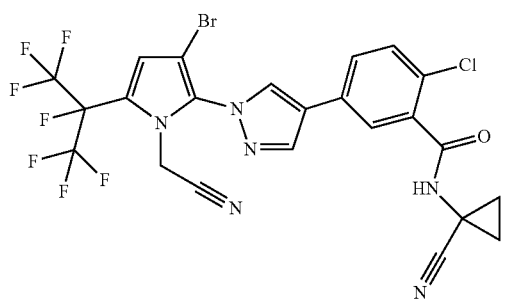

Hydrolysis and amide coupling were performed as described for above examples. The amido group was converted back to the cyano group under the reaction conditions.

¹H NMR (400 MHz, CDCl₃) δ ppm 1.44 (m, 2H), 1.71 (m, 2H), 5.05 (d, J=1.1 Hz, 2H), 6.77 (s, 1H), 6.89 (s, 1H), 7.47 (d, J=8.4 Hz, 1H), 7.60 (dd, J=8.4, 2.2 Hz, 1H), 7.97 (d, J=2.2 Hz, 1H), 8.10 (s, 1H), 8.18 (s, 1H).

¹⁹F NMR (376 MHz, CDCl₃) δ ppm −179.47 (s, 1F), −75.33 (s, 6F).

LC-MS (Method A): $t_R$=1.11 min, m/z=635 [M−1], 637 [M+1].

Example 14: 5-[1-[3-bromo-1-(methoxymethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide

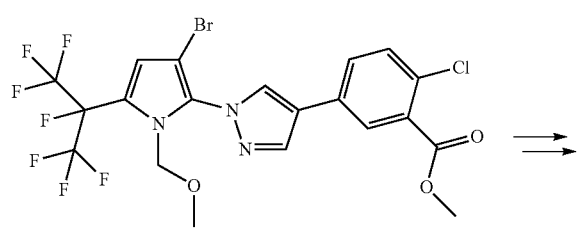

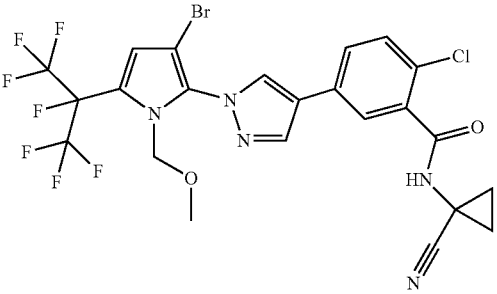

Hydrolysis and amide coupling were performed as described for above examples.

¹H NMR (400 MHz, CDCl₃) δ ppm 1.43 (m, 2H), 1.71 (m, 2H), 3.15 (s, 3H), 5.25 (s, 2H), 6.69 (s, 1H), 6.91 (s, 1H), 7.45 (d, J=8.4 Hz, 1H), 7.59 (dd, J=8.4, 2.2 Hz, 1H), 7.97 (d, J=2.2 Hz, 1H), 7.99 (s, 1H), 8.12 (s, 1H).

¹⁹F NMR (376 MHz, CDCl₃) δ ppm −181.56 (s, 1F), −75.76 (s, 6F).

LC-MS (Method A): $t_R$=1.15 min, m/z=640 [M−1], 642 [M+1].

Example 15: 2-chloro-N-(1-cyanocyclopropyl)-5-[1-(3,4,5-tribromo-1-methyl-pyrrol-2-yl)pyrazol-4-yl]benzamide a) Preparation of methyl 2-chloro-5-[1-(3,4,5-tribromo-1-methyl-pyrrol-2-yl)pyrazol-4-yl]benzoate

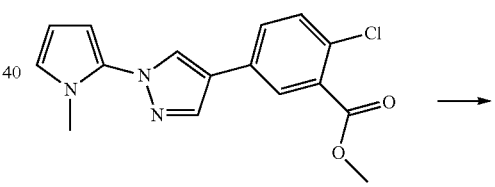

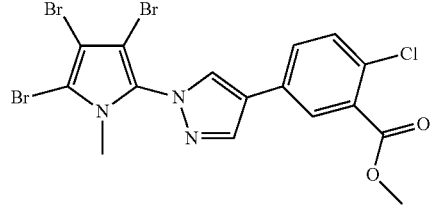

To a stirred solution of methyl 2-chloro-5-[1-(1-methylpyrrol-2-yl)pyrazol-4-yl]benzoate (0.32 g, 1.0 mmol) in acetonitrile (5 mL) was added N-bromosuccinimide (0.76 g, 4.3 mmol) at −10° C. The reaction mixture was stirred for 30 min at −10° C. The reaction mixture was filtered, the product was washed with acetonitrile and dried to afford the desired compound as a white solid.

¹H NMR (400 MHz, CDCl₃) δ ppm 3.50 (s, 3H), 3.98 (s, 3H), 7.50 (d, J=8.4 Hz, 1H), 7.58 (dd, J=8.4, 2.2 Hz, 1H), 7.89 (s, 1H), 7.99 (d, J=2.2 Hz, 1H), 8.08 (s, 1H).

LC-MS (Method A): $t_R$=1.23 min, m/z=550 [M+1]

b) Preparation of 2-chloro-N-(1-cyanocyclopropyl)-5-[1-(3,4,5-tribromo-1-methyl-pyrrol-2-yl)pyrazol-4-yl]benzamide

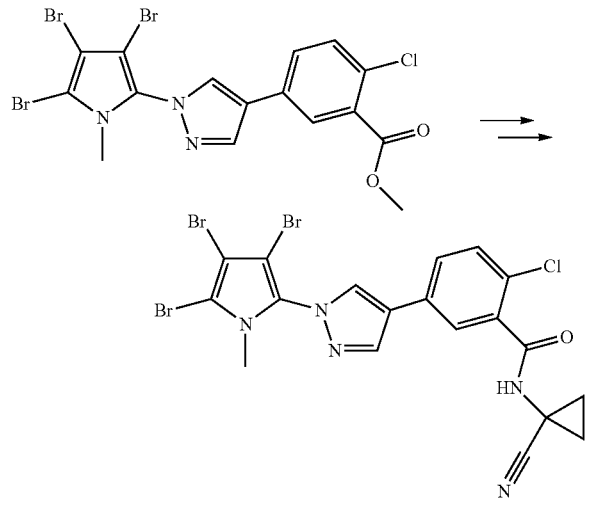

Hydrolysis and amide coupling were performed as described for above examples.

¹H NMR (400 MHz, CDCl₃) δ ppm 1.43 (m, 2H), 1.71 (m, 2H), 3.50 (s, 3H), 6.90 (s, 1H), 7.45 (d, J=8.4 Hz, 1H), 7.58 (dd, J=8.4, 2.2 Hz, 1H), 7.91 (s, 1H), 7.96 (d, J=2.2 Hz, 1H), 8.08 (s, 1H).

LC-MS (Method A): t$_R$=1.08 min, m/z=598 [M−1], 600 [M+1].

Example 16: 2-chloro-N-(1-cyanocyclopropyl)-5-[1-[3,4-dibromo-1-methyl-5-(trifluoromethylsulfanyl)pyrrol-2-yl]pyrazol-4-yl]benzamide a) Preparation of methyl 2-chloro-5-[1-[3,4-dibromo-1-methyl-5-(trifluoromethylsulfanyl)pyrrol-2-yl]pyrazol-4-yl]benzoate

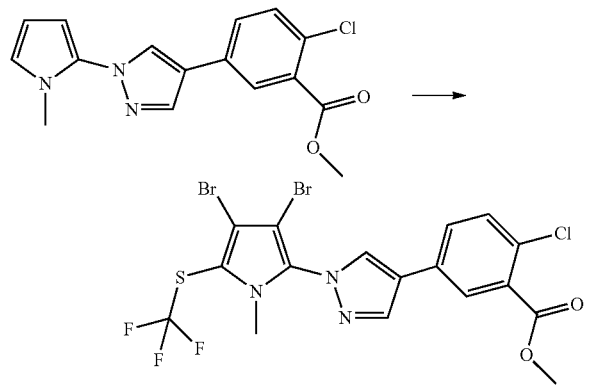

A mixture of methyl 2-chloro-5-[1-(1-methylpyrrol-2-yl)pyrazol-4-yl]benzoate (0.079 g, 0.25 mmol), N-Trifluoromethylthiosaccharin (0.092 g, 0.315 mmol) and DMF (0.5 g) was stirred at 65° C. for 2 h. The mixture was cooled to room temperature followed by the addition of N-bromosuccinimide (0.112 g, 0.60 mmol). The reaction mixture was stirred overnight at room temperature.

MTBE (5 mL), water (5 mL) and saturated sodium bicarbonate solution (2 mL) were added to the reaction mixture. The organic phase was separated and evaporated to dryness. The remaining crude product was purified by flash chromatography (silica, cyclohexane/gradient of ethyl acetate from 0 to 20%).

¹H NMR (400 MHz, CDCl₃) δ ppm 3.67 (s, 3H), 3.98 (s, 3H), 7.51 (d, J=8.4 Hz, 1H), 7.59 (dd, J=8.4, 2.2 Hz, 1H), 7.97 (s, 1H), 8.00 (d, J=2.2 Hz, 1H), 8.11 (s, 1H).

¹⁹F NMR (376 MHz, CDCl₃) δ ppm −43.13.

LC-MS (Method A): t$_R$=1.28 min, m/z=572 [M+1].

b) Preparation of 2-chloro-N-(1-cyanocyclopropyl)-5-[1-[3,4-dibromo-1-methyl-5-(trifluoromethylsulfanyl)pyrrol-2-yl]pyrazol-4-yl]benzamide

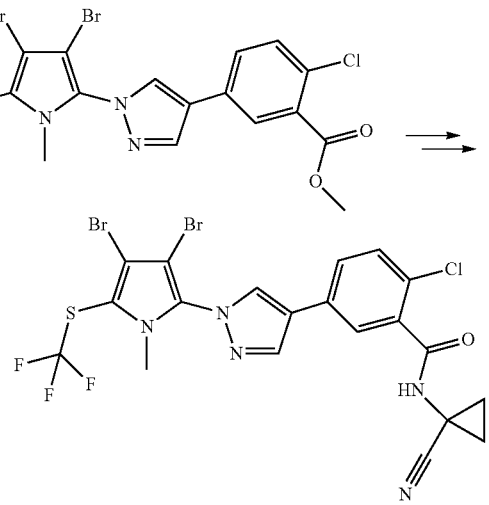

Hydrolysis and amide coupling were performed as described for above examples.

¹H NMR (400 MHz, CDCl₃) δ ppm 1.44 (m, 2H), 1.71 (m, 2H), 3.67 (s, 3H), 6.90 (s, 1H), 7.46 (d, J=8.4 Hz, 1H), 7.59 (dd, J=8.4, 2.2 Hz, 1H), 7.98 (d, J=2.2 Hz, 1H), 7.99 (s, 1H), 8.11 (s, 1H).

¹⁹F NMR (376 MHz, CDCl₃) δ ppm −43.11.

LC-MS (Method A): t$_R$=1.15 min, m/z=620 [M−1], 622 [M+1].

Example 17: 5-[1-[3-bromo-5-[1-(3,5-difluorophenyl)-1,2,2,2-tetrafluoro-ethyl]-1-methyl-pyrrol-2-yl]pyrazol-4-yl]-2-chloro-N-(1-cyanocyclopropyl)benzamide a) Preparation of methyl 2-chloro-5-[1-[1-methyl-5-(2,2,2-trifluoroacetyl)pyrrol-2-yl]pyrazol-4-yl]benzoate

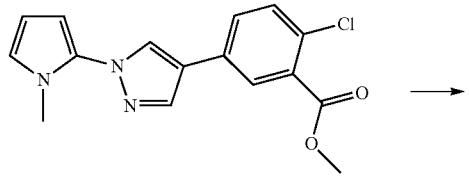

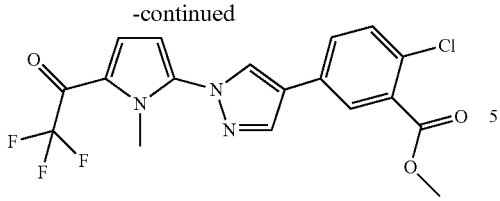

To a stirred mixture of methyl 2-chloro-5-[1-(1-methylpyrrol-2-yl)pyrazol-4-yl]benzoate (0.904 g, 2.86 mmol), pyridine (0.453 g, 5.73 mmol) and dichloromethane (8.0 g) was added trifluoroacetic anhydride (0.72 g, 3.44 mmol) dropwise within 5 min at 0-5° C. The reaction mixture was allowed to reach room temperature.

Water (10 g) and dichloromethane (5 mL) was added to the mixture. The organic phase was separated, washed with water (10 mL) and evaporated to result in a viscous oil which then solidified upon standing.

$^1$H NMR (400 MHz, CDCl$_3$) δ ppm 3.97 (s, 3H), 4.00 (s, 3H), 6.40 (d, J=4.6, 1H), 7.31 (m, 1H), 7.52 (d, J=8.4 Hz, 1H), 7.60 (dd, J=8.4, 2.2 Hz, 1H), 7.97 (s, 1H), 8.01 (d, J=2.2 Hz, 1H), 8.11 (s, 1H).

$^{19}$F NMR (376 MHz, CDCl$_3$) δ ppm −71.28 (s).

LC-MS (Method A): t$_R$=1.17 min, m/z=412 [M+1].

b) Preparation of methyl 5-[1-[3-bromo-1-methyl-5-(2,2,2-trifluoroacetyl)pyrrol-2-yl]pyrazol-4-yl]-2-chloro-benzoate

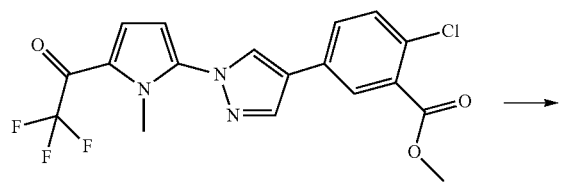

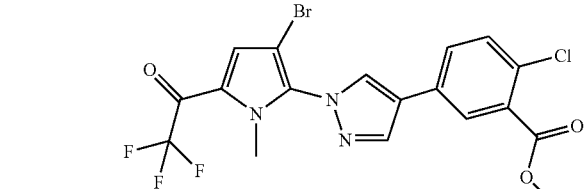

To a stirred solution of methyl 2-chloro-5-[1-[1-methyl-5-(2,2,2-trifluoroacetyl)pyrrol-2-yl]pyrazol-4-yl]benzoate (1.05 g, 2.55 mmol) in acetonitrile (5.0 g) was added N-bromosuccinimide (0.527 g, 2.93 mmol) in one portion at room temperature. The mixture was stirred for 1.5 h at room temperature. Water (20 mL) and ethyl acetate (20 mL) was added to the mixture. The organic phase was separated, washed with 5% sodium bicarbonate solution (20 mL), then with water (20 mL), dried over magnesium sulfate and evaporated to afford a crystalline material.

$^1$H NMR (400 MHz, CDCl$_3$) δ ppm 3.87 (s, 3H), 3.99 (s, 3H), 7.32 (m, 1H), 7.52 (d, J=8.4 Hz, 1H), 7.60 (dd, J=8.4, 2.2 Hz, 1H), 8.01 (m, 2H), 8.15 (d, J=0.7 Hz, 1H).

$^{19}$F NMR (376 MHz, CDCl$_3$) δ ppm −71.67 (s).

LC-MS (Method A): t$_R$=1.21 min, m/z=488 [M−1], 490 [M+1].

c) Preparation of methyl 5-[1-[3-bromo-5-[1-(3,5-difluorophenyl)-2,2,2-trifluoro-1-hydroxy-ethyl]-1-methyl-pyrrol-2-yl]pyrazol-4-yl]-2-chloro-benzoate

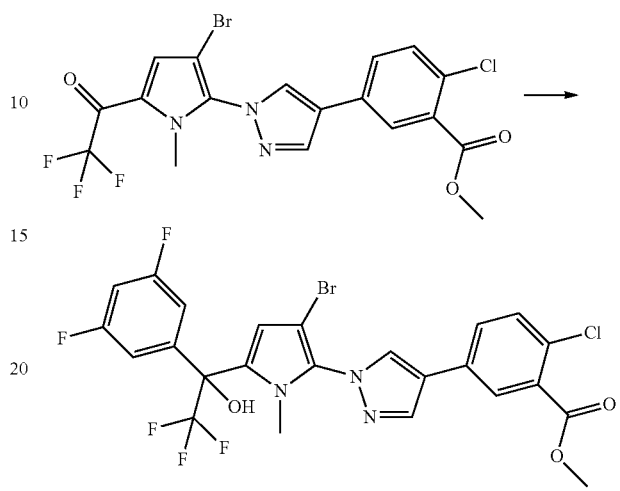

To a stirred solution of 5-[1-[3-bromo-1-methyl-5-(2,2,2-trifluoroacetyl)pyrrol-2-yl]pyrazol-4-yl]-2-chloro-benzoate (0.164 g, 0.333 mmol) in anhydrous THF (0.9 g) was added 3,5-Difluorophenylmagnesium bromide 0.5M solution in THF (0.73 mL, 0.367 mmol) dropwise at 0° C. under argon. The mixture was allowed to warm up to room temperature.

The reaction mixture was acidified with 1N HCl (2 mL), diluted with water (2 mL) and cyclohexane (3 mL) was added. The organic phase was separated, dried over magnesium sulfate and evaporated to afford an amorphous solid (foam) which was used in the next step as is.

LC-MS (Method A): t$_R$=1.24 min, m/z=602 [M−1], 604 [M+1].

d) Preparation of methyl 5-[1-[3-bromo-5-[1-(3,5-difluorophenyl)-1,2,2,2-tetrafluoro-ethyl]-1-methyl-pyrrol-2-yl]pyrazol-4-yl]-2-chloro-benzoate

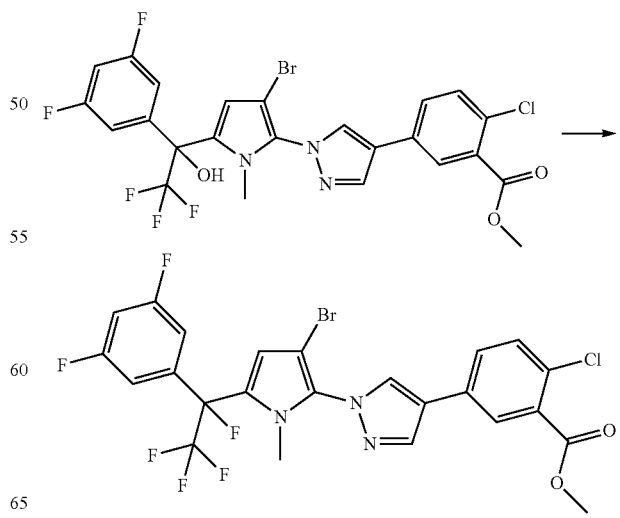

To a stirred solution of 5-[1-[3-bromo-5-[1-(3,5-difluorophenyl)-2,2,2-trifluoro-1-hydroxy-ethyl]-1-methyl-pyrrol-2-yl]pyrazol-4-yl]-2-chloro-benzoate (0.194 g, 0.320 mmol) in toluene (1.0 mL) was added Deoxo-Fluor® 50% solution in toluene (0.31 g, 0.70 mmol) at room temperature under argon. The mixture was stirred for 2 h at room temperature.

The reaction mixture was quenched with sodium bicarbonate 5% solution. The organic phase was separated and evaporated to give a crude product which was purified by flash chromatography (silica, cyclohexane/gradient of ethyl acetate from 0 to 20%).

$^1$H NMR (400 MHz, CDCl$_3$) δ ppm 3.10 (d, J=1.1 Hz, 3H), 3.97 (s, 3H), 6.70 (m, 1H), 6.92-7.01 (m, 3H), 7.49 (d, J=8.4 Hz, 1H), 7.58 (dd, J=8.4, 2.2 Hz, 1H), 7.94 (s, 1H), 7.99 (d, J=2.2 Hz, 1H), 8.06 (s, 1H).

$^{19}$F NMR (376 MHz, CDCl$_3$) δ ppm −154.62 (q, 1F), −106.72 (d, 2F), −75.91 (d, 3F).

LC-MS (Method A): $t_R$=1.32 min, m/z=606 [M+1].

e) Preparation of 5-[1-[3-bromo-5-[1-(3,5-difluorophenyl)-1,2,2,2-tetrafluoro-ethyl]-1-methyl-pyrrol-2-yl]pyrazol-4-yl]-2-chloro-N-(1-cyanocyclopropyl)benzamide

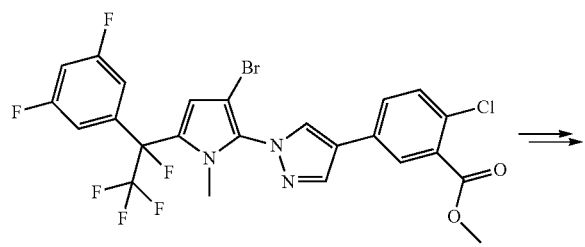

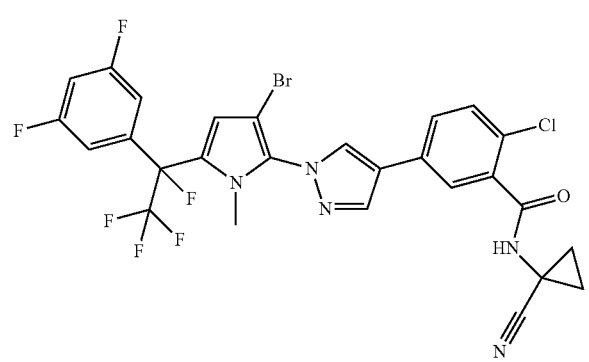

Hydrolysis and amide coupling were performed as described for above examples.

$^1$H NMR (400 MHz, CDCl$_3$) δ ppm 1.43 (m, 2H), 1.70 (m, 2H), 3.10 (d, J=1.1 Hz, 3H), 6.70 (m, 1H), 6.90 (s, 1H), 6.92-7.01 (m, 3H), 7.44 (d, J=8.4 Hz, 1H), 7.57 (dd, J=8.4, 2.2 Hz, 1H), 7.95 (m, 2H), 8.06 (s, 1H).

$^{19}$F NMR (376 MHz, CDCl$_3$) δ ppm −154.60 (q, 1F), −106.70 (d, 2F), −75.89 (d, 3F).

LC-MS (Method A): $t_R$=1.20 min, m/z=654 [M−1], 656 [M+1].

Example 18: 5-[1-[3-chloro-1-methyl-5-[1,2,2,2-tetrafluoro-1-(trifluoromethyl)ethyl]pyrrol-2-yl]pyrazol-4-yl]-2-cyano-N-cyclopropyl-thiophene-3-carboxamide a) Preparation of methyl 2-cyano-5-[1-[1-methyl-5-[1,2,2,2-tetrafluoro-1-(trifluoromethyl)ethyl]pyrrol-2-yl]pyrazol-4-yl]thiophene-3-carboxylate

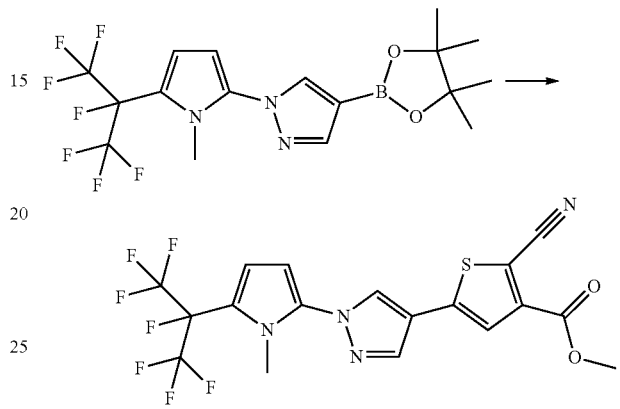

A vial was charged with 1-[1-methyl-5-[1,2,2,2-tetrafluoro-1-(trifluoromethyl)ethyl]pyrrol-2-yl]-4-(4,4,5,5-tetramethyl-1,3,2-dioxaborolan-2-yl)pyrazole (1.0 g, 2.3 mmol, see Example 19 c)), methyl 5-bromo-2-cyano-thiophene-3-carboxylate (0.70 g, 2.8 mmol), potassium bicarbonate (0.78 g, 5.7 mmol), N,N-dimethylformamide (8.9 g) and water (2.3 g). The mixture was purged with argon followed by the addition of Pd(PPh$_3$)$_4$ (0.26 g, 0.23 mmol). The vial was sealed up and heated to 80° C. for 1.5 h. After cooling to room temperature, the reaction mixture was diluted with water and extracted with ethyl acetate. The organic layer was consecutively washed with water and brine, dried over magnesium sulfate and evaporated. The crude product was purified by flash chromatography (silica, cyclohexane/gradient of ethyl acetate from 0 to 30%).

$^1$H NMR (400 MHz, CDCl$_3$) δ ppm 3.58 (d, J=3.7 Hz, 3H), 4.00 (s, 3H), 6.35 (d, J=4.2 Hz, 1H), 6.60 (m, 1H), 7.60 (s, 1H), 7.92 (s, 1H), 8.02 (s, 1H), 8.04 (m, 1H).

$^{19}$F NMR (376 MHz, CDCl$_3$) δ ppm −179.40 (s, 1F), −75.30 (s, 6F).

LC-MS (Method A): $t_R$=1.22 min, m/z=481 [M+1].

b) Preparation of methyl 5-[1-[3-chloro-1-methyl-5-[1,2,2,2-tetrafluoro-1-(trifluoromethyl)ethyl]pyrrol-2-yl]pyrazol-4-yl]-2-cyano-thiophene-3-carboxylate

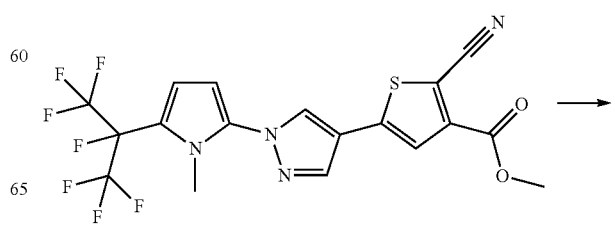

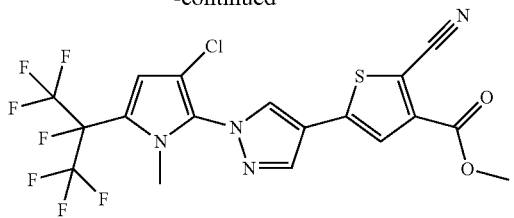

A mixture of methyl 2-cyano-5-[1-[1-methyl-5-[1,2,2,2-tetrafluoro-1-(trifluoromethyl)ethyl]pyrrol-2-yl]pyrazol-4-yl]thiophene-3-carboxylate (0.050 g, 0.1 mmol), N-chlorosuccinimide (0.015 g, 0.11 mmol) and DMF (0.49 g) was stirred overnight at room temperature. The product was isolated by preparative reversed phase chromatography.
LC-MS (Method A): $t_R$=1.25 min, m/z=515 [M+1].

c) Preparation of 5-[1-[3-chloro-1-methyl-5-[1,2,2,2-tetrafluoro-1-(trifluoromethyl)ethyl]pyrrol-2-yl]pyrazol-4-yl]-2-cyano-N-cyclopropyl-thiophene-3-carboxamide

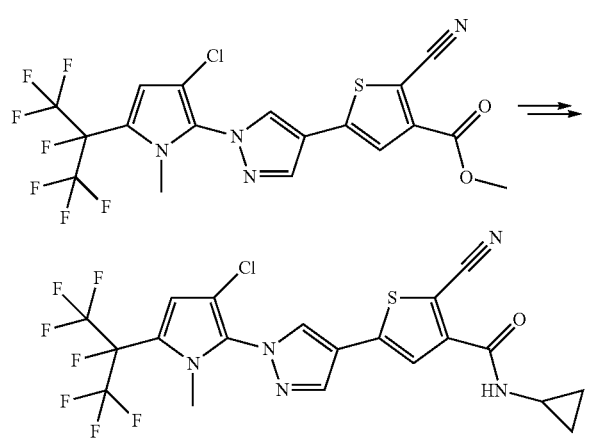

Hydrolysis and amide coupling were performed as described for above examples.
$^1$H NMR (400 MHz, CDCl$_3$) δ ppm 0.71 (m, 2H), 0.93 (m, 2H), 2.95 (m, 1H), 3.56 (d, J=3.7 Hz, 3H), 6.51 (s, 1H), 6.59 (s, 1H), 7.58 (s, 1H), 7.96 (s, 1H), 8.05 (s, 1H).
$^{19}$F NMR (376 MHz, CDCl$_3$) δ ppm −180.12 (s, 1F), −75.31 (s, 6F).
LC-MS (Method A): $t_R$=1.17 min, m/z=538 [M−1], 540 [M+1].

Example 19: 2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)pyridine-3-carboxamide a) Preparation of 4-bromo-1-(1-methylpyrrol-2-yl)pyrazole

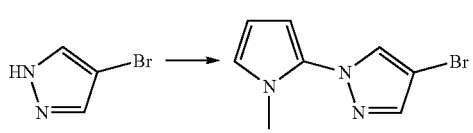

To a stirred mixture of 4-bromo-1H-pyrazole (10.0 g, 68.0 mmol), 1-methylpyrrole (13.9 g, 170 mmol), sodium bicarbonate (5.72 g, 68.0 mmol), acetonitrile (69 g) and water (27 g) was added 5% sodium hypochlorite solution (140 mL, 108 mmol) dropwise within 20 min while keeping the temperature at 35° C. After the addition was completed, the mixture was stirred for 30 min at 30° C.
The reaction mixture was diluted with TBME (200 mL). The organic phase was separated and evaporated to give the crude product which was purified by flash chromatography (silica, cyclohexane/gradient of ethyl acetate from 5 to 10%).
$^1$H NMR (400 MHz, CDCl$_3$) δ ppm 3.49 (s, 3H), 6.16 (m, 2H), 6.61 (m, 1H), 7.61 (s, 1H), 7.69 (s, 1H).
LC-MS (Method A): $t_R$=0.93 min, m/z=226 [M+1]

b) Preparation of 4-bromo-1-[1-methyl-5-[1,2,2,2-tetrafluoro-1-(trifluoromethyl)ethyl]pyrrol-2-yl]pyrazole

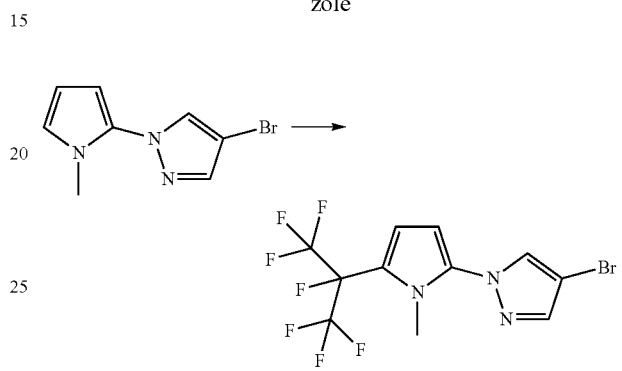

To a stirred mixture of 4-bromo-1-(1-methylpyrrol-2-yl)pyrazole (0.62 g, 2.74 mmol), 1,1,1,2,3,3,3-heptafluoro-2-iodo-propane (0.893 g, 3.02 mmol), iron(II) sulfate heptahydrate (0.15 g, 0.55 mmol) and dimethyl sulfoxide (5.0 g) was added 30% hydrogen peroxide solution (0.62 g, 5.5 mmol) dropwise within 15 min while keeping the temperature at 55-60° C. The mixture was kept at 60° C. for 10 min and then allowed to cool slowly to room temperature.
The reaction mixture was diluted with water (20 g) and extracted with a cyclohexane/ethyl acetate mixture=1:1 (20 mL). The extract was washed 3 times with water (3*15 mL), dried over magnesium sulfate and evaporated to give the title compound as a yellow oil.
$^1$H NMR (400 MHz, CDCl$_3$) δ ppm 3.50 (d, J=3.3 Hz, 3H), 6.28 (dd, J=4.2, 1.3 Hz, 1H), 6.55 (m, 1H), 7.65 (s, 1H), 7.74 (s, 1H).
$^{19}$F NMR (376 MHz, CDCl$_3$) δ ppm −179.31 (s, 1F), −75.32 (s, 6F).
LC-MS (Method A): $t_R$=1.20 min, m/z=394 [M+1].

c) Preparation of 1-[1-methyl-5-[1,2,2,2-tetrafluoro-1-(trifluoromethyl)ethyl]pyrrol-2-yl]-4-(4,4,5,5-tetramethyl-1,3,2-dioxaborolan-2-yl)pyrazole

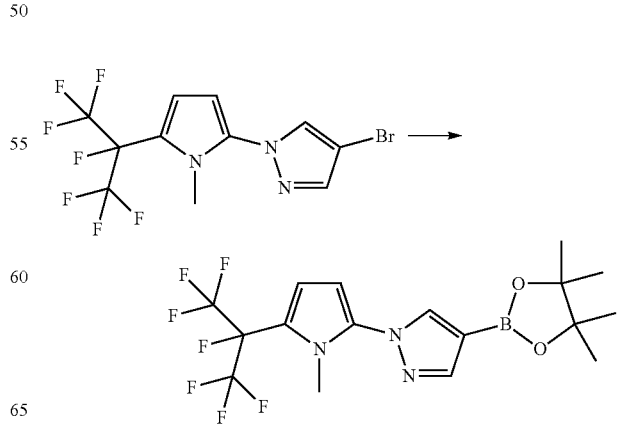

A microwave tube was charged with 4-bromo-1-[1-methyl-5-[1,2,2,2-tetrafluoro-1-(trifluoromethyl)ethyl]pyrrol-2-yl]pyrazole (3.5 g, 8.9 mmol), Bis(pinacolato)diboron (2.7 g, 11.0 mmol), potassium acetate (2.6 g, 27 mmol) and anhydrous dioxane (18 mL). The tube was purged with argon followed by the addition of Pd(PPh$_3$)$_4$ (0.51 g, 0.44 mmol). The tube was sealed up and heated in a microwave reactor to 120° C. for 45 min.

After cooling to room temperature, water and ethyl acetate were added to the reaction mixture and the resulting byphasic system was filtered over a celite pad. The organic layer was separated, consecutively washed with water and brine, dried over magnesium sulfate and evaporated. The crude product was purified by flash chromatography (silica, cyclohexane/gradient of ethyl acetate from 0 to 10%).

$^1$H NMR (400 MHz, CDCl$_3$) δ ppm 1.35 (s, 12H), 3.50 (d, J=3.3 Hz, 3H), 6.25 (dd, J=4.2, 1.3 Hz, 1H), 6.54 (m, 1H), 7.90 (s, 1H), 8.02 (s, 1H).

$^{19}$F NMR (376 MHz, CDCl$_3$) δ ppm −179.02 (s, 1F), −75.31 (s, 6F).

LC-MS (Method A): t$_R$=1.26 min, m/z=442 [M+1].

d) Preparation of methyl 2-chloro-5-[1-[1-methyl-5-[1,2,2,2-tetrafluoro-1-(trifluoromethyl)ethyl]pyrrol-2-yl]pyrazol-4-yl]pyridine-3-carboxylate

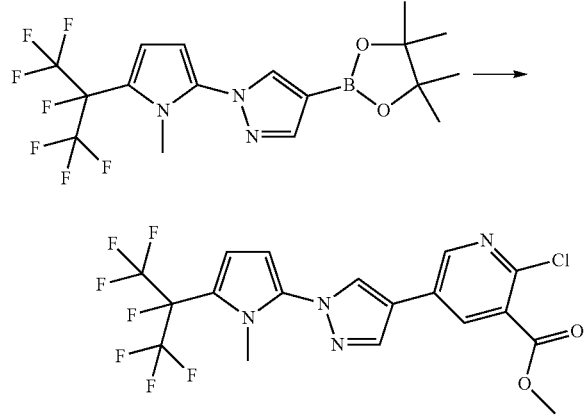

A microwave tube was charged with 1-[1-methyl-5-[1,2,2,2-tetrafluoro-1-(trifluoromethyl)ethyl]pyrrol-2-yl]-4-(4,4,5,5-tetramethyl-1,3,2-dioxaborolan-2-yl)pyrazole (1.1 g, 2.5 mmol), methyl 5-bromo-2-chloro-pyridine-3-carboxylate (0.78 g, 3.1 mmol), potassium bicarbonate (0.86 g, 6.2 mmol), N,N-dimethylformamide (9.8 g) and water (2.5 g). The tube was purged with argon followed by the addition of Pd(PPh$_3$)$_4$ (0.29 g, 0.25 mmol). The tube was sealed up and heated in a microwave reactor to 80° C. for 2 h.

After cooling to room temperature, the reaction mixture was diluted with water and extracted with ethyl acetate. The organic layer was consecutively washed twice with water and brine, dried over magnesium sulfate and evaporated. The crude product was purified by flash chromatography (silica, cyclohexane/gradient of ethyl acetate from 0 to 20%).

LC-MS (Method A): t$_R$=1.19 min, m/z=485 [M+1].

e) Preparation of 2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)pyridine-3-carboxamide

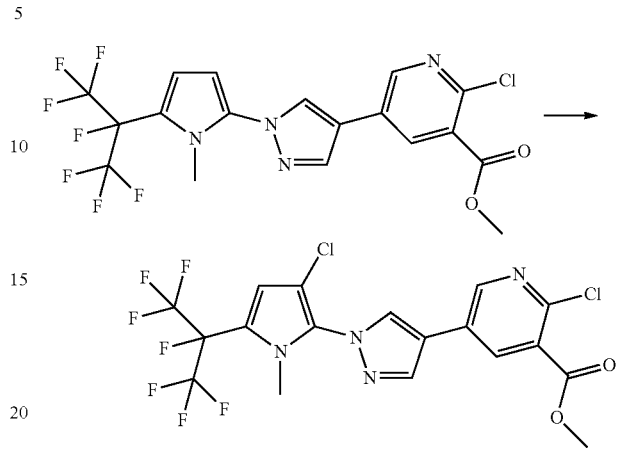

A mixture of 2-chloro-5-[1-[1-methyl-5-[1,2,2,2-tetrafluoro-1-(trifluoromethyl)ethyl]pyrrol-2-yl]pyrazol-4-yl]pyridine-3-carboxylate (0.050 g, 0.1 mmol), N-chlorosuccinimide (0.015 g, 0.11 mmol) and DMF (0.49 g) was stirred overnight at room temperature. The product was isolated by preparative reversed phase chromatography.

LC-MS (Method A): t$_R$=1.22 min, m/z=519 [M+1].

f) Preparation of methyl 2-chloro-5-[1-[3-chloro-1-methyl-5-[1,2,2,2-tetrafluoro-1-(trifluoromethyl)ethyl]pyrrol-2-yl]pyrazol-4-yl]pyridine-3-carboxylate

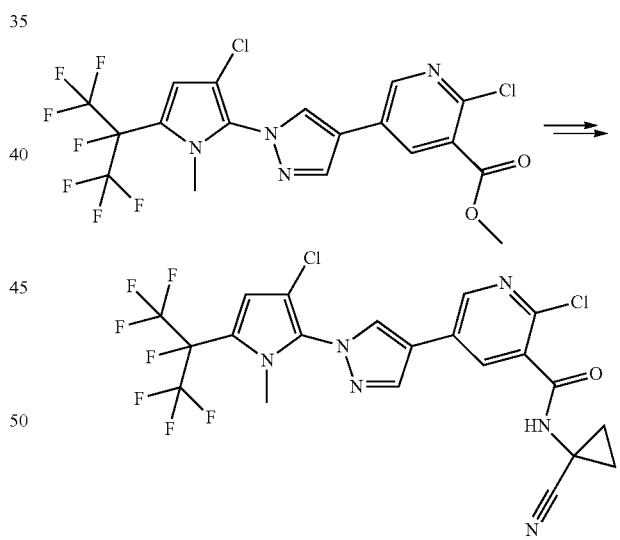

Hydrolysis and amide coupling were performed as described for above examples.

$^1$H NMR (400 MHz, CDCl$_3$) δ ppm 1.45 (m, 2H), 1.73 (m, 2H), 3.57 (d, J=3.7 Hz, 3H), 6.60 (s, 1H), 7.19 (s, 1H), 8.04 (s, 1H), 8.17 (s, 1H), 8.39 (d, J=2.2 Hz, 1H), 8.70 (d, J=2.2 Hz, 1H).

$^{19}$F NMR (376 MHz, CDCl$_3$) δ ppm −180.03 (s, 1F), −75.31 (s, 6F).

LC-MS (Method A): t$_R$=1.11 min, m/z=567 [M−1], 569 [M+1].

The following compounds in Table 1 may be prepared in analogy with Example 1 or according to known literature methods or according to methods described in WO2012/

107434, WO2014/122083, WO2015/067646, WO2015/150442, WO2015/193218 and WO2017/012970.
TABLE 1
| Structure | LCMS |
|---|---|
| 1 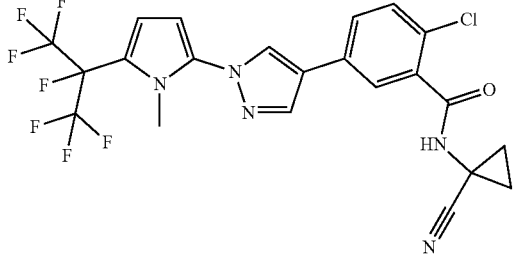 | (Method A): $t_R$ = 1.12 min, m/z = 534 [M + 1]. |
| 2 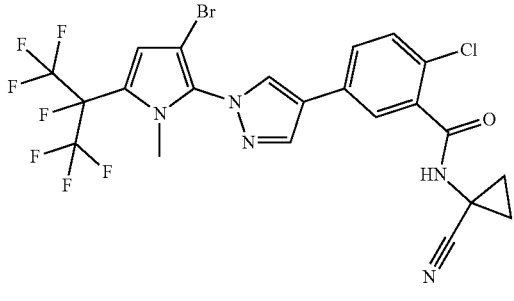 [SMILES: Cn1c(C(F)(C(F)(F)F)C(F)(F)F)cc(Br)c1-n1cc(-c2ccc(Cl)c(C(=O)NC3(C#N)CC3)c2)cn1] | (Method A): $t_R$ = 1.16 min, m/z = 612 [M + 1], 614 [M + 3]. |
| 3 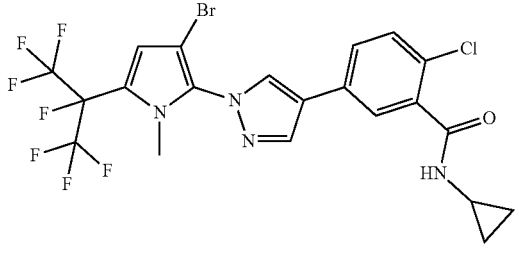 [SMILES: Cn1c(C(F)(C(F)(F)F)C(F)(F)F)cc(Br)c1-n1cc(-c2ccc(Cl)c(C(=O)NC3CC3)c2)cn1] | (Method A): $t_R$ = 1.17 min, m/z = 587 [M + 1], 589 [M + 3]. |
| 4 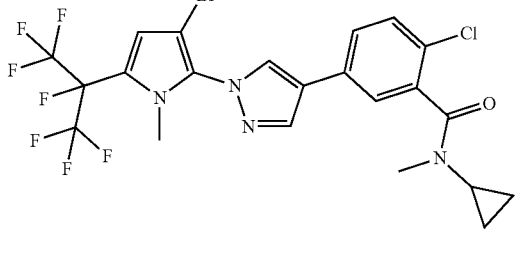 | (Method A): $t_R$ = 1.24 min, m/z = 601 [M + 1], 603 [M + 3]. |
| 5 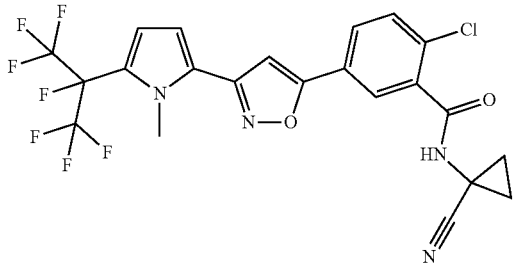 [SMILES: Cn1c(-c2cc(-c3ccc(Cl)c(C(=O)NC4(C#N)CC4)c3)on2)ccc1C(F)(C(F)(F)F)C(F)(F)F] | (Method A): $t_R$ = 1.18 min, m/z = 535 [M + 1]. |

TABLE 1-continued

| Structure | LCMS |
|---|---|
| 6 | (Method A): $t_R$ = 1.21 min, m/z = 613 [M + 1], 615 [M + 3]. |
| 7 | (Method A): $t_R$ = 1.10 min, m/z = 579 [M + 1]. |
| 8 | (Method A): $t_R$ = 1.15 min, m/z = 502 [M + 1]. |
| 9 | (Method A): $t_R$ = 1.15 min, m/z = 568 [M + 1]. |
| 10 | (Method A): $t_R$ = 1.09 min, m/z = 559 [M + 1]. |

TABLE 1-continued

| Structure | LCMS |
|---|---|
| 11 | (Method A): $t_R$ = 1.15 min, m/z = 548 [M + 1]. |
| 12 | (Method A): $t_R$ = 1.14 min, m/z = 630 [M + 1], 632 [M + 3]. |
| 13 | (Method A): $t_R$ = 1.11 min, m/z = 637 [M + 1], 639 [M + 3]. |
| 14 | (Method A): $t_R$ = 1.15 min, m/z = 642 [M + 1], 644 [M + 3]. |
| 15 | (Method A): $t_R$ = 1.08 min, m/z = 600 [M + 1], 602 [M + 3], 604 [M + 5]. |

TABLE 1-continued

| Structure | LCMS |
|---|---|
| 16 | (Method A): $t_R$ = 1.15 min, m/z = 622 [M + 1], 624 [M + 3]. |
| 17 | (Method A): $t_R$ = 1.20 min, m/z = 658 [M + 1]. |
| 18 | (Method A): $t_R$ = 1.17 min, m/z = 540 [M + 1]. |
| 19 | (Method A): $t_R$ = 1.11 min, m/z = 569 [M + 1]. |
| 20 | (Method A): $t_R$ = 1.24 min, m/z = 640 [M + 1], 642 [M + 3]. |

TABLE 1-continued

| Structure | LCMS |
|---|---|
| 21 (structure) | (Method A): $t_R$ = 1.21 min, m/z = 626 [M + 1], 628 [M + 3]. |
| 22 (structure) | (Method A): $t_R$ = 1.21 min, m/z = 615 [M + 1], 617 [M + 3]. |
| 23 (structure) | (Method A): $t_R$ = 1.21 min, m/z = 593 [M + 1], 595 [M + 3]. |
| 24 (structure) | (Method A): $t_R$ = 1.22 min, m/z = 640 [M + 1], 642 [M + 3]. |
| 25 (structure) | (Method A): $t_R$ = 1.23 min, m/z = 654 [M + 1], 656 [M + 3]. |
| 26 (structure) | (Method A): $t_R$ = 1.20 min, m/z = 680 [M + 1], 682 [M + 3]. |

TABLE 1-continued
| Structure | LCMS |
|---|---|
| 27 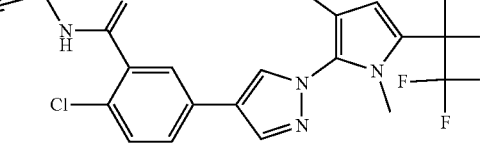 | (Method A): $t_R$ = 1.20 min, m/z = 662 [M + 1], 664 [M + 3]. |
| 28  | (Method A): $t_R$ = 1.17 min, m/z = 584 [M + 1]. |
| 29 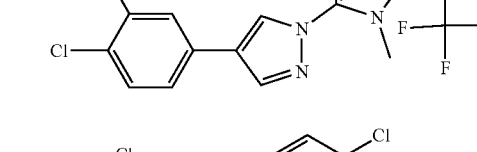 | (Method A): $t_R$ = 1.14 min, m/z = 586 [M + 1]. |
| 30 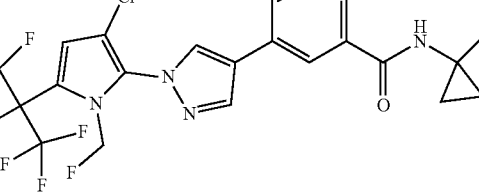 | (Method A): $t_R$ = 1.28 min, m/z = 644 [M + 1], 646 [M + 3]. |
| 31  | (Method A): $t_R$ = 1.12 min, m/z = 562 [M + 1], 564 [M + 3]. |
| 32 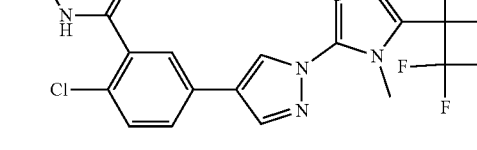 | (Method A): $t_R$ = 1.06 min, m/z = 498 [M − 1]. |

TABLE 1-continued
| Structure | LCMS |
|---|---|
| 33 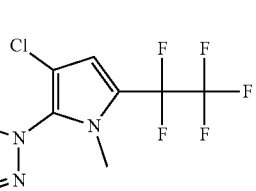 | (Method A): $t_R$ = 1.08 min, m/z = 516 [M − 1]. |
| 34  | (Method A): $t_R$ = 1.16 min, m/z = 660 [M + 1]. |
| 35  | (Method A): $t_R$ = 1.26 min, m/z = 660 [M + 1]. |
| 36 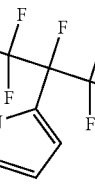 | (Method A): $t_R$ = 1.17 min, m/z = 562 [M + 1]. |
| 37 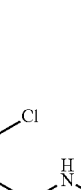 | (Method A): $t_R$ = 1.17 min, m/z = 562 [M + 1]. |

TABLE 1-continued

| Structure | LCMS |
|---|---|
| 38 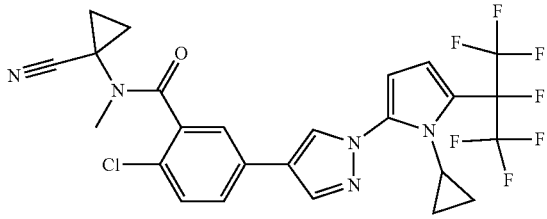 [SMILES: CN(C(=O)c1cc(-c2cnn(-c3ccc(C(F)(C(F)(F)F)C(F)(F)F)n3C3CC3)c2)ccc1Cl)C1(C#N)CC1] | (Method A): $t_R$ = 1.21 min, m/z = 574 [M + 1]. |
| 39 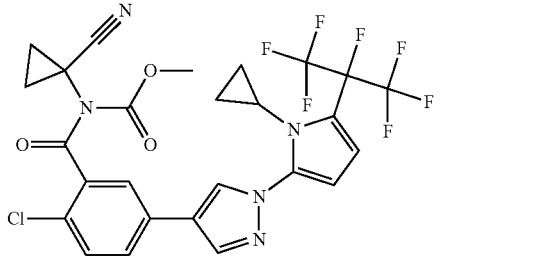 [SMILES: COC(=O)N(C(=O)c1cc(-c2cnn(-c3ccc(C(F)(C(F)(F)F)C(F)(F)F)n3C3CC3)c2)ccc1Cl)C1(C#N)CC1] | (Method A): $t_R$ = 1.24 min, m/z = 618 [M + 1]. |
| 40 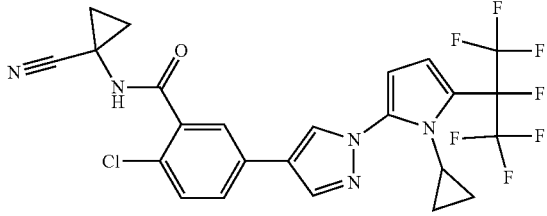 [SMILES: N#CC1(NC(=O)c2cc(-c3cnn(-c4ccc(C(F)(C(F)(F)F)C(F)(F)F)n4C4CC4)c3)ccc2Cl)CC1] | (Method A): $t_R$ = 1.15 min, m/z = 560 [M + 1]. |
| 41 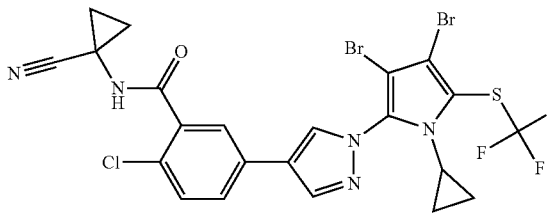 | (Method A): $t_R$ = 1.18 min, m/z = 648 [M + 1], 650 [M + 3]. |
| 42 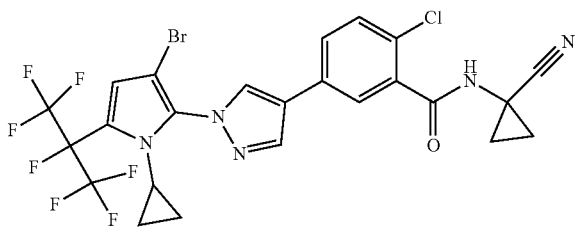 [SMILES: N#CC1(NC(=O)c2cc(-c3cnn(-c4c(Br)cc(C(F)(C(F)(F)F)C(F)(F)F)n4C4CC4)c3)ccc2Cl)CC1] | (Method A): $t_R$ = 1.19 min, m/z = 638 [M + 1], 640 [M + 3]. |

The activity of the compositions according to the invention can be broadened considerably, and adapted to prevailing circumstances, by adding other insecticidally, acaricidally and/or fungicidally active ingredients. The mixtures of the compounds according to any one of embodiments 1 to 24 with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds according to any one of embodiments 1 to 24 with active ingredients are preferred (the abbreviation "TX" means "one compound selected from the compounds according to any one of embodiments 1 to 24, preferably one compound from Table 1):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromo-cyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2, 13-dien-1-yl acetate (IUPAC name) (588)+TX, octadeca-3, 13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-1 1-en-1-yl acetate (IUPAC name) (785)+TX, trimedlure (839)+TX, trimedlure A (alternative name) (839)+TX, trimedlure B$_1$ (alternative name) (839)+TX, trimedlure B$_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2, 2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl) phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, ometthoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+

TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium* verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacrb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebucon-azole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimetho-morph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-

1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a, 12b-decahydro-6,12-dihydroxy-4,6a,12b-trimethyl-11-oxo-9-(3-pyridinyl)-2H, 11 Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright (c) 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds according to any one of embodiments 1 to 24 with active ingredients described above comprises a compound according to any one of embodiments 1 to 24 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of according to any one of embodiments 1 to 24 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds according to any one of embodiments 1 to 24 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound according to any one of embodiments 1 to 24. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with according to any one of embodiments 1 to 24. Further, it is hereby made available, a composition comprising a plant propagation material treated with a compound according to any one of embodiments 1 to 24.

Seed treatment comprises all suitable seed treatment techniques known in the art, such as seed dressing, seed coating, seed dusting, seed soaking and seed pelleting. The seed treatment application of the compound according to any one of embodiments 1 to 24 can be carried out by any known methods, such as spraying or by dusting the seeds before sowing or during the sowing/planting of the seeds.

Biological Data:

The pesticidal/insecticidal properties of the compounds according to any one of embodiments 1 to 24 can be illustrated via the following tests:

*Diabrotica balteata* (Corn root worm):

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality 4 days after infestation.

The following compounds resulted in at least 80% control at an application rate of 200 ppm: compounds 1, 2, 3, 4, 5, 6, 8, 9, 10, 11, 12, 13, 14, 15, 16, 17, 20, 21, 22, 23, 24, 25, 26, 27, 28, 29, 30, 31, 32, 33, 34, 41 and 42.

*Euschistus heros* (Neotropical Brown Stink Bug): Feeding/contact activity Soybean leaves on agar in 24-well microtiter plates were sprayed with aqueous test solutions prepared from 10,000 ppm DMSO stock solutions. After drying the leaves were infested with N2 nymphs. The samples were assessed for mortality 5 days after infestation.

The following compounds resulted in at least 80% control at an application rate of 200 ppm: compounds 1, 2, 3, 4, 5, 6, 8, 9, 10, 11, 12, 13, 14, 20, 21, 22, 23, 24, 25, 26, 27, 28, 29, 30, 31, 32, 33, 34, 35, 36, 37, 38, 39, 40, 41 and 42.

*Myzus persicae* (Green peach aphid): Feeding/Contact activity Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% control at an application rate of 200 ppm: compounds 1, 2, 4, 6, 9, 10, 12, 14, 20, 21, 22, 23, 24, 25, 26, 27, 28, 29, 31, 32, 33, 35, 36, 37, 38, 39 and 42.

*Plutella xylostella* (Diamond back moth): Feeding/contact activity 24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality 5 days after infestation.

The following compounds resulted in at least 80% control at an application rate of 200 ppm: compounds 1, 2, 3, 4, 5, 6, 8, 9, 10, 11, 12, 13, 14, 15, 16, 17, 20, 21, 22, 23, 24, 25, 26, 27, 28, 29, 30, 33, 34, 36, 37, 38, 40, 41 and 42.

*Spodoptera littoralis* (Egyptian cotton leaf worm): Feeding/contact activity Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality 3 days after infestation.

The following compounds resulted in at least 80% control at an application rate of 200 ppm: compounds 1, 2, 3, 4, 5, 6, 7, 8, 9, 10, 11, 12, 13, 14, 15, 16, 17, 20, 21, 22, 23, 24, 25, 26, 27, 28, 29, 30, 32, 33, 34, 35, 36, 37, 38, 39, 40, 41 and 42.

*Tetranychus urticae* (Two-spotted spider mite): Feeding/contact activity

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% control at an application rate of 200 ppm: compounds 1, 2, 3, 4, 5, 6, 9, 10, 11, 12, 13, 14, 16, 17, 20, 21, 22, 23, 24, 25, 26, 27, 28, 29, 31, 32, 33, 34, 35, 36, 37, 38, 39, 40, 41 and 42.

*Thrips tabaci* (Onion *Thrips*): Feeding/Contact activity

Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation.

The following compounds resulted in at least 80% control at an application rate of 200 ppm: compounds 2, 8, 9, 10, 11, 12, 16, 17, 20, 21, 24, 25, 26, 27, 28, 29, 30, 34 and 42.

The compounds according to any one of embodiments 1 to 24 can for example be distinguished from known compounds by virtue of greater efficacy at low application rates, which can be verified by the person skilled in the art using the experimental procedures outlined in the above biological tests, using lower application rates if necessary, for example 50 ppm, 12.5 ppm, δ ppm, 3 ppm, 1.5 ppm, 0.8 ppm or 0.2 ppm.

Furthermore, besides of the insecticidal properties, the compounds according to any one of embodiments 1 to 24 have surprisingly shown to have improved degradation properties compared with prior art compounds. Additionally, the compounds according to any one of embodiments 1 to 24 have surprisingly shown to be less toxic to bees compared with prior art compounds.

What is claimed is:

1. A compound of formula (I),

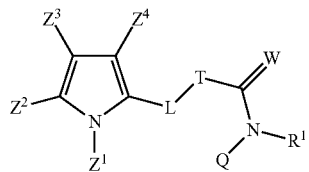

wherein

R$^1$ is selected from H, C$_1$-C$_6$-alkyl, C$_2$-C$_6$ alkenyl, C$_2$-C$_6$ alkynyl, —C$_0$-C$_3$-alkyl-C$_3$-C$_7$ cycloalkyl, —C(=O)—C$_1$-C$_6$-alkyl, —C(=O)—O—C$_1$-C$_6$-alkyl, —C(=O)—N—(C$_1$-C$_6$-alkyl)$_2$, —(C$_0$-C$_3$)-alkyl-aryl and —(C$_0$-C$_3$)-alkyl-heteroaryl, wherein each of C$_1$-C$_6$-alkyl, C$_2$-C$_6$ alkenyl, C$_2$-C$_6$ alkynyl, —C$_0$-C$_3$-alkyl-C$_3$-C$_7$ cycloalkyl, —C(=O)—C$_1$-C$_6$-alkyl, —C(=O)—O—C$_1$-C$_6$-alkyl, —C(=O)—N—(C$_1$-C$_6$-alkyl)$_2$, —(C$_0$-C$_3$)-alkyl-aryl and —(C$_0$-C$_3$)-alkyl-heteroaryl is unsubstituted or substituted with 1 to 7 substituents independently selected from halogen, cyano, C$_1$-C$_6$-alkoxy and —C(=O)—O—C$_1$-C$_6$-alkyl;

Q is selected from H, hydroxy, —C(=O)H, C$_1$-C$_6$-alkyl, C$_1$-C$_6$-alkoxy, C$_2$-C$_6$ alkenyl, C$_2$-C$_6$ alkynyl, —C$_0$-C$_3$-alkyl-C$_3$-C$_7$ cycloalkyl, —C$_0$-C$_3$-alkyl-C$_3$-C$_7$ heterocycloalkyl, —C$_0$-C$_3$-alkyl-aryl, —C$_0$-C$_3$-alkyl-heteroaryl, —NH—(C$_1$-C$_6$-alkyl), —N—(C$_1$-C$_6$-alkyl)$_2$ and —C(=O)N—(C$_1$-C$_6$-alkyl)$_2$, wherein each of C$_1$-C$_6$-alkyl, C$_1$-C$_6$-alkoxy, C$_2$-C$_6$ alkenyl, C$_2$-C$_6$ alkynyl, —C$_0$-C$_3$-alkyl-C$_3$-C$_7$ cycloalkyl, —C$_0$-C$_3$-alkyl-C$_3$-C$_7$ heterocycloalkyl, —C$_0$-C$_3$-alkyl-aryl, —C$_0$-C$_3$-alkyl-heteroaryl, —NH—(C$_1$-C$_6$-alkyl), —N—(C$_1$-C$_6$-alkyl)$_2$ and —C(=O)N—(C$_1$-C$_6$-alkyl)$_2$ is unsubstituted or substituted with 1 to 7 substituents independently selected from halogen, hydroxyl, nitro, amino, cyano, C$_1$-C$_6$-haloalkyl, C$_1$-C$_6$-alkoxy, C$_1$-C$_6$-alkoxycarbonyl, —C(=O)OH, C$_1$-C$_6$-alkylcarbamoyl, —C(=O)NH$_2$, —C(=S)NH$_2$, C$_3$-C$_6$-cycloalkylcarbamoyl and phenyl;

W is O or S;

L is selected from

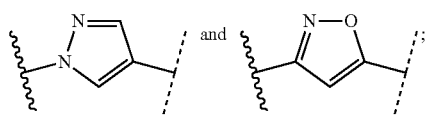

wherein

indicates the bond to the group

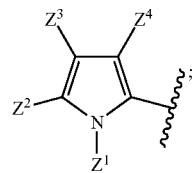

T is selected from

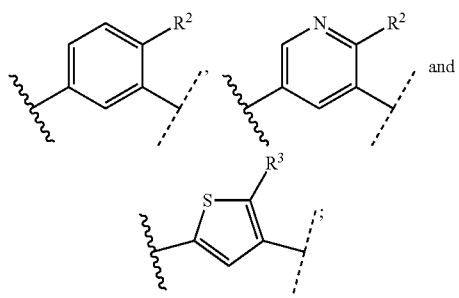

wherein

indicates the bond to the L group;

R$^2$ is H, Cl or Br;

R$^3$ is selected from Cl, Br and CN;

Z$^1$ is selected from H, C$_1$-C$_6$-alkyl and C$_3$-C$_6$-cycloalkyl wherein C$_1$-C$_6$-alkyl and C$_3$-C$_6$-cycloalkyl is unsubstituted or substituted with 1 to 9 substituents independently selected from halogen, cyano and C$_1$-C$_6$-alkoxy;

Z$^2$ and Z$^4$ are independently selected from H, halogen, cyano, nitro, C$_1$-C$_6$-alkyl, —C(=S)—NH$_2$, —C(=S)—NH(C$_1$-C$_6$-alkyl), —C(=S)—N(C$_1$-C$_6$-alkyl)$_2$, C$_3$-C$_7$ heterocycloalkyl, C$_3$-C$_6$-cycloalkyl, —S—C$_1$-C$_6$-alkyl, —S—C$_3$-C$_5$-cycloalkyl, —SO—C$_1$-C$_6$-alkyl, —SO—C$_3$-C$_5$-cycloalkyl, —SO$_2$—C$_1$-C$_6$-alkyl, —SO$_2$—C$_3$-C$_5$-cycloalkyl, —SO$_2$—O—C$_1$-C$_6$-alkyl, —SO$_2$—O—C$_3$-C$_5$-cycloalkyl, —C$_0$-C$_3$-alkyl-aryl, —C$_0$-C$_3$-alkyl-heteroaryl, wherein each of —C(=S)—NH(C$_1$-C$_6$-alkyl), —C(=S)—N(C$_1$-C$_6$-alkyl)$_2$, C$_1$-C$_6$-alkyl, C$_3$-C$_7$ heterocycloalkyl, C$_3$-C$_6$-cycloalkyl, —S—C$_1$-C$_6$-alkyl, —S—C$_3$-C$_5$-cycloalkyl, —SO—C$_1$-C$_6$-alkyl, —SO—C$_3$-C$_5$-cycloalkyl, —SO$_2$—C$_1$-C$_6$-alkyl, —SO$_2$—C$_3$-C$_5$-cycloalkyl, —SO$_2$—O—C$_1$-C$_6$-alkyl, —SO$_2$—O—C$_3$-C$_5$-cycloalkyl, —C$_0$-C$_3$-alkyl-aryl and —C$_0$-C$_3$-alkyl-heteroaryl is unsubstituted or substituted with 1 to 9 substituents independently selected from halogen, hydroxy, nitro, amino, cyano, C$_1$-C$_6$-alkyl, C$_1$-C$_6$-haloalkyl, C$_1$-C$_6$-alkoxy, C$_1$-C$_6$-alkoxycarbonyl and hydroxycarbonyl;

Z$^3$ is selected from H and halogen;

or an agrochemically acceptable salt thereof.

2. The compound or salt according to claim 1, wherein T is

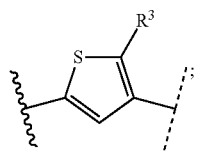

wherein

indicates the bond to the L group;
$R^3$ is selected from Cl, Br and CN.

3. The compound or salt according to claim 1, wherein T is

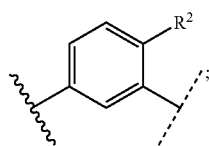

wherein

indicates the bond to the L group;
$R^2$ is H, Cl or Br.

4. The compound or salt according to claim 1, wherein T is

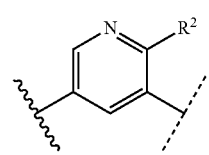

wherein

indicates the bond to the L group;
$R^2$ is H, Cl or Br.

5. The compound or salt according to claim 1, wherein L is

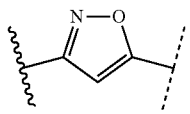

wherein

indicates the bond to the group

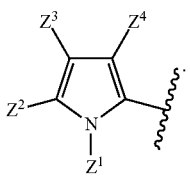

6. A compound or salt according to claim 1, wherein L is

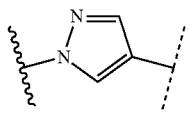

wherein

indicates the bond to the group

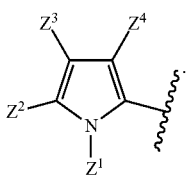

7. The compound or salt according to claim 1, wherein $R^1$ is selected from H and $C_1$-$C_6$-alkyl.

8. The compound or salt according to claim 1, wherein Q is $C_3$-$C_6$-cycloalkyl which is unsubstituted or substituted with 1 to 3 substituents independently selected from halogen and cyano.

9. The compound or salt according to claim 1, wherein
$Z^1$ is $C_1$-$C_6$-alkyl wherein $C_1$-$C_6$-alkyl is unsubstituted or substituted with 1 to 7 halogen substituents;
$Z^2$ is selected from $C_1$-$C_6$-alkyl which is substituted with 1 to 7 halogen substituents;

$Z^3$ is H or bromo;

$Z^4$ is selected from H, halogen, nitro, cyano, methyl, trifluoromethyl and —C(=S)—NH$_2$.

10. The compound or salt according to claim 1, wherein $Z^1$ is selected from methyl, —CH$_2$CN, —CH$_2$F and —CH$_2$—O—CH$_3$;

$Z^2$ is selected from —CF(CF$_3$)(CF$_3$);

$Z^3$ is H or bromo;

$Z^4$ is selected from H, halogen, nitro, cyano, methyl, trifluoromethyl and —C(=S)—NH$_2$.

11. A pesticidal composition, which comprises at least one compound according to claim 1, or an agrochemically acceptable salt or N-oxide thereof, as active ingredient and at least one auxiliary.

12. The composition according to claim 11, which further comprises one or more additional insecticidally, acaricidally, nematicidally and/or fungicidally active agents.

13. A method for controlling insect, acarine, mollusc, and nematode pests, which comprises applying a composition according to claim 11 to the pests or their environment with the proviso that treating human or animal bodies by surgery or therapy and/or diagnostic methods practiced on human or animal bodies are excluded.

14. A method for the protection of plant propagation material from attack by insect, acarine, mollusc, and nematode pests, which comprises treating the propagation material or the site, where the propagation material is planted, with a composition according to claim 11.

15. A coated plant propagation material, wherein the coating of the plant propagation material comprises a compound as defined in claim 1.

16. A compound selected from:

2-chloro-N-(1-cyanocyclopropyl)-5-[1-[1-methyl-5-[1,2,2,2-tetrafluoro-1-(trifluoromethyl)ethyl]pyrrol-2-yl]pyrazol-4-yl]benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-N-methyl-benzamide;

2-chloro-N-(1-cyanocyclopropyl)-5-[3-[1-methyl-5-[1,2,2,2-tetrafluoro-1-(trifluoromethyl)ethyl]pyrrol-2-yl]isoxazol-5-yl]benzamide;

5-[3-[3-bromo-1-methyl-5-[1,2,2,2-tetrafluoro-1-(trifluoromethyl)ethyl]pyrrol-2-yl]isoxazol-5-yl]-2-chloro-N-(1-cyanocyclopropyl)benzamide;

2-chloro-N-(1-cyanocyclopropyl)-5-[1-[1-methyl-3-nitro-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-[1-methyl-5-[1,2,2,2-tetrafluoro-1-(trifluoromethyl)ethyl]-3-(trifluoromethyl)pyrrol-2-yl]pyrazol-4-yl]benzamide;

2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)benzamide;

2-chloro-N-(1-cyanocyclopropyl)-5-[1-[3-cyano-1-methyl-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-[1,3-dimethyl-5-[1,2,2,2-tetrafluoro-1-(trifluoromethyl)ethyl]pyrrol-2-yl]pyrazol-4-yl]benzamide;

5-[1-[3-bromo-1-(fluoromethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-(cyanomethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-(methoxymethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide;

2-chloro-N-(1-cyanocyclopropyl)-5-[1-(3,4,5-tribromo-1-methyl-pyrrol-2-yl)pyrazol-4-yl]benzamide;

2-chloro-N-(1-cyanocyclopropyl)-5-[1-[3,4-dibromo-1-methyl-5-(trifluoromethylsulfanyl)pyrrol-2-yl]pyrazol-4-yl]benzamide;

5-[1-[3-bromo-5-[1-(3,5-difluorophenyl)-1,2,2,2-tetrafluoro-ethyl]-1-methyl-pyrrol-2-yl]pyrazol-4-yl]-2-chloro-N-(1-cyanocyclopropyl)benzamide;

5-[1-[3-chloro-1-methyl-5-[1,2,2,2-tetrafluoro-1-(trifluoromethyl)ethyl]pyrrol-2-yl]pyrazol-4-yl]-2-cyano-N-cyclopropyl-thiophene-3-carboxamide;

2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)pyridine-3-carboxamide;

5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)-N-ethyl-benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)-N-methyl-benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-N-ethyl-benzamide;

5-[1-[3-carbamothioyl-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-isopropyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-tert-butyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-5-[1,2,2,2-tetrafluoro-1-(trifluoromethyl)ethyl]-1-(2,2,2-trifluoroethyl)pyrrol-2-yl]pyrazol-4-yl]-2-chloro-N-(1-cyanocyclopropyl)benzamide;

5-[1-[3-bromo-5-[1,2,2,3,3,3-hexafluoro-1-(trifluoromethyl)propyl]-1-methyl-pyrrol-2-yl]pyrazol-4-yl]-2-chloro-N-(1-cyanocyclopropyl)benzamide;

2-chloro-N-(1-cyanocyclopropyl)-5-[1-[5-[1,2,2,3,3,3-hexafluoro-1-(trifluoromethyl)propyl]-1-methyl-pyrrol-2-yl]pyrazol-4-yl]benzamide;

2-chloro-5-[1-[3-chloro-1-(fluoromethyl)-5-[1,2,2,2-tetrafluoro-1-(trifluoromethyl)ethyl]pyrrol-2-yl]pyrazol-4-yl]-N-(1-cyanocyclopropyl)benzamide;

2-chloro-5-[1-[3-chloro-5-[1-(3,5-dichlorophenyl)-1,2,2,2-tetrafluoro-ethyl]-1-methyl-pyrrol-2-yl]pyrazol-4-yl]-N-(1-cyanocyclopropyl)benzamide;

5-[1-[3-bromo-1-methyl-5-(1,1,2,2,2-pentafluoroethyl)pyrrol-2-yl]pyrazol-4-yl]-2-chloro-N-(1-cyanocyclopropyl)benzamide;

2-chloro-5-[1-[3-chloro-1-methyl-5-(trifluoromethylsulfanyl)pyrrol-2-yl]pyrazol-4-yl]-N-(1-cyanocyclopropyl)benzamide;

2-chloro-5-[1-[3-chloro-1-methyl-5-(1,1,2,2,2-pentafluoroethyl)pyrrol-2-yl]pyrazol-4-yl]-N-(1-cyanocyclopropyl)benzamide;

2-chloro-N-(1-cyanocyclopropyl)-5-[1-[3-iodo-1-methyl-5-[1,2,2,2-tetrafluoro-1-(trifluoromethyl)ethyl]pyrrol-2-yl]pyrazol-4-yl]benzamide;

N-acetyl-2-chloro-N-(1-cyano-1-methyl-ethyl)-5-[1-[1-cyclopropyl-5-[1,2,2,2-tetrafluoro-1-(trifluoromethyl)ethyl]pyrrol-2-yl]pyrazol-4-yl]benzamide;

N-acetyl-2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]benzamide;

2-chloro-N-(1-cyano-1-methyl-ethyl)-5-[1-[1-cyclopropyl-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]-N-methyl-benzamide;

methyl N-[2-chloro-5-[1-[1-cyclopropyl-5-[1,2,2,2-tetrafluoro-1-(trifluoromethyl)ethyl]pyrrol-2-yl]pyrazol-4-yl]benzoyl]-N-(1-cyanocyclopropyl)carbamate;

2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-[3,4-dibromo-1-cyclopropyl-5-(trifluoromethylsulfanyl)pyrrol-2-yl]pyrazol-4-yl]benzamide; and 5-[1-[3-bromo-1-cyclopropyl-5-[1,2,2,2-tetrafluoro-1-(trifluoromethyl)ethyl]pyrrol-2-yl]pyrazol-4-yl]-2-chloro-N-(1-cyanocyclopropyl)benzamide.

17. The compound of claim 16, wherein the compound is selected from:

2-chloro-N-(1-cyanocyclopropyl)-5-[1-[1-methyl-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[3-[1-methyl-5-[1,2,2,2-tetrafluoro-1-(trifluoromethyl)ethyl]pyrrol-2-yl]isoxazol-5-yl]benzamide;

2-chloro-N-(1-cyanocyclopropyl)-5-[1-[1-methyl-3-nitro-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-[1-methyl-5-[1,2,2,2-tetrafluoro-1-(trifluoromethyl)ethyl]-3-(trifluoromethyl)pyrrol-2-yl]pyrazol-4-yl]benzamide;

2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)benzamide;

2-chloro-N-(1-cyanocyclopropyl)-5-[1-[3-cyano-1-methyl-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-[1,3-dimethyl-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-(3,4,5-tribromo-1-methyl-pyrrol-2-yl)pyrazol-4-yl]benzamide;

2-chloro-N-(1-cyanocyclopropyl)-5-[1-[3,4-dibromo-1-methyl-5-(trifluoromethylsulfanyl)pyrrol-2-yl]pyrazol-4-yl]benzamide;

2-chloro-5-[1-[3-chloro-1-methyl-5-[1,2,2,2-tetrafluoro-1-(trifluoromethyl)ethyl]pyrrol-2-yl]pyrazol-4-yl]-N-(1-cyanocyclopropyl)pyridine-3-carboxamide;

2-chloro-N-(1-cyanocyclopropyl)-5-[1-[5-[1,2,2,3,3,3-hexafluoro-1-(trifluoromethyl)propyl]-1-methyl-pyrrol-2-yl]pyrazol-4-yl]benzamide;

2-chloro-5-[1-[3-chloro-1-(fluoromethyl)-5-[1,2,2,2-tetrafluoro-1-(trifluoromethyl)ethyl]pyrrol-2-yl]pyrazol-4-yl]-N-(1-cyanocyclopropyl)benzamide;

2-chloro-5-[1-[3-chloro-5-[1-(3,5-dichlorophenyl)-1,2,2,2-tetrafluoro-ethyl]-1-methyl-pyrrol-2-yl]pyrazol-4-yl]-N-(1-cyanocyclopropyl)benzamide;

5-[1-[3-bromo-1-methyl-5-(1,1,2,2,2-pentafluoroethyl)pyrrol-2-yl]pyrazol-4-yl]-2-chloro-N-(1-cyanocyclopropyl)benzamide;

2-chloro-5-[1-[3-chloro-1-methyl-5-(trifluoromethylsulfanyl)pyrrol-2-yl]pyrazol-4-yl]-N-(1-cyanocyclopropyl)benzamide;

2-chloro-5-[1-[3-chloro-1-methyl-5-(1,1,2,2,2-pentafluoroethyl)pyrrol-2-yl]pyrazol-4-yl]-N-(1-cyanocyclopropyl)benzamide;

2-chloro-N-(1-cyanocyclopropyl)-5-[1-[3-iodo-1-methyl-5-[1,2,2,2-tetrafluoro-1-(trifluoromethyl)ethyl]pyrrol-2-yl]pyrazol-4-yl]benzamide;

2-chloro-N-(1-cyano-1-methyl-ethyl)-5-[1-[1-cyclopropyl-5-[1,2,2,2-tetrafluoro-1-(trifluoromethyl)ethyl]pyrrol-2-yl]pyrazol-4-yl]benzamide;

2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]-N-methyl-benzamide;

2-chloro-N-(1-cyanocyclopropyl)-5-[1-[1-cyclopropyl-5-[1,2,2,2-tetrafluoro-1-(trifluoromethyl)ethyl]pyrrol-2-yl]pyrazol-4-yl]benzamide; and 2-chloro-N-(1-cyanocyclopropyl)-5-[1-[3,4-dibromo-1-cyclopropyl-5-(trifluoromethylsulfanyl)pyrrol-2-yl]pyrazol-4-yl]benzamide.

18. The compound of claim 16, wherein the compound is selected from:

5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-N-methyl-benzamide;

5-[3-[3-bromo-1-methyl-5-[1,2,2,2-tetrafluoro-1-(trifluoromethyl)ethyl]pyrrol-2-yl]isoxazol-5-yl]-2-chloro-N-(1-cyanocyclopropyl)benzamide;

5-[1-[3-bromo-1-(fluoromethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-(cyanomethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-(methoxymethyl)-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-5-[1-(3,5-difluorophenyl)-1,2,2,2-tetrafluoro-ethyl]-1-methyl-pyrrol-2-yl]pyrazol-4-yl]-2-chloro-N-(1-cyanocyclopropyl)benzamide;

5-[1-[3-chloro-1-methyl-5-[1,2,2,2-tetrafluoro-1-(trifluoromethyl)ethyl]pyrrol-2-yl]pyrazol-4-yl]-2-cyano-N-cyclopropyl-thiophene-3-carboxamide;

5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)-N-ethyl-benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-(1-cyanocyclopropyl)-N-methyl-benzamide;

5-[1-[3-bromo-1-methyl-5-[1,2,2,2-tetrafluoro-1-(trifluoromethyl)ethyl]pyrrol-2-yl]pyrazol-4-yl]-2-chloro-N-cyclopropyl-N-ethyl-benzamide;

5-[1-[3-carbamothioyl-1-methyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-isopropyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-1-tert-butyl-5-[1,2,2,2-tetrafluoro-1-(trifluoromethyl)ethyl]pyrrol-2-yl]pyrazol-4-yl]-2-chloro-N-(1-cyanocyclopropyl)benzamide;

5-[1-[3-bromo-5-[1,2,2,2-tetrafluoro-1-(trifluoromethyl)ethyl]-1-(2,2,2-trifluoroethyl)pyrrol-2-yl]pyrazol-4-yl]-2-chloro-N-(1-cyanocyclopropyl)benzamide;

5-[1-[3-bromo-5-[1,2,2,3,3,3-hexafluoro-1-(trifluoromethyl)propyl]-1-methyl-pyrrol-2-yl]pyrazol-4-yl]-2-chloro-N-(1-cyanocyclopropyl)benzamide; and 5-[1-[3-bromo-1-cyclopropyl-5-[1,2,2,2-tetrafluoro-1-(trifluoromethyl)ethyl]pyrrol-2-yl]pyrazol-4-yl]-2-chloro-N-(1-cyanocyclopropyl)benzamide.

19. The compound of claim 16, wherein the compound is selected from:

N-acetyl-2-chloro-N-(1-cyano-1-methyl-ethyl)-5-[1-[1-cyclopropyl-5-[1,2,2,2-tetrafluoro-1-(trifluoromethyl)ethyl]pyrrol-2-yl]pyrazol-4-yl]benzamide; and N-acetyl-2-chloro-N-(1-cyanocyclopropyl)-5-[1-[1-cyclopropyl-5-[1,2,2,2-tetrafluoro-1-trifluoromethyl)ethyl]pyrrol-2-yl]pyrazol-4-yl]benzamide.

20. The compound of claim 16, wherein the compound is selected from:

methyl N-[2-chloro-5-[1-[1-cyclopropyl-5-[1,2,2,2-tetrafluoro-1-(trifluoromethyl)ethyl]pyrrol-2-yl]pyrazol-4-yl]benzoyl]-N-(1-cyanocyclopropyl)carbamate.

\* \* \* \* \*